United States Patent
Chen et al.

(10) Patent No.: US 11,753,432 B2
(45) Date of Patent: Sep. 12, 2023

(54) COMPOUND WITH ANALGESIC EFFECT FOR USE IN PREVENTION AND TREATMENT OF PAIN

(71) Applicant: Academia Sinica, Taipei (TW)

(72) Inventors: Chih-Cheng Chen, Taipei (TW); Jim-Min Fang, Taipei (TW); Cheng-Han Lee, New Taipei (TW); Jen-Yao Chang, Taipei (TW)

(73) Assignee: ACADEMIA SINICA, Taipei (TW)

( * ) Notice: Subject to any disclaimer, the term of this patent is extended or adjusted under 35 U.S.C. 154(b) by 78 days.

(21) Appl. No.: 16/481,042

(22) PCT Filed: Jan. 26, 2018

(86) PCT No.: PCT/US2018/015460
§ 371 (c)(1),
(2) Date: Jul. 25, 2019

(87) PCT Pub. No.: WO2018/140734
PCT Pub. Date: Aug. 2, 2018

(65) Prior Publication Data
US 2019/0389898 A1 Dec. 26, 2019

Related U.S. Application Data

(60) Provisional application No. 62/451,322, filed on Jan. 27, 2017.

(51) Int. Cl.
| | |
|---|---|
| *C07H 19/16* | (2006.01) |
| *A61K 47/55* | (2017.01) |
| *A61P 29/00* | (2006.01) |
| *A61K 31/7076* | (2006.01) |
| *A61K 38/04* | (2006.01) |

(52) U.S. Cl.
CPC ......... *C07H 19/16* (2013.01); *A61K 31/7076* (2013.01); *A61K 38/046* (2013.01); *A61K 47/55* (2017.08); *A61P 29/00* (2018.01)

(58) Field of Classification Search
CPC .... C07H 19/16; A61K 47/55; A61K 31/7076; A61K 38/046; A61P 29/00
See application file for complete search history.

(56) References Cited

U.S. PATENT DOCUMENTS

| | | | |
|---|---|---|---|
| 4,755,594 A | 7/1988 | Bridges et al. | |
| 5,459,132 A | 10/1995 | Bru-Magniez et al. | |
| 2006/0100168 A1 | 5/2006 | Ravid et al. | |

FOREIGN PATENT DOCUMENTS

| | | |
|---|---|---|
| CN | 102740849 A | 10/2012 |
| CN | 104363757 A | 2/2015 |
| EP | 1352910 A1 | 10/2003 |
| EP | 2511283 A1 | 10/2012 |
| WO | 1995018817 A1 | 7/1995 |
| WO | 2003084975 A1 | 10/2003 |
| WO | 2005012323 A2 | 2/2005 |
| WO | 2005084653 A2 | 9/2005 |
| WO | 2015061426 A1 | 4/2015 |
| WO | 2013120078 A1 | 8/2018 |

OTHER PUBLICATIONS

International Search Report and Written Opinion in International Patent Application No. PCT/US18/15460, dated May 14, 2018, in 14 pages.
Wei, W. et al., "Adenosine analogs as inhibitors of tyrosyl-tRNA synthetase: Design, synthesis and antibacterial evaluation", Bioorganic & Medicinal Chemistry, 2015, vol. 23, pp. 6602-6611.
Montalbetti, C. A. G. N. et al., "Amide bond formation and peptide coupling", Tetrahedron, 2005, vol. 61, pp. 10827-10852.
Marinier, B. et al., "The 2,2,2-Trichloroethyl Group for Carboxyl Protection During Peptide Synthesis", Canadian Journal of Chemistry, 1973, vol. 51, pp. 208-214.
Taylor, C.; Angelotti, T.; Fauman, E. Pharmacology and mechanism of action of pregabalin: the calcium channel alpha2-delta ($\alpha 2$-$\delta$) subunit as a target for antiepileptic drug discovery. Epilepsy Res. 2007, 73(2), 137-150.
Derry, S.; Gill, D.; Phillips, T.; Moore, R. Milnacipran for neuropathic pain and fibromyalgia in adults. Cochrane Database Syst. Rev. Mar. 14, 2012;(3), 53 pages: CD008244. doi: 10.1002/14651858.CD008244.pub2.
Lunn, M.; Hughes, R. and Wiffen, P. Duloxetine for treating painful neuropathy, chronic pain or fibromyalgia. The Cochrane Library, 2014, 125 pages, John Wiley & Sons, Ltd., doi:10.1002/14651858.CD007115.pub3.
National Pain Foundation, Fibromyalgia drugs: successes or failures? National Pain Report, Apr. 23, 2014, Pat Anson, Ed., downloaded Oct. 4, 2019, 17 pages.
Lin, C.-C.J.; Chen, W.-N.; Chen, C.-J.; Lin, Y.-W.; Zimmer, A.; Chen, C.-C. An antinociceptive role for substance P in acid-induced chronic muscle pain. Proc. Natl. Acad Sci. U. S. A. 2012, 109, E76-E83.
Sun, W. H.; Chen, C. C. Roles of proton-sensing receptors in the transition from acute to chronic pain. J. Dent. Res. 2016, 95, 135-142.
Hill, R. NK1 (substance P) receptor antagonists—why are they not analgesic in humans? Trends Pharmacol. Sci. 2000, 21, 244-246.
Deval, E.; Noël, J.; Gasull, X.; Delaunayl, A.; Alloui, A.; Friend, V.; Eschalier, A.; Lazdunski, M., Lingueglia, E. Acid-sensing ion channels in postoperative pain. J Neurosci. 2011, 31, 6059-6066.

(Continued)

*Primary Examiner* — Li N Komatsu

(74) *Attorney, Agent, or Firm* — DUANE MORRIS LLP

(57) ABSTRACT

Compounds for use in prevention and/or treatment of pain are disclosed. The compounds are derived by conjugation of $N^6$-(4-hydroxybenzyl)adenosine and analogous compounds with amino acids or peptides. In one embodiment of the invention, the compound is 5'-O-(glycine-N-carbonyl-$N^6$-(4-hydroxybenzyl)adenosine (I-a1). In another embodiment of the invention, the compound is 5-deoxy-5'-(glycine-N-amido)-N6-(4-hydroxybenzyl)adenosine (I-d1). Also disclosed are methods of making and using the same.

16 Claims, 9 Drawing Sheets

Specification includes a Sequence Listing.

(56) References Cited

OTHER PUBLICATIONS

Chen, J.-B.; Liu, E. M.; Chem, T.-R.; Yang, C.-W.; Lin, C.-I.; Huang, N.-K.; Lin, Y.-L.; Chern, Y.; Lin, J.-H. Fang, J.-M. Design and synthesis of novel dual-action compounds targeting the adenosine A2A receptor and adenosine transporter for neuroprotection. ChemMedChem 2011, 6, 1390-1400.

Nishiyori, M.; Ueda, H. Prolonged gabapentin analgesia in an experimental mouse model of fibromyalgia. Mol. Pain 2008, 4, 52, 6 pages.

Extended European Search Report in EP Application No. 18745468.1, dated Dec. 11, 2020, in 10 pages.

SEQUENCE LISTING

```
<160> NUMBER OF SEQ ID NOS: 3

<210> SEQ ID NO 1
<211> LENGTH: 11
<212> TYPE: PRT
<213> ORGANISM: Artificial Sequence
<220> FEATURE:
<223> OTHER INFORMATION: Polypeptide
<220> FEATURE:
<221> NAME/KEY: MOD_RES
<222> LOCATION: (11)..(11)
<223> OTHER INFORMATION: AMIDATION

<400> SEQUENCE: 1

Arg Pro Lys Pro Gln Gln Phe Phe Gly Leu Met
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Polypeptide
<220> FEATURE:
<221> NAME/KEY: MISC_FEATURE
<222> LOCATION: (3)..(3)
<223> OTHER INFORMATION: N6-(4-hydroxybenzyl)adenosine
<220> FEATURE:
<221> NAME/KEY: MOD_RES
<222> LOCATION: (11)..(11)
<223> OTHER INFORMATION: AMIDATION

<400> SEQUENCE: 2

Arg Pro Lys Pro Gln Gln Phe Phe Gly Leu Met
1               5                   10

<210> SEQ ID NO 3
<211> LENGTH: 5
<212> TYPE: PRT
<213> ORGANISM: Artificial Sequence
<220> FEATURE:
```

```
<223> OTHER INFORMATION: synthetic construct
<220> FEATURE:
<221> NAME/KEY: VARIANT
<222> LOCATION: (2)..(2)
<223> OTHER INFORMATION: X is either an aromatic or aliphatic amino acid
<220> FEATURE:
<221> NAME/KEY: MOD_RES
<222> LOCATION: (5)..(5)
<223> OTHER INFORMATION: AMIDATION

<400> SEQUENCE: 3

Phe Xaa Gly Leu Met
1               5
```

COMPOUND WITH ANALGESIC EFFECT FOR USE IN PREVENTION AND TREATMENT OF PAIN

CROSS-REFERENCE TO RELATED APPLICATIONS

This application is a § 371 national stage entry of International Application No. PCT/US2018/015460, filed Jan. 26, 2018, which claims the benefit of priority to U.S. Provisional 62/451,322, filed on Jan. 27, 2017, the entire contents of each of which are incorporated herein by reference in their entirety.

SEQUENCE LISTING

The instant application contains a Sequence Listing which has been submitted electronically in computer readable format and is hereby incorporated by reference in its entirety. Said computer readable format copy, created on Dec. 30, 2022, is named G4590-02701_US9113-sequence_listing_December_2022_30_ST25.txt and is 2 kilobytes in size. The information recorded in computer readable form is identical to the written sequence listing.

FIELD OF THE INVENTION

The present invention relates to a compound for use in preventing and/or treating pain. Particularly, the invention pertains to adenosine derivatives and their applications in preventing and/or treating a pain.

BACKGROUND OF THE INVENTION

Pain is an uncomfortable feeling usually caused by intense stimuli or tissue/nerve damage. Pain can be classified into acute/chronic dichotomy by the affecting time. Acute pain can last just a moment or weeks depending on the circumstance. Acute pain usually disappears after recovery of the damaged tissue. Chronic pain is defined as pain which lasts more than 3-6 months, and is the normal healing time of an injury. There is a large population having chronic pain, and about one fifth of patients reported with chronic pain have predominantly neuropathic pain. Neuropathic pain is the pain arising from the nervous system, which is affected by a lesion or disease. Unlike nociceptive pain, which can be relieved by opioids or non-steroidal anti-inflammatory drugs (NSAIDs), neuropathic pain lacks effective treatments.

Fibromyalgia (FM) syndrome is characterized by chronic widespread pain and tenderness. The symptoms of fatigue, sleep disturbance and cognitive dysfunction may also occur. The major cause of FM remains unknown, but it is characterized by a decrease in the nociceptive pain threshold. Fibromyalgia and neuropathic pain have some diversities in the pathology of the peripheral and central nervous system.

Pregabalin (Lyrica®) and gabapentin (Neurotin®) are recommended for the treatment of neuropathic pain. Pregabalin and gabapentin have the structures analogous to γ-aminobutyric acid (GABA), but they do not interact with GABA receptors. These two drugs act by interacting with calcium channel $\alpha_2$-δ subunit, resulting in the reduction of various neurotransmitters that are released from the synapse [Taylor, C.; Angelotti, T.; Fauman, E. Pharmacology and mechanism of action of pregabalin: the calcium channel alpha2-delta (α2-δ) subunit as a target for antiepileptic drug discovery. *Epilepsy Res.* 2006, 73, 137-150]. The labeled use of pregabalin (25 mg/day) and gabapentin (300 mg/day) also include anticonvulsants; however, side effects including sedation, dizziness and edema have been reported.

Milnacipran (Savella®) and duloxetine (Cymbalta®) are also used for the treatment of neuropathic pain, as well as for FM [Derry, S.; Gill, D.; Phillips, T.; Moore, R. Milnacipran for neuropathic pain and fibromyalgia in adults. *Cochrane Database Syst. Rev.* 2012, doi:10.1002/14651858.CD008244.pub2; Lunn, M.; Hughes, R. and Wiffen, P. Duloxetine for treating painful neuropathy, chronic pain or fibromyalgia. *The Cochrane Library*, 2014, doi:10.1002/14651858.CD007115.pub3]. Milnacipran and duloxetine are serotonin-norepinephrine reuptake inhibitors (SNRI), which prolong the duration of action of serotonin and norepinephrine in the synaptic cleft to enforce the signals induced by serotonin and norepinephrine. The target of serotonin is the 5-hydroxyltryptamine (5-HT) receptor, which contains more than 15 subtypes related to both pro-nociceptive and anti-nociceptive effects, depending on the subtype activated by serotonin. The anti-nociceptive effect of norepinephrine is mediated by $\alpha_2$ adrenergic receptor.

Cymbalta®, Lyrica® and Savella® are the only drugs approved for FM treatment by the FDA. However, two thirds of patients taking these drugs do not consider them as effective medication, according to an online survey conducted by the National Pain Foundation on more than 1300 FM patients [National Pain Foundation, Fibromyalgia drugs: successes or failures? *National Pain Report* 2014, April 23]. This disappointing result may reflect our insufficient understanding of FM.

It was previously identified a novel anti-nociceptive signaling mechanism of substance P by demonstrating that targeting of SP to ASIC3-positive muscle nociceptors inhibits chronic widespread pain [Lin, C.-C. J.; Chen, W.-N.; Chen, C.-J.; Lin, Y.-W.; Zimmer, A.; Chen, C.-C. An antinociceptive role for substance P in acid-induced chronic muscle pain. *Proc. Natl. Acad. Sci. U.S.A.* 2012, 109, E76; Sun, W. H.; Chen, C. C. Roles of proton-sensing receptors in the transition from acute to chronic pain. *J. Dent. Res.* 2016, 95, 135-142]. Substance P (SP) was first isolated from rabbit's intestine, and its amino-acid sequence was later determined as Arg-Pro-Lys-Pro-Glu-Glu-Phe-Phe-Gly-Leu-Met-CONH$_2$ (SEQ ID NO: 1). SP belongs to the class of tachykinin neuropeptides, which have a similar C-terminus sequence of Phe-X-Gly-Leu-Met-NH$_2$ (SEQ ID NO: 3) (X is either an aromatic or an aliphatic amino acid) and a rather diverse N-terminus. The target of SP is the neurokinin 1 receptor (NK1R), a G protein-coupling receptor (GPCR) expressed in the central and peripheral nervous systems. SP is thought to be a major component of pain transmission, and its action is concentration dependent. Although the NK1R (a member of GPCR) knockout mice showed the hypoalgesic effect compared to wild type mice, the use of NK1R antagonist failed to generate similar results in the clinical trial. The failure in clinical trial is likely due to the species difference of NK1R distribution in supraspinal sites for pain perception [Hill, R. NK1 (substance P) receptor antagonists—why are they not analgesic in humans? *Trends Pharmacol. Sci.* 2000, 21, 244-246].

Based on this mechanism of action, it was previously shown that N$^6$-(4-hydroxybenzyl)adenosine, designated as T1-11 (compound 2), is an anti-nociceptive agent in ASIC3-mediated pain model [Chen, C.-C.; Lin, Y.-L.; Fang, J.-M.; Chern, Y.; Lin, C.-C. J.; Chen, W.-N. Methods and compositions for treating pain.]. T1-11 mediates an outward current in SP-sensitive ASIC3-expressing muscle nociceptors and thus can inhibit acid-induced ASIC3 activation [Deval, E.;

Noel, J.; Gasull, X.; Delaunayl, A.; Alloui, A.; Friend, V.; Eschalier, A.; Lazdunski, M., Lingueglia, E. Acid-sensing ion channels in postoperative pain. *J. Neurosci.* 2011, 31, 6059-6066]. Intramuscular SP mediates an unconventional NK1 receptor signaling pathway to inhibit acid activation in muscle nociceptors, which results in an unexpected antinociceptive effect against chronic mechanical hyperalgesia induced by repeated intramuscular acid injection [Lin, C.-C. J.; Chen, W.-N.; Chen, C.-J.; Lin, Y.-W.; Zimmer, A.; Chen, C.-C. An antinociceptive role for substance P in acid-induced chronic muscle pain. *Proc. Natl. Acad. Sci. U.S.A* 2012, 109, E76-E83].

SUMMARY OF THE INVENTION

In this invention, a conjugate compound Ic-2 derived from T1-11 and substance P is synthesized. Compound Ic-2 showed analgesic effect starting from 14 μg/kg (160 pico mole) in a mouse model of fibromyalgia, in which chronic widespread pain was induced by intermittent cold stress (ICS). Furthermore, a series of compounds were prepared by conjugation with amino acids (e.g., I-a1) or peptides (e.g., I-c1) to test their analgesic activities.

In one aspect, the invention relates to a compound of formula (I):

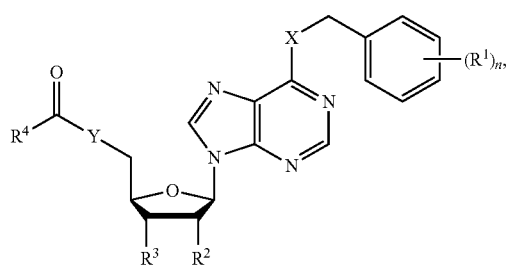

(I)

wherein, n is 0, 1, 2 or 3;

X and Y are each independently NH, O or S;

$R^1$ is OH, $NH_2$, $NO_2$, halogen, alkyl, haloalkyl, hydroxyalkyl, unsubstituted or substituted alkoxy, alkoxyalkyl, alkenyl or alkynyl;

$R^2$ and $R^3$ are each independently OH, $NH_2$, $NO_2$, haloalkyl, hydroxyalkyl or alkylamino; and $R^4$ is a moiety derived from an amino acid or a peptide, and $R^4$ is linked with C(=O) in the structure via the N-terminal group or a side chain amino group thereof, wherein the C-terminal of the amino acid or the peptide is optionally modified;

a tautomer or stereoisomer thereof; or a pharmaceutically acceptable salt of the foregoing.

In another aspect, the invention relates to a compound of formula (II):

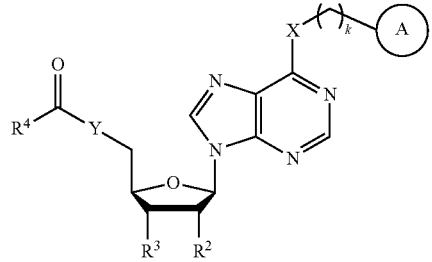

(II)

wherein, k is 1,2 or 3;

X and Y are each independently NH, O or S;

$R^1$ is OH, $NH_2$, $NO_2$, halogen, alkyl, haloalkyl, hydroxyalkyl, unsubstituted or substituted alkoxy, alkoxyalkyl, alkenyl or alkynyl;

$R^2$ and $R^3$ are each independently OH, $NH_2$, $NO_2$, haloalkyl, hydroxyalkyl or alkylamino; and $R^4$ is an amino acid or a peptide;

ring A is a substituted or unsubstituted aromatic heterocycle, comprising 5- or 6-membered heterocycle and fused heterocycle; the heteroatom(s) in the ring are one or more nitrogen, oxygen, and/or sulfur heteroatoms; and the substituent(s) are selected from the group consisting of fluorine, chlorine, bromine, iodine, hydroxyl, nitro, alkyl, trifluoromethyl group and combinations thereof; a tautomer or stereoisomer thereof; and a pharmaceutically acceptable salt of the foregoing.

In another aspect, the invention relates to a composition comprising:

(a) a therapeutically effective amount of the compound as aforementioned or a pharmaceutically acceptable salt thereof; and (b) a pharmaceutically acceptable carrier, excipient or vehicle.

Yet in another aspect, the invention relates to use of the compound as aforementioned in the manufacture of a medicament for treating pain in a subject in need thereof. Alternatively, the invention relates to the compound as aforementioned for use in treating pain in a subject in need thereof.

In one embodiment of the invention, the pain may be acid-induced pain. The acid-induced pain may be acid-induced muscle pain. The acid-induced muscle pain may be acid-induced chronic muscle pain.

In one embodiment of the invention, the pain is selected from the group consisting of inflammatory pain, cancer-associated pain, chest pain, back pain, neck pain, shoulder pain, migraine, headache, myofascial pain, joint pain, muscular pain syndromes, neuropathic pain, peripheral pain, sympathetic pain, postoperative pain, post-traumatic pain, and multiple sclerosis pain.

In another embodiment of the invention, the pain may be a dysfunctional pain. The dysfunctional pain may be selected from the group consisting of fibromyalgia, myofascial pain, bladder pain syndrome, a pain caused by irritable bowel syndrome, and pain associated with temporomandibular disorders.

These and other aspects will become apparent from the following description of the preferred embodiment taken in conjunction with the following drawings, although variations and modifications therein may be affected without departing from the spirit and scope of the novel concepts of the disclosure.

In this invention, compounds of formulae (I) and (II) may be used to treat postoperative pain, myofascial pain syndrome, and other chronic widespread pain, which are pain with muscular origin and associated with ASIC3 and substance P.

Without wishing to be limited by theory, it is believed that the analgesic effect of compound of formulae (I) and (II) is due to the fact that compound of formula (I) and (II) can induce a slow inactivating outward current in muscle nociceptors so that the neurons become hyperpolarized and increased the firing threshold.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 2 shows the synthetic method for compound I-a1 via PMB-protecting intermediate compound 4a.

DETAILED DESCRIPTION OF THE INVENTION

Definitions

Figure 1:
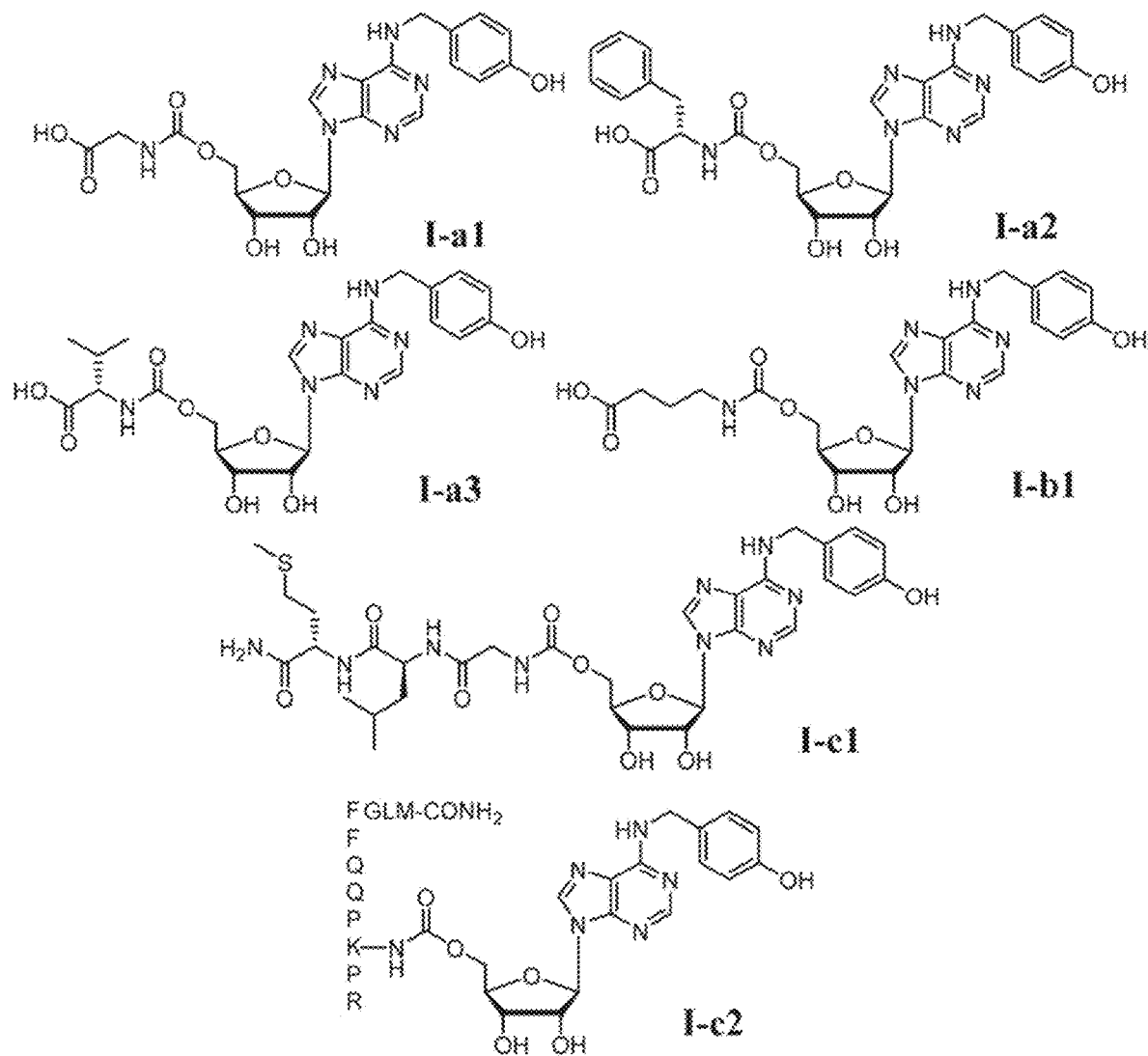
FIG. 1 shows some representative compounds of formula (I). Among them, Compound I-a1 (JMF3737) is a conjugate of T1-11 with glycine. Compound I-c2 (SEQ ID NO:2) is a conjugate of T1-11 with substance P (an undecapeptide RPKPQQFFGLM-CONH$_2$ (SEQ ID NO:1)).

Unless otherwise defined, all technical and scientific terms used herein have the same meaning as commonly understood by one of ordinary skill in the art to which this invention pertains. In the case of conflict, the present document, including definitions will control. As used in this specification and the appended claims, the singular forms "a," "an" and "the" include plural references unless the content clearly dictates otherwise.

Throughout this specification, unless the context requires otherwise, the word "comprise," or variations such as "comprises" or "comprising," will be understood to imply the inclusion of a stated element or integer or group of elements or integers but not the exclusion of any other element or integer or group of elements or integers.

As used herein, the term "halo" means —F, —Cl, —Br or —I.

As used herein, the term "substituted" means that one or more hydrogens on the designated atom is replaced with a selection from the indicated group, provided that the designated atom's normal valency under the existing circumstances is not exceeded, and that the substitution results in a stable compound.

As used herein, the term "alkyl," employed alone or in combination with other terms, refers to a saturated hydrocarbon group that may be straight-chain or branched. In some embodiments, the alkyl group contains 1 to 6, 1 to 4, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, and the like. In some embodiments, the alkyl group is methyl, ethyl, or propyl.

As used herein, the term "alkenyl," employed alone or in combination with other terms, refers to a group derived from an alkyl group where at least one carbon-carbon single bond is replaced with a carbon-carbon double bond. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, pentenyls, hexenyls, and the like.

As used herein, the term "alkynyl," employed alone or in combination with other terms, refers to a group derived from an alkyl group where at least one carbon-carbon single bond is replaced with a carbon-carbon triple bond. In some embodiments, the alkynyl moiety contains 2 to 6 or 2 to 4 carbon atoms. Example alkynyl groups include, but are not limited to, ethynyl, propyn-1-yl, propyn-2-yl, butynyls, pentynyls, hexynyls, and the like.

As used herein, the term "haloalkyl" means a substituted alkyl having one or more halo substituents. For example, "haloalkyl" refers to an alkyl having at least one halogen as the substituent(s) and each substituent may be the same or different; such as mono, di, and trifluoromethyl.

As used herein, the term "alkylamino" refers to the group —NRR' where R is alkyl and R' is hydrogen or alkyl.

As used herein, the term "alkoxyalkyl" refers to an alkoxy group, as defined herein, appended to the parent molecular moiety through an alkyl group, as defined herein. Representative examples of alkoxyalkyl include, but are not limited to, methoxymethyl, methoxyethyl, and methoxypropyl.

As used herein, the term "peptide" refers to short chains of amino acid monomers linked by peptide bonds, preferably 50 or less amino acid monomers, more preferably 2 to 30 amino acids, more preferably 2 to 20 amino acids, such as 9, 10, 11 or 12 amino acids. Peptides include oligopeptides and polypeptides; the former normally have 2 to 20 amino acids while the latter normally have 50 or less amino acids.

As used herein, the term "a derivative of an amino acid or a peptide" includes a salt, an ester or both of an amino acid or a peptide. The salt may derived from the C-terminal, N-terminal and/or side chain group(s) and the ester may derived from the C-terminal and/or side chain group(s).

As used herein, the description "C-terminal modification of an amino acid or a peptide" or the like refers to modifications of the terminal —COOH or replacements of the terminal —COOH with an analog of bioisostere. Examples of modifications include, but are not limited to, esterification, such as methylation, etc. Examples of analogs include, but are not limited to, an amide moiety, a phosphonate moiety, a sulfonate moiety, a hydroxamate moiety, an acyl hydrazide, a phosphonamide, a sulfonamide, etc.

As used herein, "pharmaceutically acceptable salt" refers to derivatives of the disclosed compounds wherein the parent compound is modified by making acid or base salts thereof. Examples of pharmaceutically acceptable salts include, but are not limited to, mineral or organic acid salts of basic residues such as amines, pyridine, pyrimidine and quinazoline; alkali or organic salts of acidic residues such as carboxylic acids; and the like.

As used herein, the term "stereoisomer" is a general term for all isomers of individual molecules that differ only in the orientation of their atoms in space. It includes enantiomers and isomers of compounds with more than one chiral center that are not mirror images of one another (diastereoisomers). The terms "enantiomer" and "enantiomeric" refer to a molecule that cannot be superimposed on its mirror image and hence is optically active wherein the enantiomer rotates the plane of polarized light in one direction and its mirror image compound rotates the plane of polarized light in the opposite direction.

As used herein, the term "tautomer" refers to constitutional isomers of organic compounds that readily interconvert, in particular involving relocation of a proton. Examples of tautomers include, but are not limited to, amino acid and ammonium carboxylate, ketone and enol, etc.

As used herein, the term "treating" or "treatment" refers to administration of an effective amount of a therapeutic agent to a subject in need thereof, who has a neurodegenerative disease and/or pain, or a symptom or predisposition toward such a disease and/or pain, with the purpose of cure, alleviate, relieve, remedy, ameliorate, or prevent the disease and/or pain, the symptoms of it, or the predisposition towards it. Such a subject can be identified by a health care professional based on results from any suitable diagnostic method.

As used herein, the term "effective amount" refers to the amount of an active compound that is required to confer a therapeutic effect on the treated subject. Effective doses will vary, as recognized by those skilled in the art, depending on route of administration, excipient usage, and the possibility of co-usage with other therapeutic treatment.

As used herein, the term "Guidance for Industry and Reviewers Estimating the Safe Starting Dose in Clinical Trials for Therapeutics in Adult Healthy Volunteers" published by the U.S. Department of Health and Human Services Food and Drug Administration discloses a "therapeutically effective amount" may be obtained by calculations from the following formula:

$HED$=animal dose in $mg/kg$×(animal weight in $kg$/human weight in $kg$).

Compounds of the Invention

The invention provides a compound of formula (I):

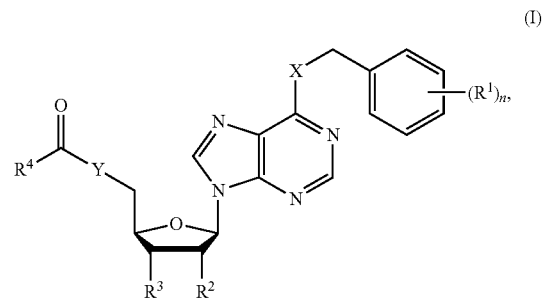

(I)

wherein,
n is 0, 1, 2 or 3;
X and Y are each independently NH, O or S;
$R^1$ is OH, $NH_2$, $NO_2$, halogen, alkyl, haloalkyl, hydroxyalkyl, unsubstituted or substituted alkoxy, alkoxyalkyl, alkenyl or alkynyl;
$R^2$ and $R^3$ are each independently OH, $NH_2$, $NO_2$, haloalkyl, hydroxyalkyl or alkylamino; and
$R^4$ is a moiety derived from an amino acid or a peptide, and $R^4$ is linked with C(=O) in the structure via the N-terminal group or a side chain amino group thereof, wherein the C-terminal of the amino acid or the peptide is optionally modified;
a tautomer or stereoisomer thereof; and a pharmaceutically acceptable salt of the foregoing.

In some embodiment, $R^1$, $R^2$, and $R^3$ are each independently OH.

In one embodiment, n is 1.

In some embodiments, X and Y are each independently NH, O or S.

In a further embodiment, X is NH and Y is O.
In a further embodiment, X is NH and Y is NH.
In a further embodiment, X is NH and Y is S.
The compound of claim 1, wherein X is S and Y is NH.

In some embodiments, $R^4$ is a moiety derived from an amino acid with an acidic side chain, an amino acid with a basic side chain, an amino acid with a polar side chain, an amino acid with a nonpolar side chain; or a moiety derived from a peptide. In some embodiments, $R^4$ is derived from glycine, alanine, cysteine, valine, leucine, isoleucine, methionine, phenylalanine, tryptophan, glutamine, asparagine, threonine, arginine, lysine, proline, or an optionally substituted peptide having less than 20 amino acids. In some embodiments, the amino acid is glycine, valine, cysteine, phenylalanine or glutamine. In one embodiment, the peptide is RPKPQQFFGLM-CONH$_2$ (SEQ ID NO:1), and the peptide is linked with C(=O) in the structure via the side chain amino group of K.

The invention provides a compound of formula (II)

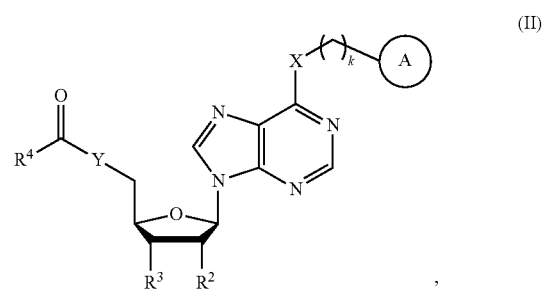

(II)

wherein, k is 1, 2 or 3;

X and Y are each independently NH, O or S;

$R^1$ is OH, $NH_2$, $NO_2$, halogen, alkyl, haloalkyl, hydroxyalkyl, unsubstituted or substituted alkoxy, alkoxyalkyl, alkenyl or alkynyl;

$R^2$ and $R^3$ are each independently OH, $NH_2$, $NO_2$, haloalkyl, hydroxyalkyl or alkylamino; and $R^4$ is an amino acid or a peptide;

ring A is a substituted or unsubstituted aromatic heterocycle, comprising 5- or 6-membered heterocycle and fused heterocycle; the heteroatom(s) in the ring are one or more nitrogen, oxygen, and/or sulfur heteroatoms; and the substituent(s) are selected from the group consisting of fluorine, chlorine, bromine, iodine, hydroxyl, nitro, alkyl, trifluoromethyl group and combinations thereof;

a tautomer or stereoisomer thereof; and a pharmaceutically acceptable salt of the foregoing.

Chemical Synthesis

In another aspect, the invention relates to a method for preparing the compound of formula (I) as aforementioned, comprising the following steps:

(a) reacting $N^6$-(4-hydroxybenzyl)adenosine (2) with 2,2-dimethoxypropane in acetone in the presence of an acid to afford the (2',3'-O-isopropylidene)adenosine compound of formula (3);

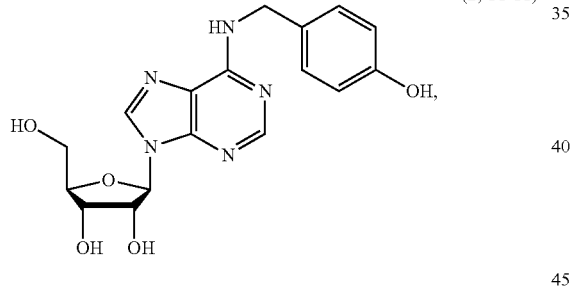

(2, T1-11)

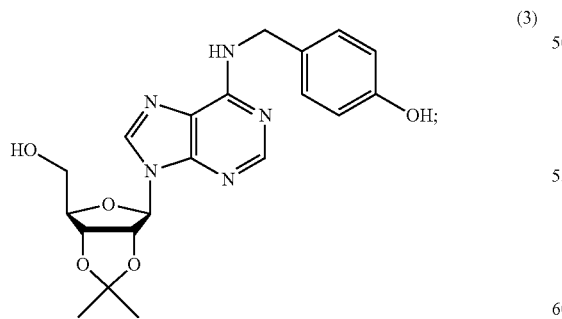

(3)

(b) reacting (2',3'-O-isopropylidene)adenosine compound (3) in the presence of a base with a hydroxyl group-protecting agent to afford a (2',3'-O-isopropylidene) adenosine compound of formula (4) bearing a phenol protecting group (PG);

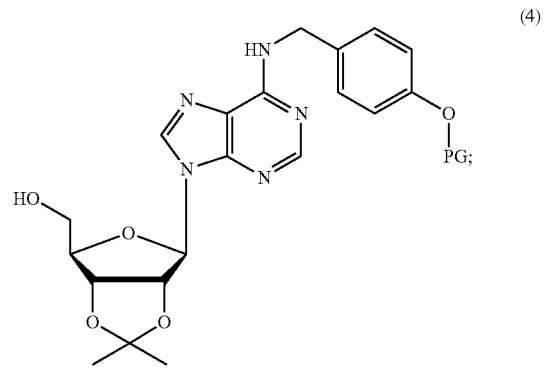

(4)

(c) reacting the (2',3'-O-isopropylidene)adenosine derivative (4) with 1,1'-carbonyldiimidazole (CDI) in the presence of a base to afford a of (2',3'-O-isopropylidene)adenosine compound of formula (5) having the hydroxyl activating group;

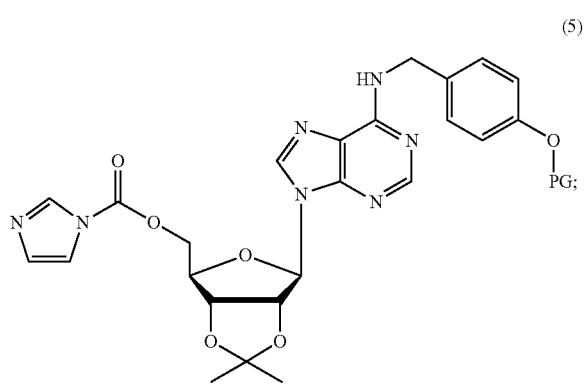

(5)

(d) performing a coupling reaction by reacting the (2',3'-O-isopropylidene)adenosine compound (5) with a derivative of amino acid or peptide (such as an α-amino ester) to afford a (2',3'-O-isopropylidene)adenosine compound of formula (6);

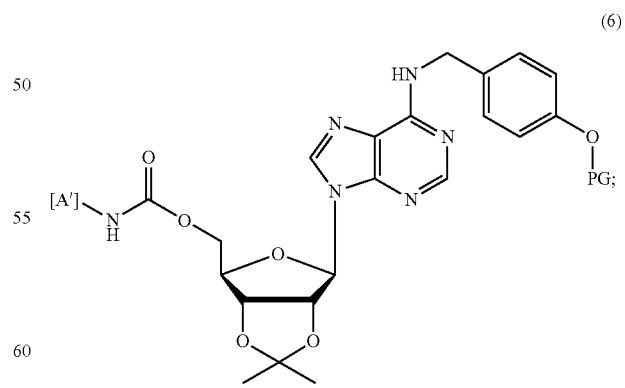

(6)

wherein [A']-NH— is derived from the derivative of amino acid or peptide; and (e) removing all the protecting groups from compound (6) to afford the compound of formula (I);

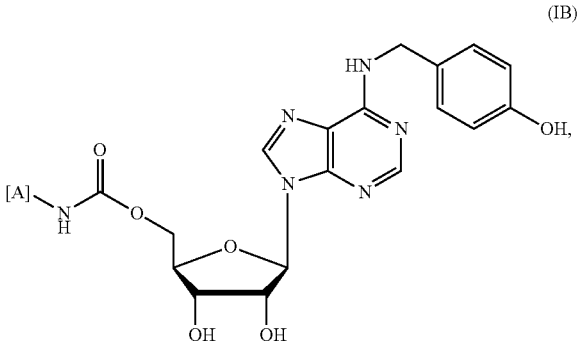

(IB)

wherein [A]-NH— is the amino acid or peptide in the derivative of amino acid or peptide.

In one embodiment of the invention, the acid in step (a) may be p-toluenesulfonic acid or camphorsulfonic acid.

In another embodiment of the invention, the hydroxyl protecting agent (PG-Cl) in step (b) may be 4-methoxybenzyl chloride or benzoyl chloride.

In another embodiment of the invention, the derivative of an amino acid or peptide in step (d) may be glycine methyl ester, glycine ethyl ester, L-phenylalanine ethyl ester, L-valine ethyl ester, γ-aminobutyric acid methyl ester, or undecapeptide Arg-Pro-Lys-Pro-Gln-Gln-Phe-Phe-Gly-Leu-Met-CONH$_2$ (SEQ ID NO:1) (substance P).

In another embodiment of the invention, the deprotecting method in step (e) may comprise using a base to cleave the benzoyl group and using an acid to remove the p-methoxybenzyl group; wherein the base may be lithium hydroxide, sodium hydroxide, potassium hydroxide, cesium carbonate or ammonium hydroxide, and the acid may be trifluoroacetic acid (TFA) or hydrochloric acid.

In another embodiment of the invention, the hydrolysis in step (f) may comprise using a base to remove the alkyl group; wherein the base may be lithium hydroxide, sodium hydroxide, potassium hydroxide, cesium carbonate or ammonium hydroxide.

Further in another embodiment of the invention, the salt of formula (IA) prepared in step (f), wherein $Z^+$ is $Li^+$, $Na^+$, $K^+$, $Rb^+$, $Cs^+$ or $NH_4^+$, is converted to carboxylic acid using a mineral acid, wherein the mineral acid may be hydrochloric acid. R is a substituent existing in common α-amino acids.

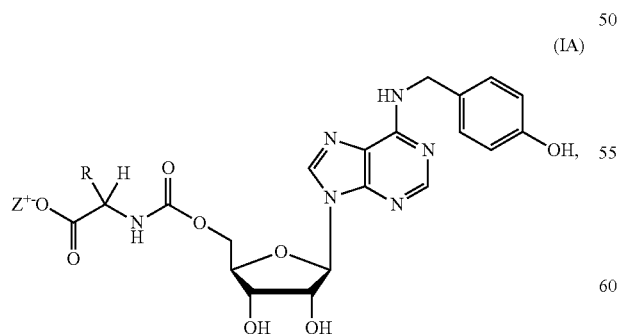

(IA)

Further in another embodiment of the invention, the carboxylic acid of formula (IA, $Z^+=H^+$) is treated with an amine $R^A R^B R^C N$ to form an aminium salt of formula (IA), wherein the amine may be trimethylamine, triethylamine, tri-n-butylamine, benzyldimethylamine, pyrrolidine, piperidine, morpholine, or N-methylmorpholine.

Figure 2:
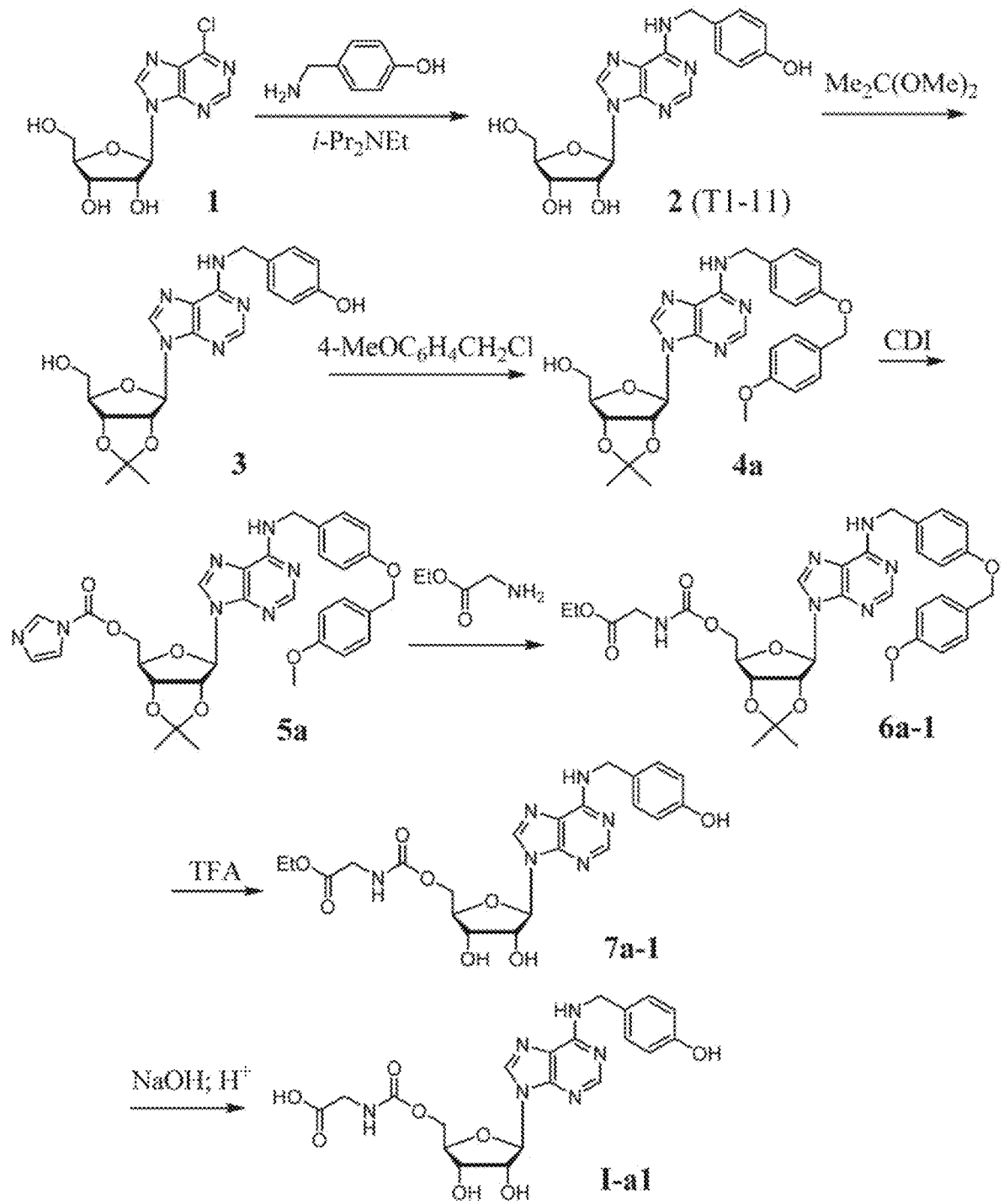

In one approach, compound I-a1 is synthesized via a PMB-protecting intermediate compound 4a as shown in FIG. 2:

(a) According to the previously reported procedure [Chen, J.-B.; Liu, E. M.; Chern, T.-R.; Yang, C.-W.; Lin, C.-I.; Huang, N.-K.; Lin, Y.-L.; Chern, Y.; Lin, J.-H. Fang, J.-M. Design and synthesis of novel dual-action compounds targeting the adenosine $A_{2A}$ receptor and adenosine transporter for neuroprotection. *ChemMedChem* 2011, 6, 1390-1400], T1-11 is obtained from the substitution reaction of 6-chloropurine riboside with 4-hydroxybenzylamine, and treated with 2,2-dimethoxypropane in acetone by catalysis of p-toluenesulfonic acid to afford the acetonide compound 3:

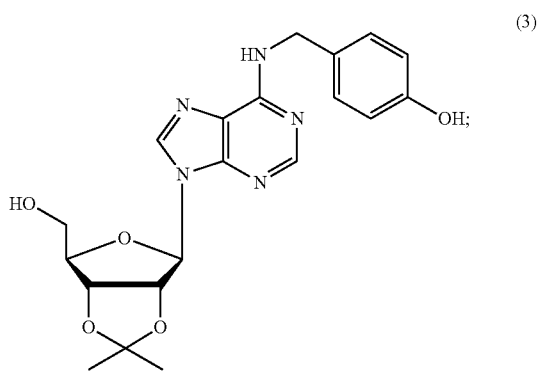

(3)

(b) The phenol group of 3 is protected as a p-methoxybenzyl (PMB) ether by alkylation with 4-methoxybenzyl chloride in the presence of a base $K_2CO_3$, giving compound 4a:

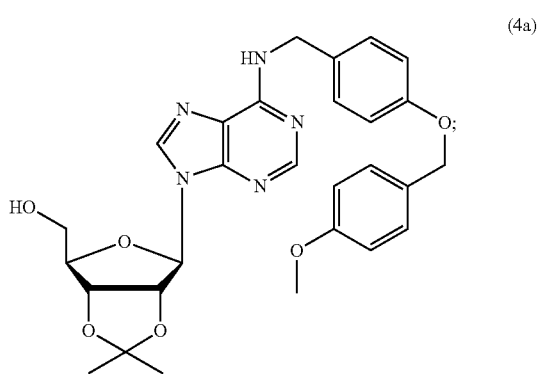

(4a)

(c) The hydroxyl group of 4a is activated by treatment with CDI, giving 5a, which further reacts with glycine ethyl ester to produce the carbamate compound 6a-1:

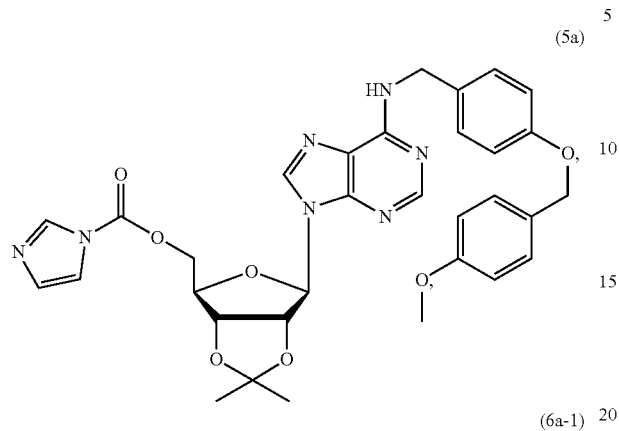

(6a-1)

(d) The acetonide and PMB ether protecting groups of 6a-1 are removed by treatment with trifluoroacetic acid (TFA) to give compound 7a-1, which is hydrolyzed under alkaline conditions to afford compound I-a1 after purification by chromatography:

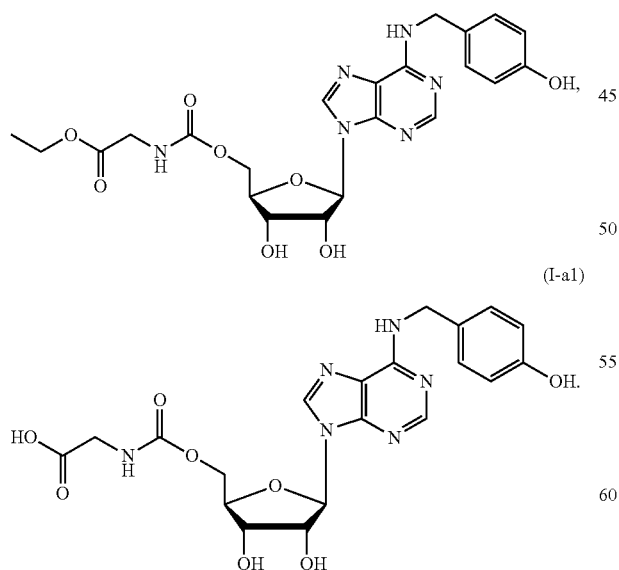

Figure 3:
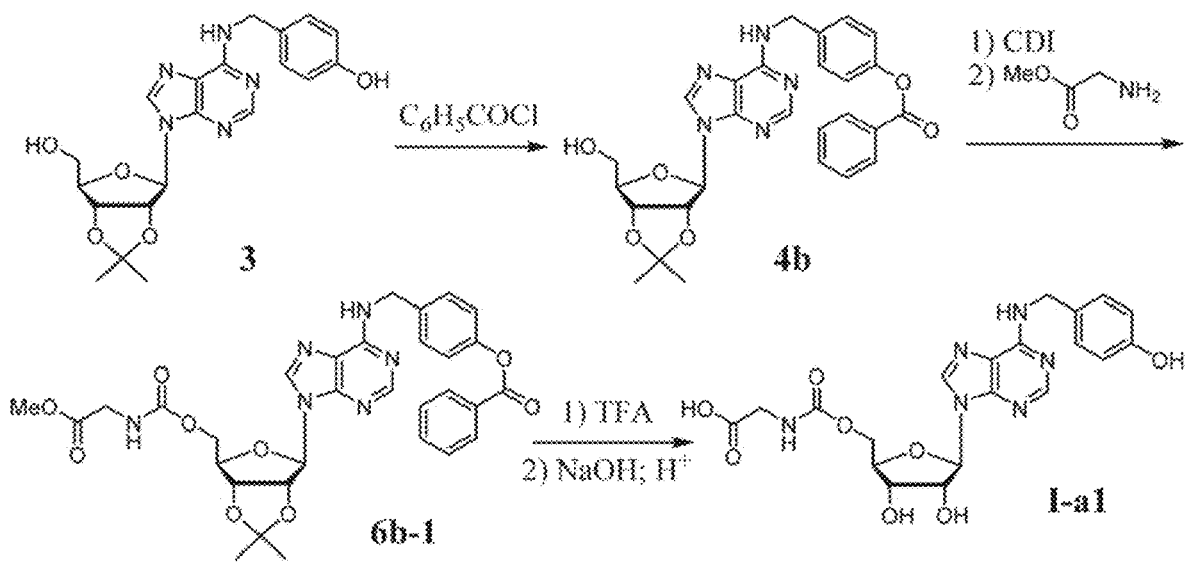
FIG. 3 shows the synthetic method for compound I-a1 via benzoate-protecting intermediate compound 4b.

In another approach, compound I-a1 is synthesized via a benzoate-protecting intermediate compound 4b as shown in FIG. 3.

(a) The phenol group of 3 is protected as a benzoate ester by acylation with benzoyl chloride in the presence of a base $Et_3N$, giving compound 4b:

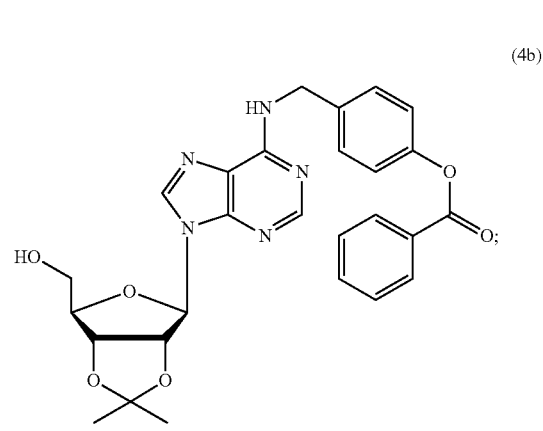

(b) The hydroxyl group of 4b is activated by treatment with CDI, and then reacted with glycine methyl ester to afford the carbamate compound 6b-1:

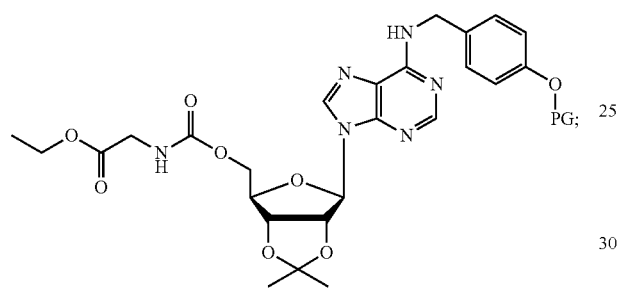

(c) Deprotecting the acetonide and ester groups of 6b-1 produces compound I-a1 after purification by chromatography.

In another embodiment, compound 4a is activated as the imidazolide 5a, which reacts with L-phenylalanine ethyl ester to give compound 6a-2:

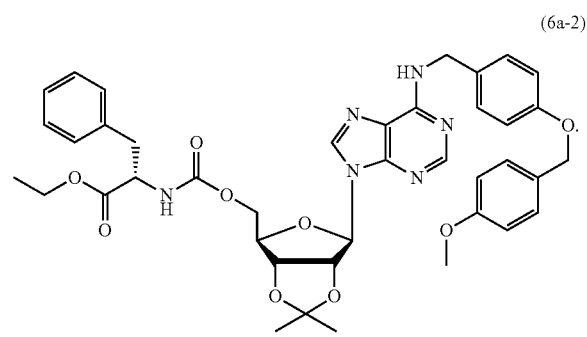

In another embodiment, compound 4b is activated by CDI and then treated with L-valine methyl ester to give compound 6b-2:

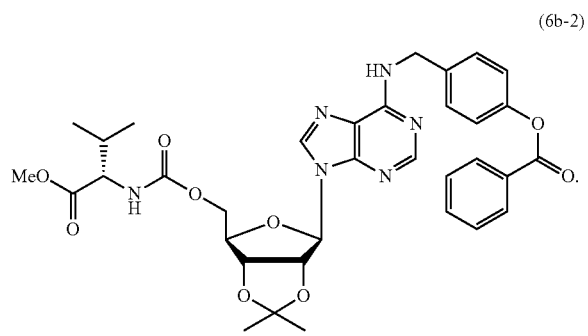

(6b-2)

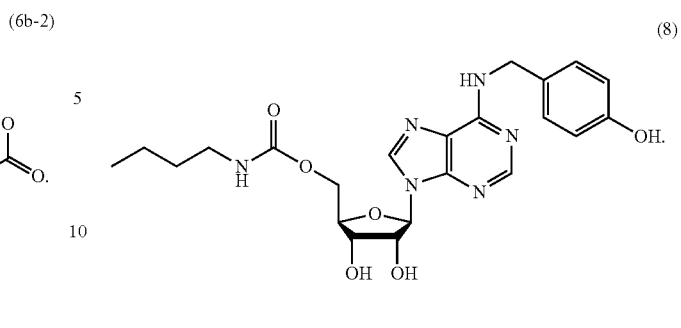

(8)

In another embodiment, compound 6a-2 is treated with TFA, followed by NaOH, to remove the protecting groups to produce compound I-a2:

In another embodiment, the analogous compound Ib-1 containing a terminal carboxylic acid is synthesized via an intermediate compound 9. The imidazolide compound 5a is reacted with γ-aminobutyric acid methyl ester to give compound 9, which is treated with TFA, followed by NaOH, to remove the acetonide, PMB and ester protecting groups to produce compound I-b1:

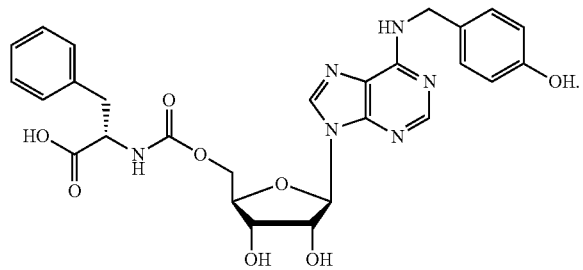

(I-a2)

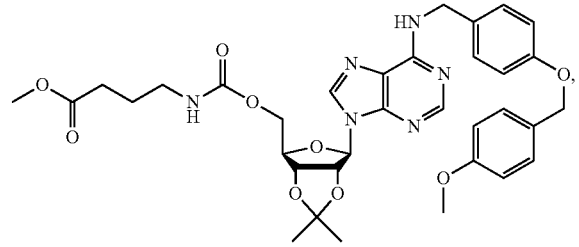

(9)

In another embodiment, compound 6b-2 is treated with TFA, followed by NaOH, to remove the protecting groups to produce compound I-a3:

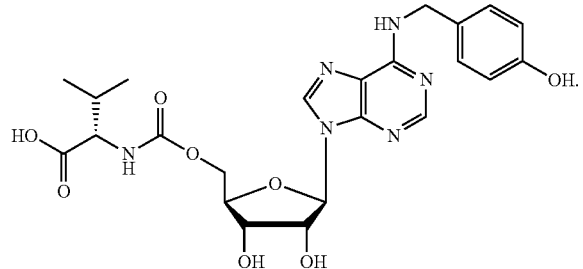

(I-a3)

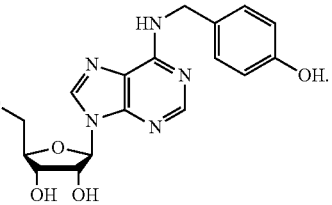

(I-b1)

In one aspect, the analogous compound 8 is synthesized. Compound 4b is activated by CDI and treated with n-butylamine. The product is treated with TFA, followed by NaOH, to remove the acetonide and benzoate protecting groups to produce compound 8:

In another embodiment, compound I-c1 is synthesized via an intermediate compound 10. Compound 6a-1 is hydrolyzed to give the corresponding carboxylic acid, which is subjected to a coupling reaction with L-leucyl-L-methionine amide to form compound 10. Removing the acetonide and PMB protecting groups in 10 by treatment with TFA gives compound I-c1:

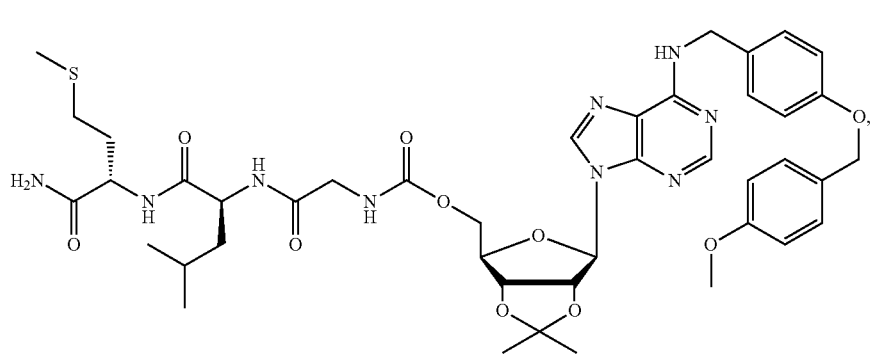

(10)

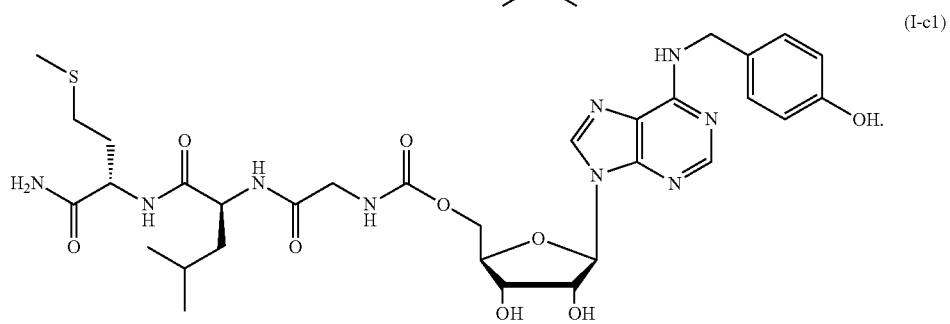

(I-c1)

In another embodiment, compound I-c2 is synthesized by the coupling reaction of imidazolide compound 5a and SP, an undecapeptide Arg-Pro-Lys-Pro-Gln-Gln-Phe-Phe-Gly-Leu-Met-CONH$_2$ (SEQ ID NO:1), followed by treatment with TFA to remove the acetonide and PMB protecting groups:

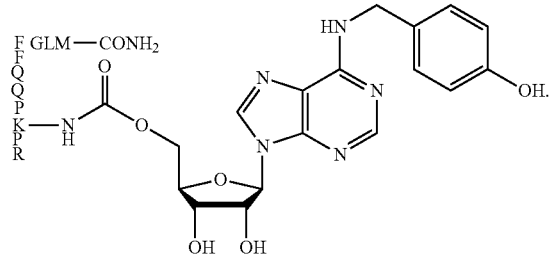

(I-c2)

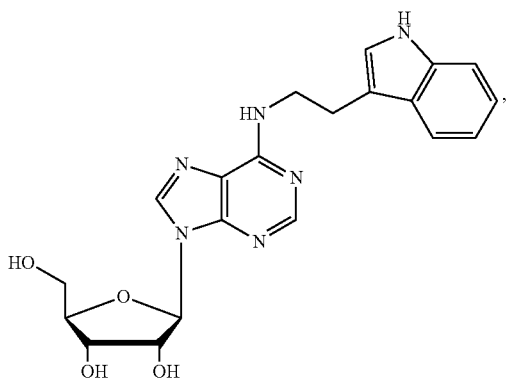

(11)

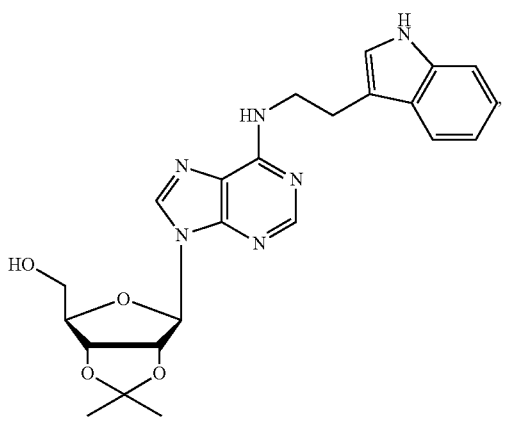

(12)

Figure 4:
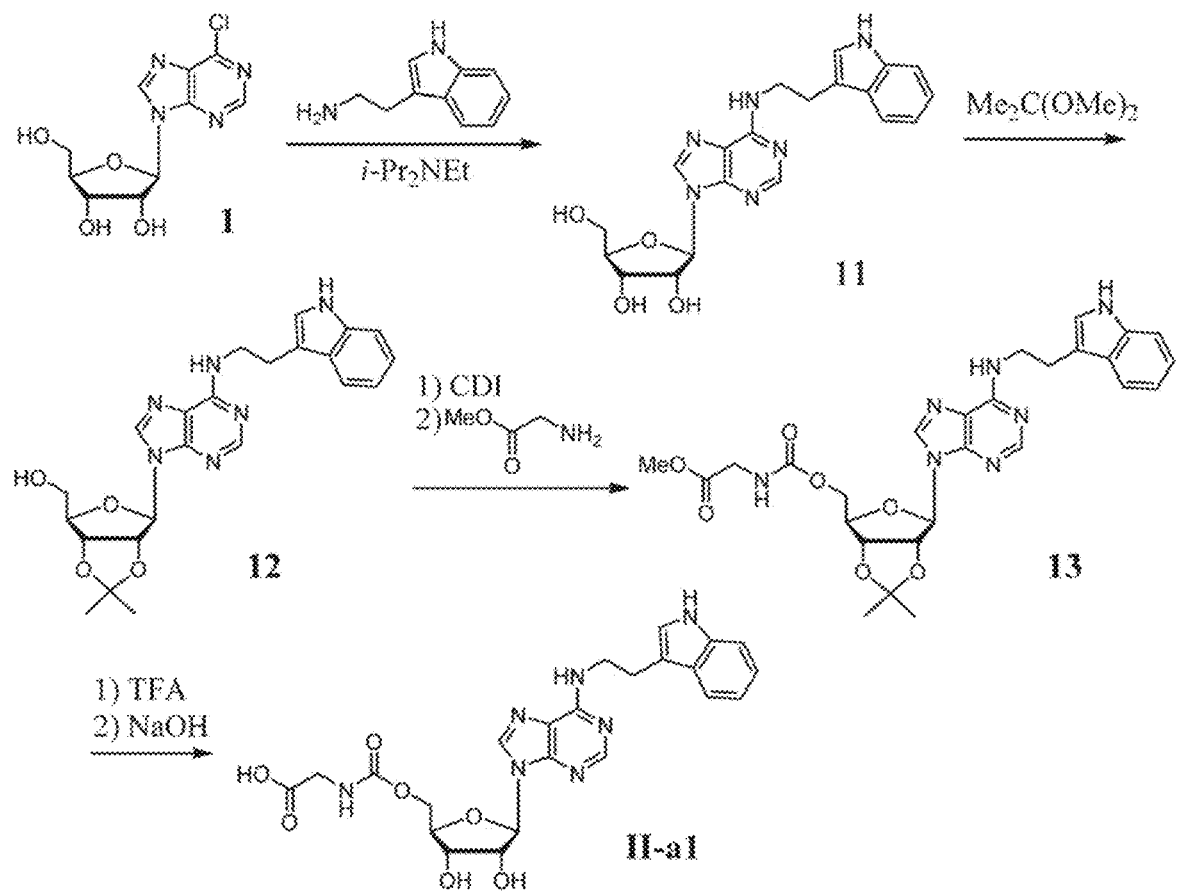
FIG. 4 shows the synthesis of compound II-a1.

In another embodiment, compound of formula II-a1 (14) is an analogous compound of I-a1 by replacement of the N$_6$-(4-hyroxybenzyl) group with an N$_6$-(indol-3-yl)ethyl group. Compound 14 (II-a1) is synthesized from N$^6$-(indol-3-yl)ethyladenosine (compound 11) via the intermediate compounds 12 and 13 as shown in FIG. 4.

-continued

(13)
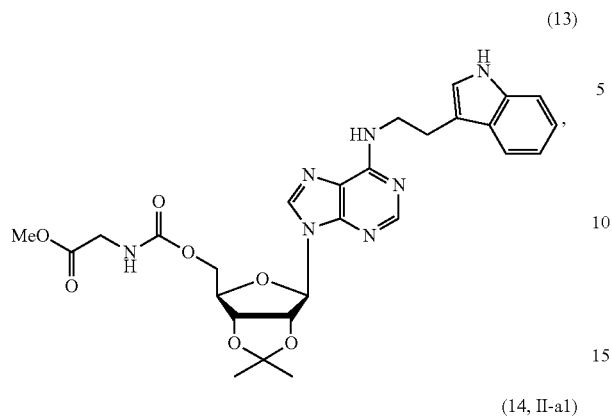

(14, II-a1)
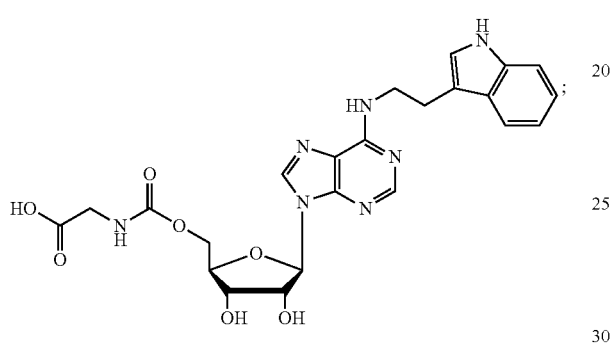

(a) reacting 6-chloropurine riboside (1) with (indol-3-yl)ethylamine in ethanol in the presence of diisopropylethylamine to give N⁶-(indol-3-yl)ethyl-adenosine (11);

(b) reacting compound 11 with 2,2-dimethoxypropane in acetone in the presence of p-toluenesulfonic acid to afford the acetonide compound of formula (12);

(c) activating the hydroxyl group in compound 12 with CDI, followed by reacting with glycine methyl ester to afford the carbamate compound of formula (13); and (d) removing the acetonide protecting group with TFA, followed by hydrolysis in alkaline condition, to afford compound 14 (II-a1).

Figure 5:
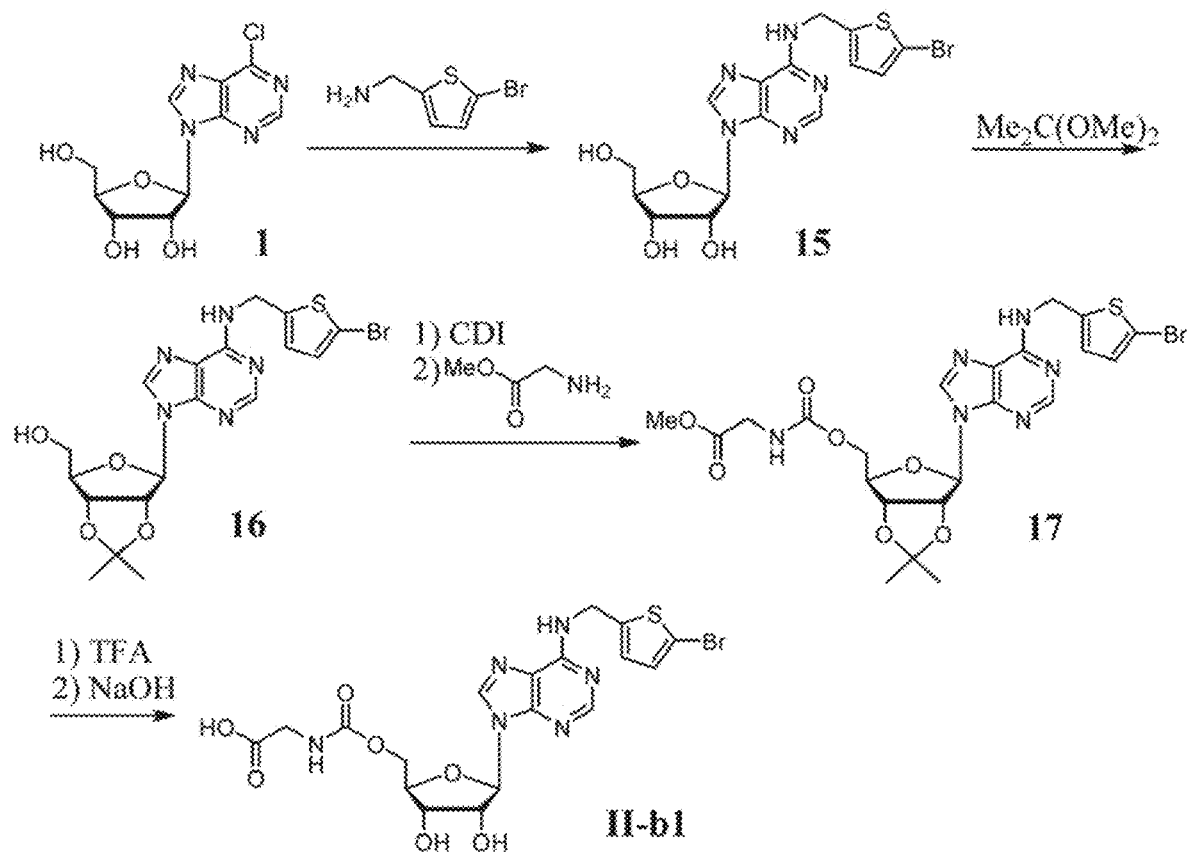
FIG. 5 shows the synthesis of compound II-b1.

In another embodiment, compound of formula II-b1 is an analogous compound of I-a1 by replacement of the N₆-(4-hyroxybenzyl) group with an N₆-(5-bromothien-2-yl)methyl group. Compound II-b1 is synthesized from N⁶-(5-bromothien-2-yl)methyladenosine (compound 15) via the intermediate compounds 16 and 17 as shown in FIG. 5.

(15)
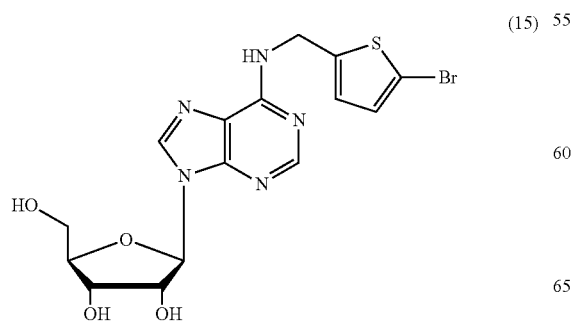

-continued

(16)
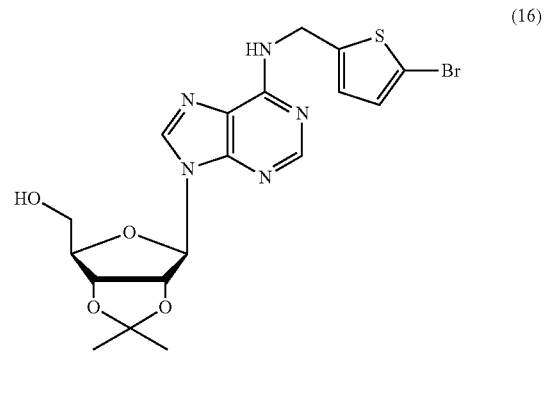

(17)
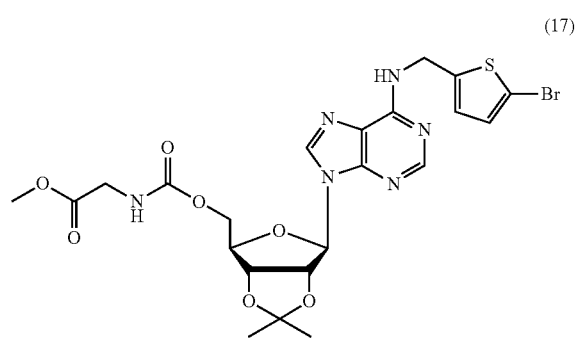

(II-b1)
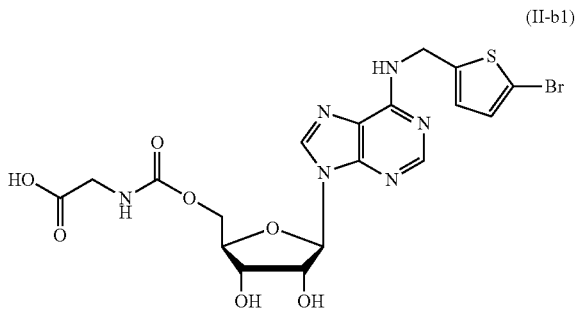

Figure 6:
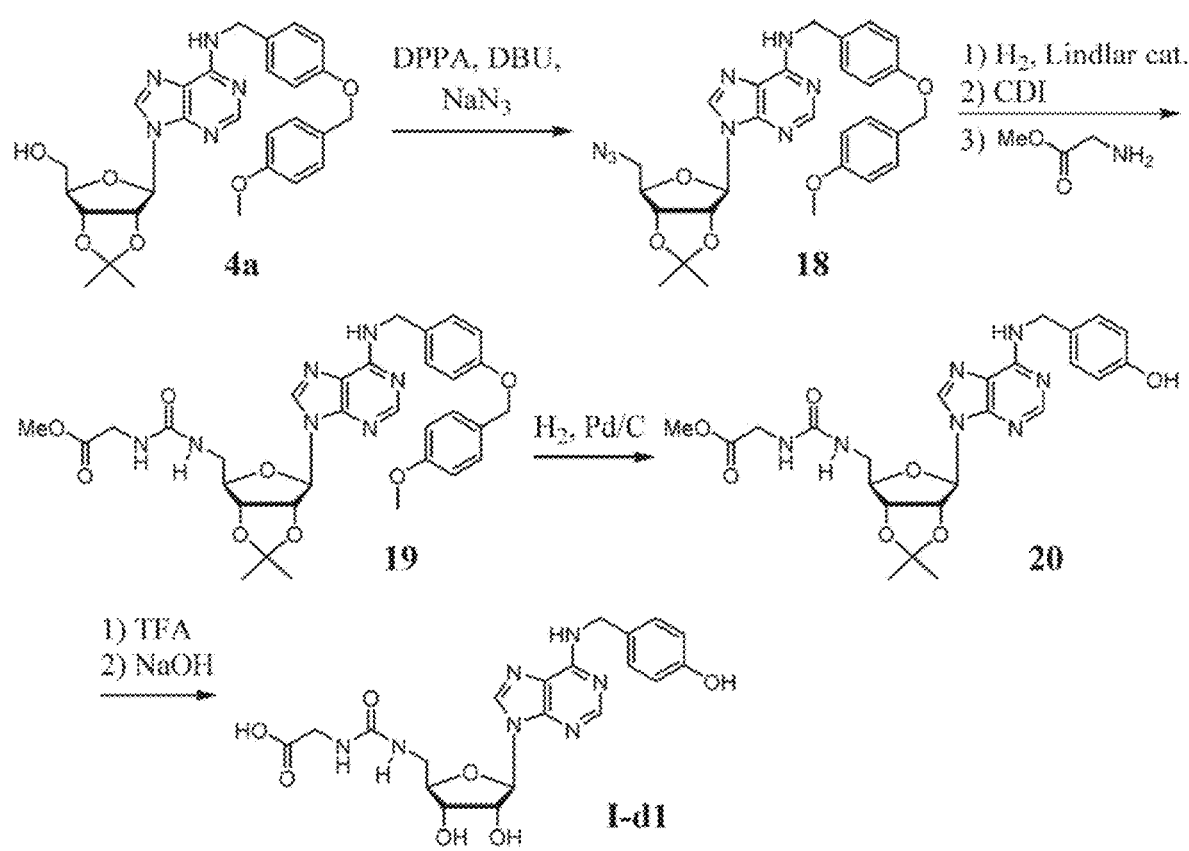
FIG. 6 shows the synthesis of compound I-d1.

In another embodiment, compound I-d1 is synthesized via intermediate compounds 18, 19 and 20 as shown in FIG. 6:

(18)
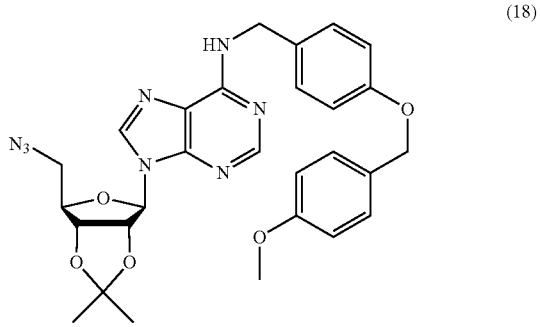

-continued

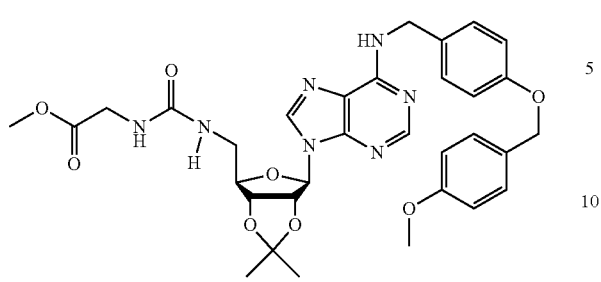

(19)

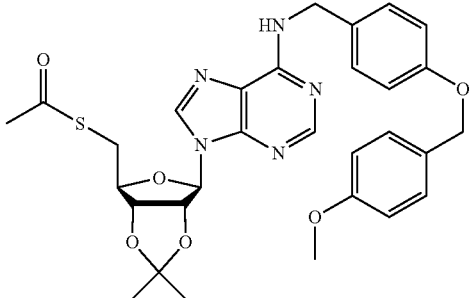

(21)

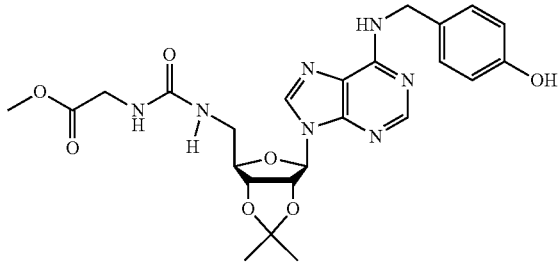

(20)

(22)

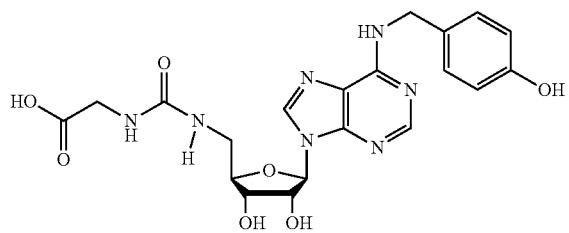

(I-d1)

(I-e1)

(a) reacting compound 4a with diphenyl phosphoryl azide (DPPA) and sodium azide in the presence of a base to afford an azido compound of formula 18, wherein the base may be triethylamine, 4-dimethylaminopyridine (DMAP), 1,4-diazabicyclo[2.2.2]octane (DABCO), 1,5-diazabicyclo[4.3.0]non-5-ene (DBN) and 1,8-diazabicyclo[5.4.0]undec-7-ene (DBU);

(b) reducing the azido compound 18 by hydrogenolysis in the presence of a catalyst, followed by a coupling reaction with a glycine methyl ester hydrochloride in the present of a promoter, to afford a compound of formula 19, wherein the catalyst is Lindlar catalyst and the promoter is 1,1'-carbonyldiimidazole;

(c) removing the PMB protecting groups by hydrogenolysis to afford a compound of formula 20.

(d) removing the protecting groups of 2',3'-diol and ester by TFA and NaOH, respectively, to afford a compound of formula I-d1.

Figure 7:
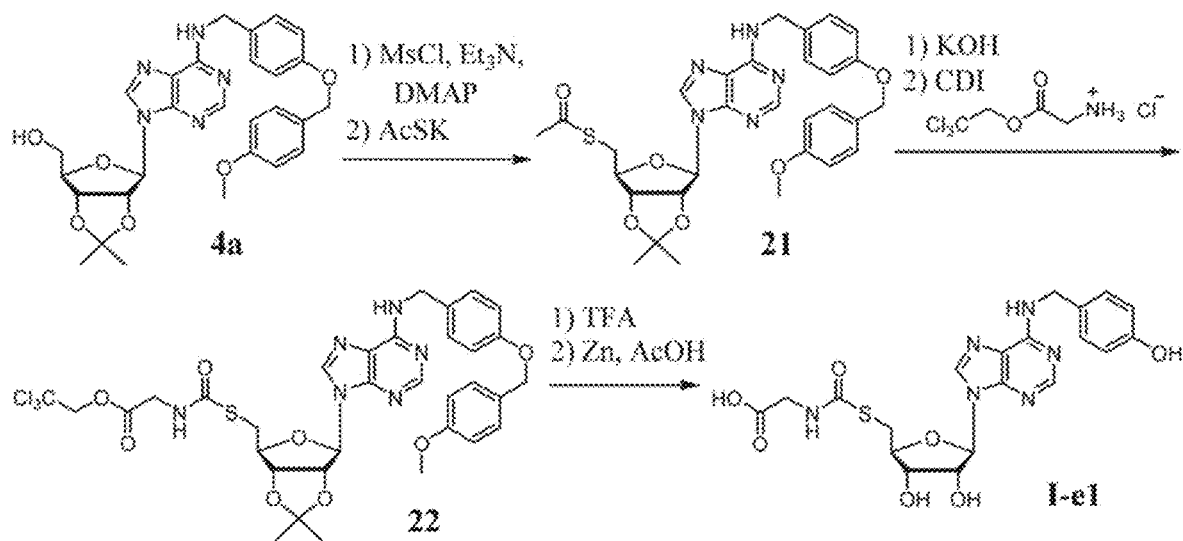
FIG. 7 shows the synthesis of compound I-e1.

In another embodiment, compound I-e1 is synthesized via intermediate compounds 21 and 22 as shown in FIG. 7:

(a) reacting compound 4a with methanesulfonyl chloride (MsCl) in the presence of a base, followed by reacting with potassium thioacetate, to afford a compound of formula 21, wherein the base may be triethylamine and 4-dimethylaminopyridine;

(b) removing the acetyl group from compound 21 with a base, followed by coupling with 2,2,2-trichloroethylglycine in the present of a promoter, to afford a compound of formula 22, wherein the base may be sodium hydroxide and potassium hydroxide, and the promoter is 1,1'-carbonyldiimidazole;

(c) removing all the protecting groups to afford a compound of formula I-e1.

Figure 8:
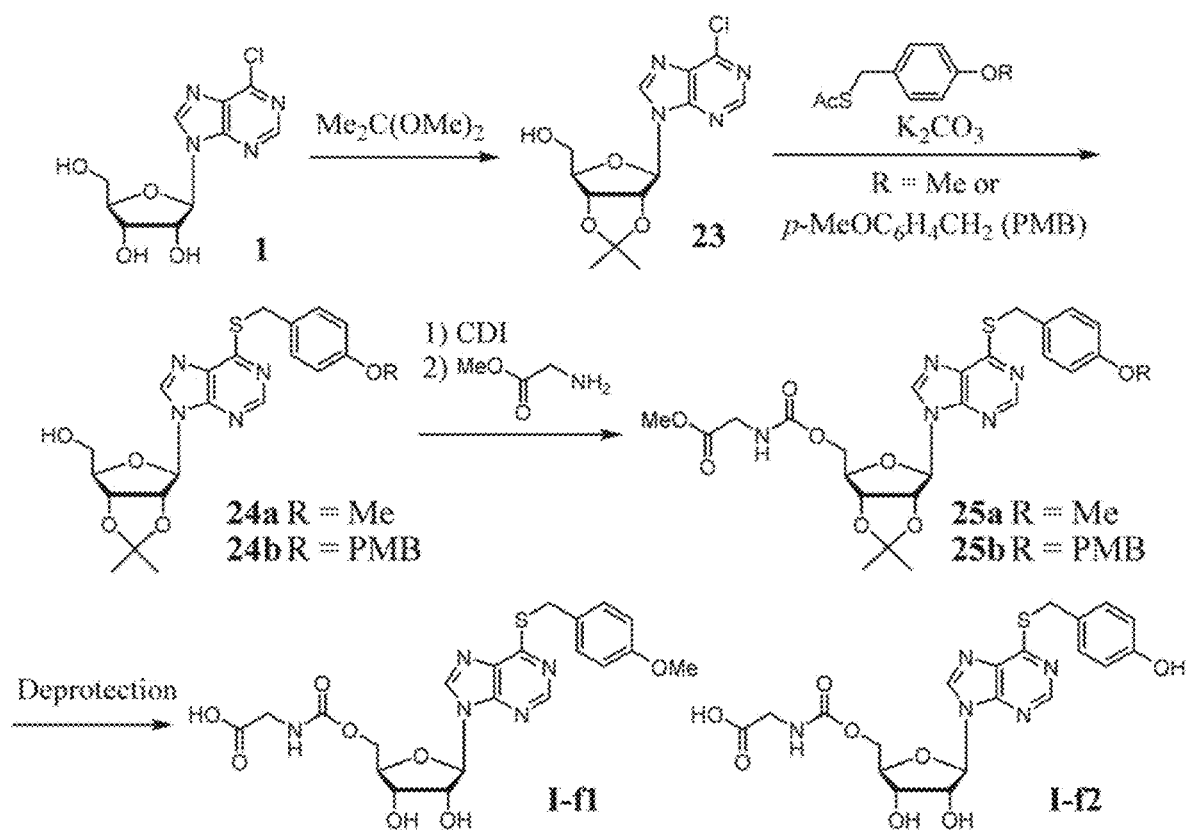
FIG. 8 shows the synthesis of compounds I-f1 and I-f2

In another embodiment, compound I-f1 is synthesized via intermediate compounds 23, 24a and 25a as shown in FIG. 8.

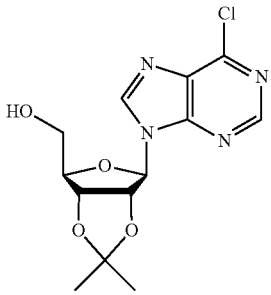

(23)

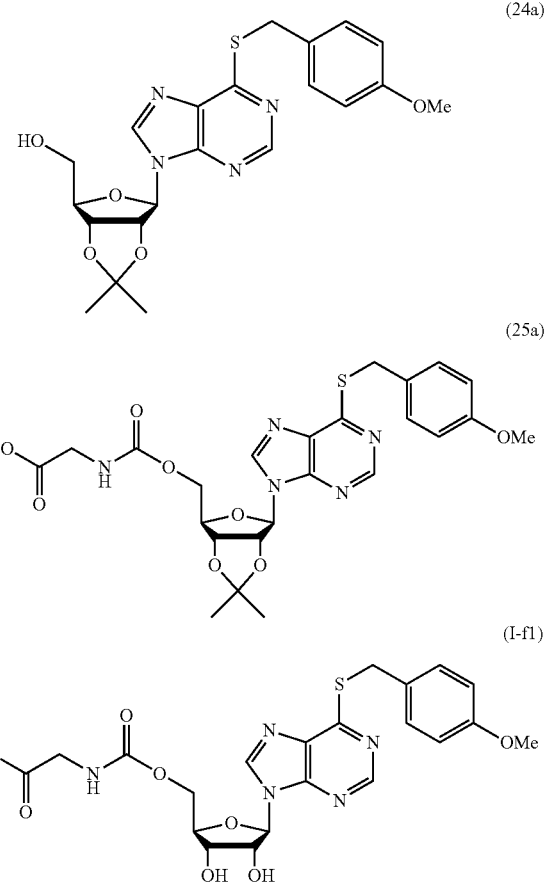

Pharmaceutical Compositions

In another aspect, the invention provides a pharmaceutical composition comprising a compound of the invention and a pharmaceutically acceptable carrier.

The compound may be formulated into pharmaceutical compositions that may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Pharmaceutically acceptable carriers and diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a compound of the invention, diluents, dispersing and surface active agents, binders, and lubricants.

In a preferred embodiment, the compound is present in the composition in an amount that is effective to achieve its intended therapeutic purpose. While individual needs may vary, a determination of optimal ranges of effective amounts of each compound is within the skill of the art.

The compounds of the present invention may be useful in combination with one or more second therapeutic agents, particularly therapeutic agents suitable for the treatment and/or prevention of the conditions and diseases presented herein.

Analgesic Effects

In another aspect, the invention provides a method for treating and/or pain, comprising administering an effective amount of the compound of the invention to a subject. In one embodiment, the pain is chronic pain. In some embodiments, the pain is associated with tissue acidosis and/or nerve injury includes, but is not limited to, inflammatory pain, cancer-associated pain, chest pain, back pain, neck pain, shoulder pain, migraine, headache, myofascial pain, joint pain, muscular pain syndromes, neuropathic pain, peripheral pain, sympathetic pain, postoperative pain, post-traumatic pain, and multiple sclerosis pain. In one embodiment, the pain is dysfunctional pain. In further embodiments, the dysfunctional pain includes, but is not limited to, fibromyalgia, bladder pain syndrome, pain caused by irritable bowel syndrome, and pain associated with temporomandibular disorders.

In one embodiment, compound 2 (T1-11) has good solubility in dimethylsulfoxide (DMSO) and excellent analgesic effect in a mouse model of fibromyalgia, in which chronic widespread pain is induced by intermittent cold stress (ICS). In this ICS mouse model, T1-11 showed dose-dependent analgesic effect with effective dose starting from 0.03 mg/kg via i.p. route (FIG. 9(a)) and 8 mg/kg via p.o. route(FIG. 9(b)). However, T1-11 has a low bioavailability (F≈5%) that may limit its use for treating pain.

In another embodiment, conjugate compound I-a1 (JMF3737) derived from T1-11 and glycine showed superior analgesic effect to that of T1-11. In the same ICS mouse model, compound I-a1 showed dose-dependent analgesic effect with effective dose starting from 1 mg/kg (i.p.) (FIG. 9(c)) and 1 mg/kg (p.o.) (FIG. 9(d)). The doses of compound I-a1 can be increased to at least 64 mg/kg (i.p. and p.o.) without causing appreciable detrimental effect.

In another embodiment, a combined treatment by oral administration of T1-11 (4 μmol/kg) and glycine (4 μmol/kg) showed no synergistic effect (FIG. 9(e)), in comparison with the appreciable analgesic effect of the conjugate compound I-a1 at 2 mg (4 μmol)/kg via oral route.

Figure 10:
FIG. 10 shows the analgesic mechanism of action of compound I-a1 (JMF3737); the concentration of RP67580 and JMF3737 is each 10 μM.
Figure 10:
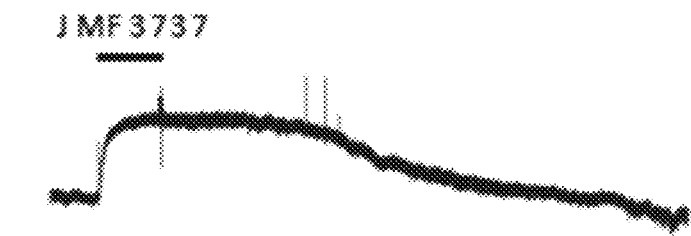
Figure 10:
Figure 10:
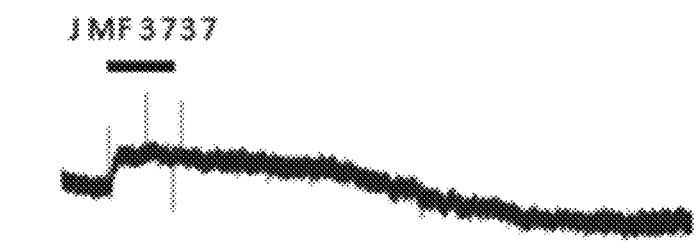
Figure 10:
Figure 10:
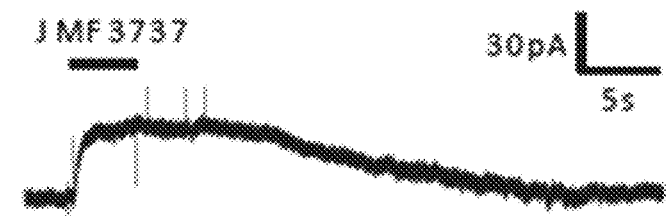

In another embodiment, the analgesic mechanism of action of compound I-a1 (JMF3737) is the same as T1-11 by acting on the NK1R receptor in muscle nociceptors to induce an outward current that can be inhibited by NK1R antagonist (FIG. 10).

Figure 11:
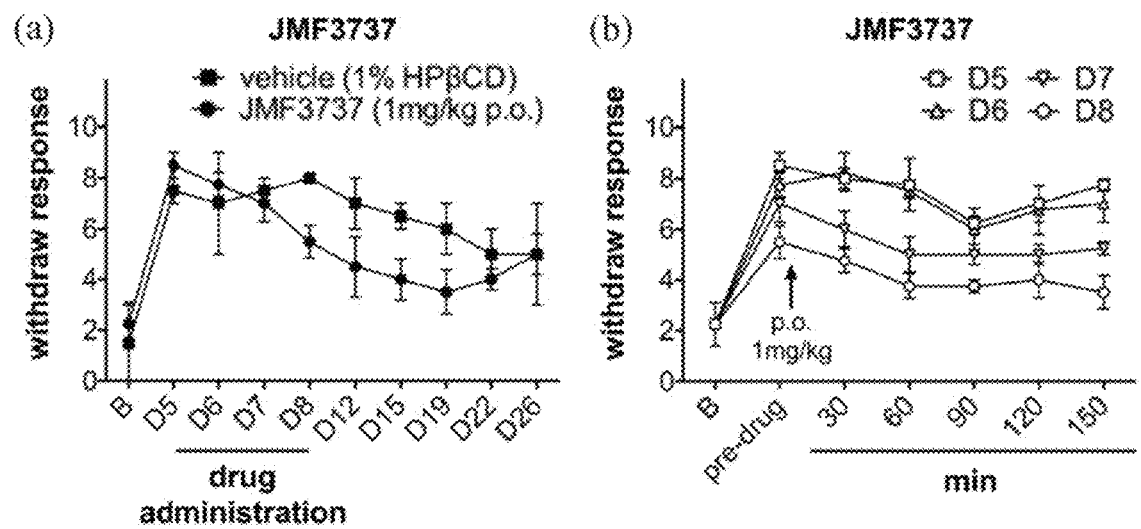
FIG. 11 shows no tolerance but therapeutic effect on repeated treatment of compound I-a1 (JMF3737).

In another embodiment, daily treatment of compound I-a1 (JMF3737) in low dose (1 mg/kg, p.o.) for 4 days showed no tolerance but therapeutic effect for fibromyalgia pain (FIGS. 11(a) and 11(b)).

Figure 12:
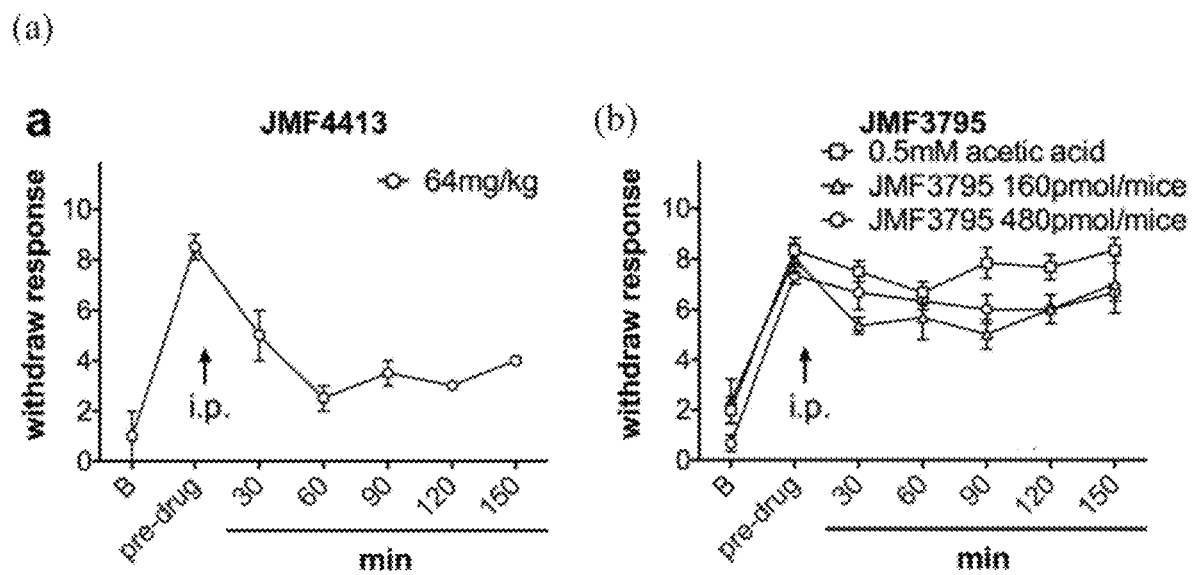
FIG. 12 illustrates the analgesic effects of JMF4413 and JMF3795 in a mouse model of fibromyalgia, in which chronic widespread pain was induced by intermittent cold stress (ICS).

Further in another embodiment, compound I-d1 (JMF4313) showed excellent analgesic effect in the same ICS model (FIG. 12(a)). The dose of compound I-d1 can be increased to 64 mg/kg (i.p.) without causing appreciable detrimental effect.

Further in another embodiment, a conjugate compound Ic-2 derived from T1-11 and substance P showed analgesic effect starting from 14 μg/kg (160 pmol, i.p.) in the ICS mouse model (FIG. 12(b)).

EXAMPLES

All reagents and solvents were of reagents grade and were used without further purification unless otherwise specified. Tetrahydrofuran and diethyl ether were distilled from Na/benzophenone and $CH_2Cl_2$ was distilled from $CaH_2$. All air or moisture sensitive experiments were performed under argon. All glasses were dried in an oven for more than 2 hours and used after cooling to room temperature in desiccators.

Melting points were recorded on a Yanaco micro apparatus. Optical rotations were measured on digital polarimeter of Japan JASCO Co. DIP-1000. $[\alpha]_D$ values are given in units of $10^{-1}$deg cm$^2$ g$^{-1}$. Infrared (IR) spectra were recorded on Nicolet Magna 550-II. NMR spectra were obtained on Varian Unity Plus-400 (400 MHz) and chemical shifts ($\delta$) were recorded in parts per million (ppm) relative to $\delta_H$ 7.24/$\delta_C$ 77.0 (central line of triplet) for CHCl$_3$/CDCl$_3$, $\delta_H$ 2.05/$\delta_C$ 29.92 for (CH$_3$)$_2$CO/(CD$_3$)$_2$CO, $\delta_H$ 3.31/$\delta_C$ 49.0 for CH$_3$OH/CD$_3$OD, and $\delta_H$ 2.49 (m)/$\delta_C$ 39.5 (m) for (CH$_3$)$_2$SO/(CD$_3$)$_2$SO. The splitting patterns are reported as s (singlet), d (doublet), t (triplet), q (quartet), m (multiplet) and br (broad). Coupling constants (J) are given in Hz. The ESI-MS experiments were conducted on a Bruker Daltonics BioTOF III high-resolution mass spectrometer. Analytical thin-layer chromatography (TLC) was performed on E. Merck silica gel 60 F$_{254}$ plates (0.25 mm). Compounds were visualized by UV, anisaldehyde or ninhydrin spray. Column chromatography was carried out on columns packed with 70-230 mesh silica gel.

$N^6$-(4-Hydroxybenzyl)-2',3'-O-isopropylidene-adenosine (3)

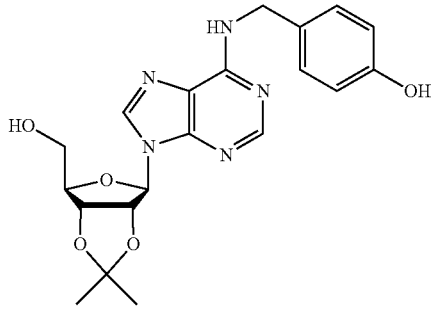

(3)

$N^6$-(4-Hydroxybenzyl)adenosine (compound 2, T1-11) was prepared from the substitution reaction of 6-chloropurine riboside with 4-hydroxybenzylamine according to the previously reported procedure [Chen et al., 2011.]. In brief, a mixture of 4-hydroxybenzylamine (as the hydrochloric salt, 2.5 equiv), 6-chloropurine riboside (1 equiv), and diisopropylethylamine (DIEA, 24 equiv) in 1-propanol was heated to 70° C. for 6 h. The mixture was concentrated under reduced pressure, and triturated with water to give white precipitates, which were filtered to yield compound 2 (81% yield).

A mixture of compound 2 (374 mg, 1 mmol), p-toluenesulfonic acid monohydrate (280 mg, 1.5 mmol) and 2,2-dimethoxypropane (3 mL, 2.5 mmol) in acetone (5 mL) was stirred at room temperature for 4 h. The mixture was concentrated by rotary evaporation under reduced pressure. The residue was diluted with CH$_2$Cl$_2$, extracted with water. The water phase was washed with CH$_2$Cl$_2$, and the combined organic layers were washed with saturated NaHCO$_{3(aq.)}$ and brine successively. The organic phase was dried over MgSO$_4$, filtered, concentrated by rotatory evaporation under reduced pressure, and purified by column chromatography (silica gel, hexane/EtOAc, gradients from 1:1 to 0:1) to give the acetonide compound 3 (358 mg, 86% yield). C$_{20}$H$_{23}$N$_5$O$_5$; TLC (EtOAc) R$_f$=0.56; $[\alpha]_D^{25}$=−113.1 (CHCl$_3$, c=2); IR $\nu_{max}$ (neat) 3367, 2991, 2933, 1622, 1516, 1454, 1381, 1340, 1217, 1082 cm$^{-1}$; $^1$H NMR (CDCl$_3$, 400 MHz) $\delta$ 8.35 (1 H, br s), 7.81 (1 H, s), 7.04 (2H, d, J=8.0 Hz), 6.64 (2H, d, J=8.0 Hz), 6.39 (1 H, br s), 5.82 (1H, d, J=5.2 Hz), 5.19 (1H, dd, J=5.6, 5.2 Hz), 5.10 (1H, d, J=5.6 Hz), 4.67 (2 H, br s), 4.53 (1 H, s), 3.93-4.02 (1H, m), 3.71-3.82 (1H, m), 1.62 (3 H, s), 1.36 (3 H, s); $^{13}$C NMR (CDCl$_3$, 100 MHz) $\delta$ 155.8, 154.5, 153.9, 147.1, 139.4, 129.1, 129.0, 120.4, 115.5, 114.0, 94.1, 86.0, 83.0, 81.6, 63.2, 44.0, 27.5, 25.1; ESI-HRMS calcd for C$_{20}$H$_{24}$N$_5$O$_5$: 414.1777, found: m/z 414.1763 [M+H]$^+$.

2',3'-O-Isopropylidene-$N^6$-(4-(4-methoxybenyloxy)benzyl)adenosine (4a)

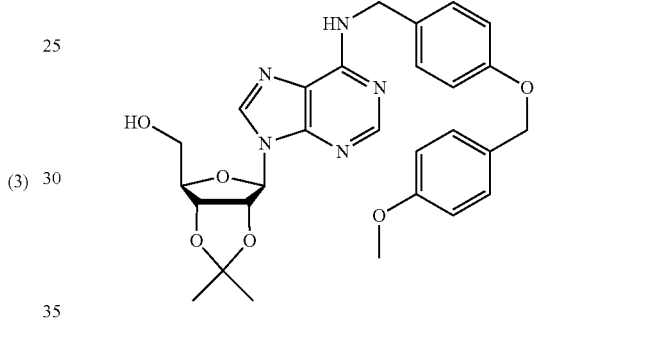

(4a)

A mixture of compound 3 (1.13 g, 2.74 mmol), p-methoxybenzyl chloride (800 μL, 6 mmol) and K$_2$CO$_3$ (930 mg, 6.85 mmol) in N,N-dimethylformamide (DMF, 25 mL) was stirred at 45° C. for 3 h. The mixture was concentrated by rotary evaporation under reduced pressure. The residue was diluted with EtOAc, and washed with 1 M HCl, water and brine successively. The organic phase was dried over MgSO$_4$, filtered, concentrated by rotatory evaporation, and purified by column chromatography (silica gel, EtOAc/hexane, gradients from 1:3 to 4:1) to give the PMB derivative 4a (1.12 g, 76% yield). C$_{28}$H$_{31}$N$_5$O$_6$; white solid; mp 68.3-71.4° C.; TLC (EtOAc/hexane (1:1)) R$_f$=0.17; $[\alpha]_D^{25}$=−66.0 (CH$_2$Cl$_2$, c=2); IR $\nu_{max}$ (neat) 3281, 2988, 2936, 2870, 2834, 1622, 1586, 1514, 1478, 1468, 1380, 1339, 1303, 1242, 1216, 1170, 1154, 1113, 1077 cm$^{-1}$; $^1$H NMR (CDCl$_3$, 400 MHz) $\delta$ 8.34 (1 H, br s), 7.66 (1 H, br s), 7.32 (2H, d, J=8.4 Hz), 7.25 (2H, d, J=8.4 Hz), 6.89 (4 H, dd, J=8.4, 5.8 Hz), 6.77 (1 H, br s), 6.42 (1 H, br s), 5.79 (1H, d, J=4.8 Hz), 5.18 (1H, t, J=5.2 Hz), 5.09 (1H, d, J=5.6 Hz), 4.95 (2 H, s), 4.73 (2 H, br s), 4.51 (1 H, s), 3.95 (1H, d, J=12.46 Hz), 3.71-3.83 (4H, m), 1.62 (3 H, s), 1.35 (3 H, s); $^{13}$C NMR (CDCl$_3$, 100 MHz) $\delta$ 159.3, 158.3, 154.9, 152.7, 147.3, 139.5, 130.2, 129.1, 129.0, 128.8, 121.2, 115.0, 114.0, 113.9, 94.3, 85.9, 82.9, 81.7, 69.7, 63.4, 55.2, 43.9, 27.6, 25.2; ESI-HRMS calcd. for C$_{28}$H$_{32}$N$_5$O$_6$: 534.2353, found: m/z 534.2368 [M+H]$^+$.

$N^6$-(4-(Bezoyloxy)benzyl)-2',3'-O-isopropylidene-adenosine (4b)

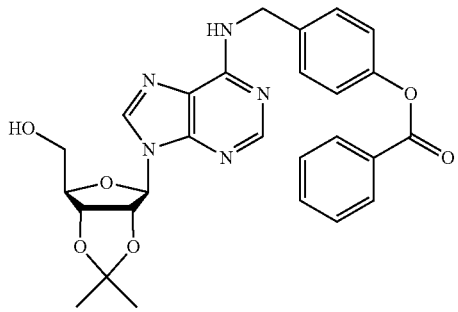

A mixture of compound 2 (265 mg, 0.64 mmol) and $NEt_3$ (267 μL, 1.9 mmol) in $CH_2Cl_2$ (15 mL) was stirred at 0° C. while a solution of benzoyl chloride (74 μL, 0.64 mmol) in $CH_2Cl_2$ (9 mL) was added via syringed pump (4 mL/h). After the addition was complete, the mixture was concentrated by rotary evaporation under reduced pressure. The residue was diluted with EtOAc, and washed with 1 M HCl, saturated $NaHCO_3$, water and brine successively. The organic phase was dried over $MgSO_4$, filtered, concentrated by rotary evaporation, and purified by column chromatography (silica gel, hexane/EtOAc, gradients from 1:1 to 0:1) to give compound 4b (258 g, 78% yield). $C_{27}H_{27}N_5O_6$; white foam; TLC (EtOAc/hexane (1:1)) $R_f$=0.13; $[\alpha]_D^{25}$=−74.4 ($CHCl_3$, c=2); IR $v_{max}$ (neat) 3279, 2989, 2934, 2860, 1735, 1622, 1508, 1481, 1357, 1340, 1265, 1202, 1081, 1065 cm$^{-1}$; $^1$H NMR ($CDCl_3$, 400 MHz) δ 8.33 (1 H, br s), 8.15 (2H, d, J=7.6 Hz), 7.57 (1 H, t, J=7.6 Hz), 7.45 ([[3]]2 H, t, J=7.6 Hz), 7.35 (3H, d, J=8.0 Hz), 7.12 (2H, d, J=8.0 Hz), 6.63 (1 H, br s), 5.82 (1H, d, J=4.8 Hz), 5.17 (1H, dd, J=5.2, 4.8 Hz), 5.06 (1H, d, J=5.2 Hz), 4.81 (2 H, d, J=18.8 Hz), 4.46 (1 H, s), 3.91 (1H, d, J=12.0 Hz), 3.73 (1H, d, J=12.0 Hz), 1.57 (3 H, s), 1.31 (3 H, s); $^{13}$C NMR ($CDCl_3$, 100 MHz) δ 165., 154.9, 152.6, 150.0, 147.3, 139.6, 136.0, 133.5, 130.0, 129.2, 128.6, 128.4, 121.8, 120.9, 113.7, 93.9, 85.9, 82.9, 81.5, 63.2, 43.4, 27.4, 25.1; ESI-HRMS calcd. for $C_{27}H_{28}N_5O_6$: 518.2040, found: m/z 518.2050 [M+H]$^+$.

5'-O-(Imidazolyl-N-carbonyl)-2',3'-O-isopropylidene-$N^6$-(4-(4-methoxybenzyloxy)benzyl)adenosine (5a)

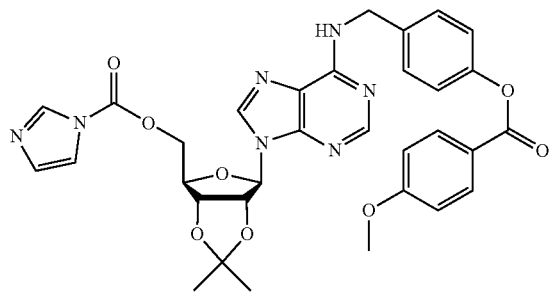

A mixture of compound 4a (207 mg, 0.38 mmol), 4-dimethylaminopyridine (DMAP, catalytic amount) and 1,1'-carbonyldiimidazole (500 mg, 3.1 mmol) in anhydrous $CH_2Cl_2$ (3 mL) was stirred at room temperature under argon for 3 h. After the reaction was complete (monitored by TLC), the mixture was washed with 1 M HCl, water and brine successively. The organic phase was dried over $MgSO_4$, filtered, and concentrated by rotatory evaporation to give compound 5a (241 mg, 98% yield).

$C_{32}H_{33}N_7O_7$; white powder; mp 68.3-71.5° C.; TLC (EtOAc/hexane (1:1)) $R_f$=0.34; $[\alpha]_D^{25}$ 2.36 ($CH_2Cl_2$, c=2); IR $v_{max}$ (neat) 3281, 3134, 3035, 2995, 2929, 2835, 1769, 1617, 1585, 1151, 1482, 1409, 1389, 1295, 1242, 1176, 1102, 1004 cm$^{-1}$; $^1$H NMR ($CDCl_3$, 400 MHz) δ 8.32 (1 H, br s), 8.11 (1H, s), 7.71 (1H, s), 7.37 (1 H, s), 7.32 (2H, d, J=8.8 Hz), 7.27 (2H, d, J=8.4 Hz), 7.02 (1 H, s), 6.89 (4H, t, J=8.0 Hz), 6.26 (1 H, br s), 6.02 (1H, d, J=1.6 Hz), 5.53 (1H, dd, J=6.4, 1.6 Hz), 5.22 (1H, dd, J=6.4, 4.0 Hz), 4.95 (2 H, s), 4.74 (1 H, br s), 4.68 (1H, dd, J=11.2, 4.0 Hz), 4.54-4.62 (1H, m), 4.46-4.54 (1H, m), 3.78 (3H, s), 1.60 (3H, s), 1.38 (3 H, s); $^{13}$C NMR ($CDCl_3$, 100 MHz) δ 159.2, 158.1, 154.5, 148.1, 140.9, 139.4, 139.3, 137.0, 134.0, 13.5, 13.3, 129.0, 128.9, 128.7, 117.0, 115.0, 114.7, 113.9, 90.8, 84.6, 83.8, 81.4, 69.8, 67.2, 55.3, 39.0, 27.3; ESI-HRMS calcd. for $C_{32}H_{34}N_7O_7$: 628.2520, found: m/z 628.2514 [M+H]$^+$.

5'-O((Ethyl glycinate)-N-carbonyl)-2',3'-O-isopropylidene-$N^6$-(4-(4-methoxybenzyloxy)benzyl)adenosine (6a-1)

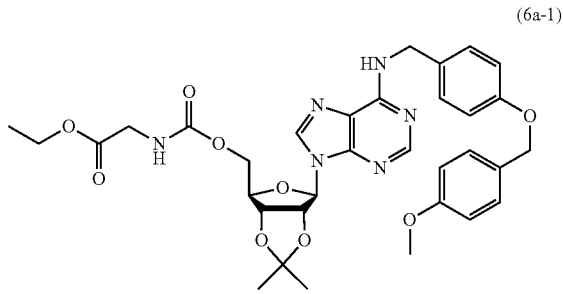

A mixture of compound 5a (104 mg, 0.16 mmol), DMAP (catalytic amount), DIEA (110 μL, 0.64 mmol) and glycine ethyl ester hydrochloride (93 mg, 0.66 mmol) in DMF (4 mL) was stirred at room temperature under argon for 12 h. After the reaction was complete (monitored by TLC), the mixture was concentrated by rotary evaporation under reduced pressure. The residue was diluted with EtOAc and washed with 1 M HCl, saturated $NaHCO_3$, water and brine successively. The organic phase was dried over $MgSO_4$, filtered, concentrated by rotary evaporation, and purified by column chromatography (silica gel, EtOAc/hexane, gradients from 1:3 to 9:1) to give compound 6a-1 (104 mg, 94% yield). $C_{33}H_{38}N_6O_9$; white solid; mp 69.6-71.2° C.; $[\alpha]_D^{25}$=−25.5 ($CH_2Cl_2$, c=2); IR $v_{max}$ (neat) 3367, 2987, 5938, 2835, 1724, 1618, 1581, 1511, 1483, 1466, 1381, 1303, 1246, 1217, 1172, 1078, 1029 cm$^{-1}$; $^1$H NMR ($CDCl_3$, 400 MHz) δ 8.36 (1 H, br s), 7.78 (1 H, s), 7.31 (2H, d, J=8.4 Hz), 7.25 (2 H, d, J=8.4 Hz), 6.88 (2H, d, J=8.4 Hz), 6.87 (2H, d, J=8.4 Hz), 6.57 (1H, t, J=5.3 Hz), 6.05 (1 H, s), 5.81 (1 H, br s), 5.35 (1H, d, J=4.8 Hz), 4.97 (1H, dd, J=6.0, 3.2 Hz), 4.93 (2 H, s), 4.74 (2 H, br s), 4.38-4.44 (1H, m), 4.32 (1H, dd, J=11.6, 4.0 Hz), 4.08-4.20 (3H, m), 3.79-3.96 (2H, m), 3.77 (3H, s), 1.57 (3H, s), 1.34 (3 H, s), 1.22 (4H, t, J=7.2 Hz); $^{13}$C NMR (CDCl$_3$, 100 MHz) δ 169.9, 159.3, 158.1, 155.7, 154.6, 153.3, 148.3, 139.1, 130.7, 129.1, 129.0, 128.8, 120.1, 114.9, 114.3, 113.9, 90.7, 85.0, 84.0, 81.5, 69.7, 64.7, 61.4, 55.2, 43.8, 42.7, 27.0, 25.2, 14.0; ESI-HRMS calcd. for C$_{33}$H$_{39}$N$_6$O$_9$: 663.2779, found: m/z 663.2772 [M+H]$^+$.

5'-O-(Ethyl L-phenylalaninate)-N-carbonyl)-2',3'-O-isopropylidene-N$^6$-(4-(4-methoxybenzyloxy)benzyl) adenosine (6a-2)

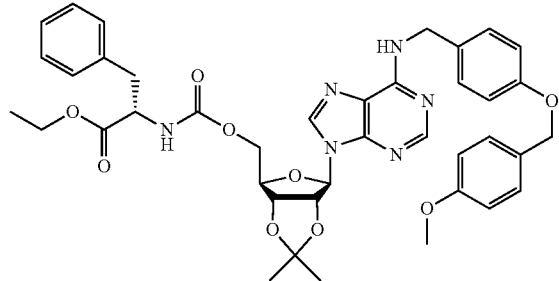
(6a-2)

A mixture of compound 5a (110 mg, 0.17 mmol), DMAP (catalytic amount), DIEA (125 μL, 0.68 mmol) and L-phenylalanine ethyl ester hydrochloride (160 mg, 0.68 mmol) in anhydrous DMF (13 mL) was stirred at room temperature under argon for 12 h. After the reaction was complete (monitored by TLC), the mixture was concentrated by rotary evaporation under reduced pressure. The residue was diluted with EtOAc, and washed with 1 M HCl, saturated NaHCO$_3$, water and brine successively. The organic phase was dried over MgSO$_4$, filtered, concentrated by rotatory evaporation under reduced pressure, and purified by column chromatography (silica gel, EtOAc/hexane, gradients from 1:3 to 9:1) to give compound 6a-2 (44 mg, 34% yield). C$_{40}$H$_{44}$N$_6$O$_9$; white solid; mp 80.1-83.6° C.; TLC (EtOAc) R$_f$=0.75; [α]$_D^{25}$=−9.55 (CH$_2$Cl$_2$, c=1); IR ν$_{max}$ (neat) 3371, 3028, 2991, 2942, 2876, 2844, 1728, 1621, 1585, 1512, 1489, 1463, 1377, 1344, 1299, 1250, 1209, 1176, 1082, 1033 cm$^{-1}$; $^1$H NMR (CDCl$_3$, 400 MHz) δ 8.36 (1 H, br s), 7.76 (1 H, s), 7.32 (2H, d, J=8.4 Hz), 7.26 (2H, d, J=8.4 Hz), 7.15-7.22 (3H, m), 7.04 (2H, d, J=6.6 Hz), 6.89 (2 H, d, J=8.4 Hz), 6.88 (2H, d, J=8.4 Hz), 6.39 (1H, t, J=5.2 Hz), 6.05 (1H, d, J=1.2 Hz), 5.50 (1H, d, J=8.0 Hz), 5.42 (1H, dd, J=6.4, 1.2 Hz), 4.99 (1H, dd, J=6.4, 3.2 Hz), 4.94 (2 H, s), 4.74 (2 H, br s), 4.55 (1 H, td, J=8.0, 6.4 Hz), 4.39-4.47 (1H, m), 4.26-4.34 (1H, m), 4.17-4.24 (1H, m), 4.10 (2 H, qd, J=7.2, 1.5 Hz), 3.78 (3 H, s), 3.02 (2 H, qd, J=9.6, 6.0 Hz), 1.59 (3H, s), 1.37 (3H, s), 1.17 (3H, t, J=7.2 Hz); $^{13}$C NMR (CDCl$_3$, 100 MHz) δ 171.1, 159.1, 158., 154.8, 154.4, 153.1, 139.1, 139.0, 135.5, 13.4, 129.1, 129.0, 128.9, 128.7, 128.3, 126.8, 120.1, 114.9, 114.3, 113.8, 90.8, 8.2, 84.0, 81.6, 69.8, 64.7, 61.5, 55.2, 54.9, 43.4, 38.3, 27.2, 25.5, 14.2; ESI-HRMS calcd. for C$_{40}$H$_{45}$N$_6$O$_9$: 753.3248, found: m/z 753.3228 [M+H]$^+$.

N$^6$-(4-(Benzoyloxy)benzyl)-2',3'-O-isopropylidene-5'-O-((methyl glycinate)-N-carbonyl)-adenosine (6b-1)

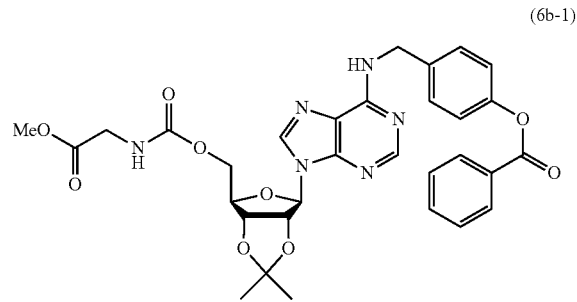
(6b-1)

A mixture of compound 4b (93 mg, 0.18 mmol) and 1,1'-carbonyldiimidazole (117 mg, 0.72 mmol) in anhydrous tetrahydrofuran (THF, 2 mL) was stirred at room temperature under argon for 1 h. After the reaction was complete (monitored by TLC), water (9.72 uL, 0.54 mmol), glycine methyl ester (as the hydrochloric salt, 90 mg, 0.72 mmol) and DIEA (129 μL, 0.72 mmol) were added. The mixture was stirred for another 12 h, and then concentrated by rotary evaporation under reduced pressure. The residue was diluted with EtOAc, wash with 1 M HCl, saturated NaHCO$_3$, water and brine successively. The organic phase was dried over MgSO$_4$, filtered, concentrated by rotatory evaporation, and purified by column chromatography (silica gel, hexane/EtOAc, gradients from 1:1 to 0:1) to give the carbamate compound 6b-1 (69 mg, 60% yield). C$_{31}$H$_{32}$N$_6$O$_9$; colorless oil; TLC (EtOAc/hexane (1:1)) R$_f$=0.12; [α]$_D^{25}$=−32.5 (CH$_2$Cl$_2$, c=2); IR ν$_{max}$ (neat) 3366, 2988, 2952, 1731, 1620, 1583, 1508, 1481, 1452, 1438, 1419, 1376, 1331, 1267, 1209, 1081, 1064 cm$^{-1}$; $^1$H NMR (CDCl$_3$, 400 MHz) δ 8.36 (1 H, br s), 8.15 (2H, d, J=7.6 Hz), 7.75 (1 H, br s), 7.59 (1 H, t, J=7.2 Hz), 7.46 (2H, dd, J=7.6, 7.2 Hz), 7.40 (2H, d, J=8.4 Hz), 7.13 (2H, d, J=8.4 Hz), 6.89 (1 H, br s), 6.07 (1 H, s), 5.99 (1 H, br s), 5.30 (1H, d, J=5.2 Hz), 4.94 (1H, dd, J=5.6, 3.2 Hz), 4.85 (2 H, br s), 4.38-4.44 (1H, m), 4.29-4.37 (1H, m), 4.15 (1H, dd, J=11.2, 5.6 Hz), 3.80-3.98 (2H, m), 3.66 (3H, s), 1.56 (3H, s), 1.32 (3 H, s); $^{13}$C NMR (CDCl$_3$, 100 MHz) δ 170.5, 165.1, 155.8, 154.6, 153.3, 150.1, 148.4, 139.3, 136.3, 133.5, 130.1, 129.4, 128.7, 128.5, 121.8, 120.1, 114.3, 90.6, 84.9, 84.0, 81.4, 64.8, 52.3, 42.5, 29.6, 27.1, 25.2; ESI-HRMS calcd. for C$_{31}$H$_{33}$N$_6$O$_9$: 633.2309, found: m/z 633.1201 [M+H]$^+$.

N⁶-(4-(Benzoyloxy)benzyl)-2',3'-O-isopropylidene-5'-O-(methyl L-valinate)-N-carbonyl)-adenosine (6b-2)

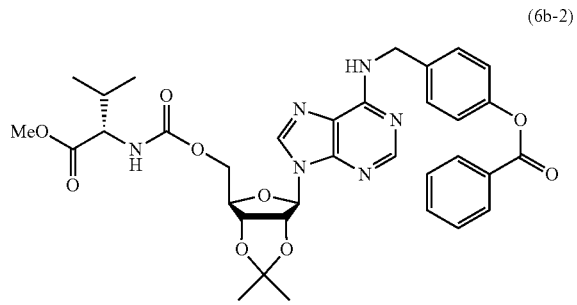

(6b-2)

A mixture of compound 4a (70 mg, 0.13 mmol) and 1,1'-carbonyldiimidazole (90 mg, 0.55 mmol) in anhydrous THF (4 mL) was stirred at room temperature under argon for 1 h. After the reaction was complete (monitored by TLC), water (4.8 µL, 0.26 mmol), L-valine methyl ester hydrochloride (90 mg, 0.55 mmol) and DIEA (96 µL, 0.55 mmol) were added. The mixture was stirred for another 12 h, and then concentrated by rotary evaporation under reduced pressure. The residue was diluted with EtOAc, washed with 1 M HCl, saturated NaHCO₃, water and brine successively. The organic phase was dried over MgSO₄, filtered, concentrated by rotary evaporation, and purified by column chromatography (silica gel, hexane/EtOAc, gradients from 2:1 to 0:1) to give compound 6b-2 (35 mg, 40% yield). $C_{34}H_{38}N_6O_9$; white solid; mp 83.9-84.6° C.; TLC (EtOAc/hexane (1:1)) $R_f$=0.21; $[\alpha]_D^{25}$=−17.6 (CH₂Cl₂, c=2); IR $v_{max}$ (neat) 3363, 2964, 2936, 1731, 1620, 1508, 1481, 1452, 1375, 1332, 1266, 1208, 1166, 1082, 1064, 1025 cm⁻¹; ¹H NMR (CDCl₃, 400 MHz) δ 8.38 (1 H, br s), 8.17 (1H, d, J=7.2 Hz), 7.76 (1 H, s), 7.60 (1H, t, J=7.6 Hz), 7.48 (2H, dd, J=7.2, 7.6 Hz), 7.41 (2H, d, J=8.4 Hz), 7.15 (2H, d, J=8.4 Hz), 6.60 (1H, t, J=5.6 Hz), 6.07 (1 H, s), 5.41-5.51 (2H, m), 5.05 (1H, dd, J=6.0, 3.2 Hz), 4.86 (2 H, br s), 4.40-4.47 (1H, m), 4.28-4.37 (1H, m), 4.16-4.26 (2H, m), 3.68 (3 H, s) 2.00-2.16 (1H, m), 1.58 (3H, s), 1.37 (3H, s), 0.84 (6H, dd, J=24.0, 6.8 Hz); ¹³C NMR (CDCl₃, 100 MHz) δ 172.4, 165.1, 155.6, 154.7, 153.3, 150.2, 146.7, 139.4, 136.2, 133.6, 130.1, 129.4, 128.8, 128.5, 121.9, 120.4, 114.5, 90.9, 85.3, 84.0, 81.7, 64.8, 59.0, 52.1, 31.2, 29.6, 27.1, 25.3, 18.8, 17.5; ESI-HRMS calcd. for $C_{34}H_{39}N_6O_9$: 675.2779, found: m/z 675.2755 [M+H]⁺.

5'-O-((Ethyl glycinate)-N-carbonyl)-N⁶-(4-hydroxybenzyl)adenosine (7a-1)

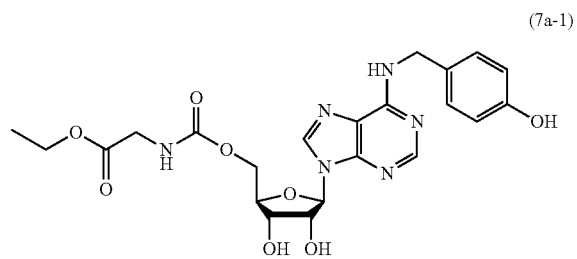

(7a-1)

A solution of compound 6a-1 (92 mg, 0.14 mmol) in MeOH (0.8 mL) and water (0.2 mL) was stirred at 0° C. while TFA (2 mL) was added slowly. After the addition was complete, the mixture was warmed to room temperature and stirred for another 2 h. The mixture was concentrated by rotatory evaporation under reduced pressure, diluted with MeOH/EtOAc (1:9), and washed with saturated NaHCO₃, water and brine successively. The organic phase was dried over MgSO₄, filtered, concentrated by rotatory evaporation under reduced pressure, and purified by column chromatography (silica gel, MeOH/EtOAc, gradients from 0:1 to 1:9) to give compound 7a-1 (32 mg, 37% yield). $C_{22}H_{26}N_6O_8$; white solid; mp 197.9-199.2° C.; $[\alpha]_D^{25}$=−36.3 (DMSO, c=2); IR $v_{max}$ (film) 3328, 2933, 1708, 1637, 1517, 1499, 1334, 1303, 1265, 1240, 1219, 1174, 1136, 1080 cm⁻¹; ¹H NMR (DMSO-d₆, 400 MHz) δ 9.23 (1H, s), 8.35 (1H, s), 8.27 (1 H, br s), 8.22 (1 H, br s), 7.75 (1H, t, J=6.0 Hz), 7.14 (2H, d, J=8.0 Hz), 6.67 (2H, d, J=8.0 Hz), 5.93 (1H, d, J=6.0 Hz), 5.53 (1H, d, J=6.0 Hz), 5.39 (1H, d, J=4.8 Hz), 4.67 (1H, d, J=6.0 Hz), 4.59 (2 H, br s), 4.26 (1 H, dd, J=11.6, 2.8 Hz), 4.13-4.18 (2H, m), 4.07-4.13 (3H, m), 3.74 (2H, d, J=6.0 Hz), 1.18 (3H, t, J=7.2 Hz); ¹³C NMR (DMSO-d₆, 100 MHz) δ 170.1, 156.4, 156.1, 154.4, 152.7, 149.0, 139.4, 130.2, 128.5, 115.0, 87.0, 82.3, 73.0, 70.6, 64.6, 62.8, 60.4, 42.4, 42.2, 14.1; ESI-HRMS calcd. for $C_{22}H_{27}N_6O_8$: 503.1890, found: m/z 503.1908 [M+H]⁺.

5'-O-(Glycine-N-carbonyl)-N⁶-(4-hydroxybenzyl)adenosine (I-a1)

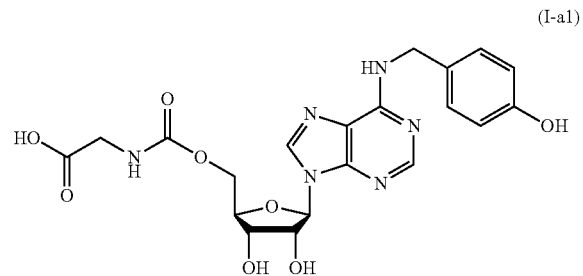

(I-a1)

Method A. To a solution of compound 7a-1 (25 mg, 0.05 mmol) in MeOH (4 mL) was added 1 M NaOH (4 mL). The mixture was stirred for was 30 min, concentrated by rotary evaporation under reduced pressure, and purified by reversed-phase column chromatography (RP-18 silica gel, MeOH/H₂O, gradients from 0:1 to 1:1) to give compound I-a1 (18 mg, 76% yield).

Method B. A solution of ester 6b-1 (125 mg, 0.19 mmol) in MeOH (0.9 mL) and water (0.1 mL) was stirred at 0° C. while TFA (2 mL) was added slowly. After the addition was complete, the mixture was warmed to room temperature and stirred for another 2 h. The reaction was concentrated by rotatory evaporation under reduced pressure, diluted with MeOH/EtOAc (1:9), and washed with saturated NaHCO₃, water and brine successively. The organic phase was dried over MgSO₄, filtered and concentrated by rotatory evaporation under reduced pressure. The residue was diluted with MeOH (3 mL), added 1 M NaOH (3 mL), and stirred at room temperature for 30 min. The mixture was concentrated by rotatory evaporation under reduced pressure, and purified by normal-phase column chromatography (silica gel, AcOH/MeOH/EtOAc, gradients from 0:1:9 to 1:1:8) then reversed-phase column chromatography (RP-18 silica gel, MeOH/

H₂O, gradients from 0:1 to 1:1) to give compound I-a1 (67 mg, 74% yield). The purity of product I-a1 was 98.1% as shown by HPLC on Chromolith RP-18 high-resolution column (Merck, 100 mm×4.6 mm), $t_R$=11.05 min ((CH₃CN/0.5% TFA aqueous solution, gradients from 0% to 20% in 15 min). $C_{20}H_{22}N_6O_8$; white solid; mp 172.4-174.6° C.; $[\alpha]_D^{25}$=−19.5 (H₂O, c=1); IR $v_{max}$ (film) 3192, 2951, 1708, 1686, 1641, 1595, 1521, 1491, 1447, 1410, 1356, 1310, 1262, 1230, 1196, 1169, 1159, 1142, 1068, 1032 cm⁻¹; ¹H NMR (CD₃OD, 400 MHz) δ 8.29 (1 H, br s), 8.27 (1 H, br s), 7.21 (2H, d, J=8.4 Hz), 6.74 (2H, d, J=8.4 Hz), 6.05 (1H, d, J=5.4 Hz), 4.66-4.73 (3H, m), 4.34-4.40 (2H, m), 4.28-4.33 (1H, m), 4.22-4.27 (1H, m), 3.61-3.72 (2H, m); ¹³C NMR (CD₃OD, 100 MHz) δ 177.3, 158.6, 158.0, 156.1, 154.2, 150.2, 140.6, 131.0, 130.2, 120.8, 116.5, 89.6, 84.6, 75.7, 72.1, 65.3, 45.9, 45.0; ESI-HRMS (negative mode) calcd. for $C_{20}H_{21}N_6O_8$: 473.1421, found: m/z 473.1416 [M−H]⁻.

N⁶-(4-Hydroxybenzyl)-5'-O-(L-phenylalanine-N-carbonyl)adenosine (I-a2)

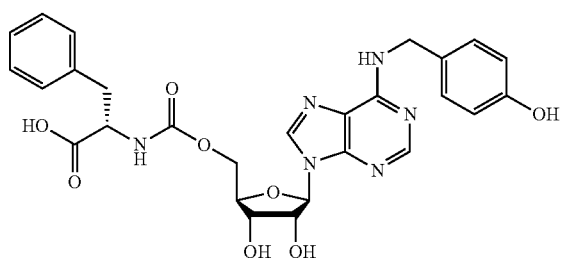

(I-a2)

A solution of compound 6a-2 (72 mg, 0.1 mmol) in MeOH (0.8 mL) and water (0.2 mL) was stirred at 0° C. while TFA (2 mL) was added slowly. After the addition was complete, the reaction was warmed to room temperature and stirred for another 2 h. The reaction was concentrated by rotatory evaporation under reduced pressure. The residue was diluted with MeOH (4 mL) and stirred at room temperature while 1 M NaOH (4 mL) was added. The mixture was stirred for was 30 min, concentrated by rotary evaporation under reduced pressure, and purified by reversed-phase column chromatography (RP-18 silica gel, water/MeOH, gradients from 1:0 to 1:1) to give compound I-a2 (43 mg, 76% yield). The purity of product I-a2 was 95.1% as shown by HPLC on Chromolith RP-18 high-resolution column (Merck, 100 mm×4.6 mm), $t_R$=11.0 min (CH₃CN/0.5% TFA aqueous solution, gradients of 5% to 40% aqueous CH₃CN in 15 min). $C_{27}H_{28}N_6O_8$; white solid; mp 180.2-182.3° C.; $[\alpha]_D^{25}$=−7.40 (DMSO, c=1); IR $v_{max}$ (film) 3409, 2940, 1702, 1642, 1517, 1498, 1453, 1401, 1340, 1248, 1178, 1082, 1056 cm⁻¹; ¹H NMR (CD₃OD, 400 MHz) δ 8.25 (1H, s), 8.22 (1H, s), 7.19 (2H, d, J=8.4 Hz), 7.15-7.17 (2H, m), 7.10-7.14 (2H, m), 7.04-7.08 (1H, m), 6.73 (2H, d, J=8.4 Hz), 6.02 (1H, d, J=4.4 Hz), 4.67 (2 H, br s), 4.63 (1H, dd, J=4.4, 4.4 Hz), 4.30-4.34 (1H, m), 4.23-4.29 (2H, m), 4.17-4.21 (2H, m), 3.17 (1H, dd, J=14.0, 4.8 Hz), 2.83-2.92 (1H, m); ¹³C NMR (CDCl₃, 100 MHz) δ 177.4, 157.8, 157.7, 155.9, 154.0, 149.9, 140.5, 139.2, 130.8, 130.4, 130.0, 129.2, 127.4, 120.7, 116.3, 89.4, 84.4, 75.5, 71.8, 65.1, 58.1, 44.8, 39.2; ESI-HRMS (negative mode) calcd. for $C_{27}H_{27}N_6O_8$: 563.1890 found: m/z 563.1871 [M−H]⁻.

N⁶-(4-Hydroxybenzyl)-5'-O-(L-valine-N-carbonyl)adenosine (I-a3)

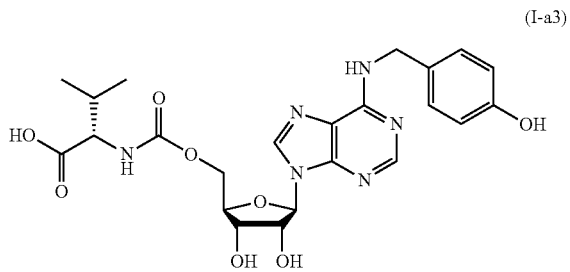

(I-a3)

A solution of compound 6b-2 (35 mg, 0.05 mmol) in MeOH (0.4 mL) and water (0.1 mL) was stirred at 0° C. while TFA (1 mL) was added slowly. After the addition was complete, the reaction was warmed to room temperature and stirred for another 2 h. The mixture was concentrated by rotatory evaporation under reduced pressure. The residue was diluted with MeOH (4 mL) and stirred at room temperature while 1 M NaOH (4 mL) was added and react for 30 min. The mixture was concentrated by rotary evaporation under reduced pressure, purified by normal phase column chromatography (silica gel, AcOH/MeOH/EtOAc, gradients from 0:1:9 to 1:1:8) and reversed-phase column chromatography (RP-18 silica gel, water/MeOH, gradients from 1:0 to 1:1) to give compound I-a3 (21 mg, 80% yield). The purity of product I-a3 was 98.9% as shown by HPLC on Chromolith RP-18 high-resolution column (Merck, 100 mm×4.6 mm), $t_R$=3.78 min (CH₃CN/0.5% TFA aqueous solution, gradients of 15% to 40% in 15 min). $C_{23}H_{28}N_6O_8$; white solid; mp 166.6-168.8° C.; TLC (MeOH/AcOH/EtOAc (1:1:8)) $R_f$=0.5; $[\alpha]_D^{25}$=−2.2 (DMSO, c=1); IR $v_{max}$ (film) 3332, 2965, 1702, 1625, 1517, 1466, 1406, 1340, 1240, 1173, 1107, 1087, 1050 cm⁻¹; ¹H NMR (CD₃OD, 400 MHz) δ 8.27 (2 H, s), 7.24 (2H, d, J=8.8 Hz), 6.75 (2H, d, J=8.8 Hz), 6.05 (1H, d, J=5.6 Hz), 4.72-4.74 (1H, m), 4.70 (2 H, br s), 4.38-4.43 (1H, m), 4.29-4.36 (2H, m), 4.24-4.27 (1H, m), 4.02 (1H, d, J=5.2 Hz), 2.09-2.20 (1H, m), 0.93 (7H, dd, J=16.4, 6.8 Hz); ¹³C NMR (CD₃OD, 100 MHz) δ 176.5, 158.5, 157.8, 155.9, 154.0, 150.0, 14.6, 130.8, 130.0, 120.7, 116.3, 89.5, 84.3, 75.3, 72.0, 65.5, 61.7, 44.8, 31.9, 19.8, 18.2; ESI-HRMS calcd. for $C_{23}H_{29}N_6O_8$: 517.2047, found: m/z 517.2040 [M+H]⁺.

5'-O-(n-Butylaminocarbonyl)-N⁶-(4-hydroxybenzyl)adenosine (8)

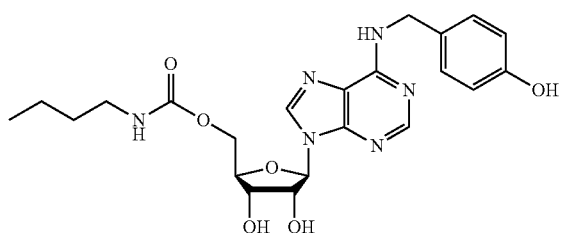

(8)

A mixture of compound 4b (70 mg, 0.14 mmol) and 1,1'-carbonyldiimidazole (90 mg, 0.56 mmol) in anhydrous THF (4 mL) was stirred at room temperature under argon for 2 h. After the reaction was complete (monitored by TLC), water (4.8 μL, 0.28 mmol) and butylamine (110 μL, 1.1 mmol) was added successively. The mixture was stirred for another 12 h, and then concentrated by rotary evaporation under reduced pressure. The residue was diluted with EtOAc, washed with 1 M HCl, water and brine successively. The organic phase was dried over MgSO$_4$, filtered, and concentrated by rotary evaporation to give a crude product.

A solution of the crude product in MeOH (0.8 mL) and water (0.2 mL) was stirred at 0° C. while TFA (2 mL) was added slowly. After the addition was complete, the mixture was warmed to room temperature and stirred for another 2 h. The mixture was concentrated by rotary evaporation under reduced pressure, diluted with MeOH/EtOAc (1:9), and extracted with saturated NaHCO$_3$, water and brine successfully. The organic phase was dried over MgSO$_4$, filtered and concentrated by rotary evaporation. The residue was diluted with MeOH (2 mL) and stirred at room temperature while 1 M NaOH (2 mL) was added. The mixture was stirred at room temperature for 30 min, and concentrated by rotary evaporation under reduced pressure. The residue was diluted with MeOH/EtOAc (1:9), washed with water and brine successively. The organic phase was dried over MgSO$_4$, filtered, concentrated by rotary evaporation, and purified by column chromatography (silica gel, MeOH/CH$_2$Cl$_2$, gradients from 0:1 to 1:9) to give compound 8 (34 mg, 51% yield). The purity of product 8 was 98.2% as shown by HPLC on Chromolith® RP-18 high-resolution column (Merck, 100 mm×4.6 mm), $t_R$=6.6 min (CH$_3$CN/0.5% TFA aqueous solution, gradients of 15% to 40% in 15 min). C$_{22}$H$_{28}$N$_6$O$_6$; white solid; mp 187.4-189.0° C.; TLC (MeOH/CH$_2$Cl$_2$ (1:19)) R$_f$=0.08; [α]$_D^{25}$=−31.3 (DMSO, c=2); IR $v_{max}$ (film) 3339, 3149, 2958, 2933, 2872, 1696, 1620, 1519, 1465, 1372, 1337, 1293, 1248, 1168, 1115, 1079, 1049 cm$^{-1}$; $^1$H NMR (CD$_3$OD, 400 MHz) δ 8.26 (1H, s), 8.20 (1H, s), 7.21 (2H, d, J=8.4 Hz), 6.74 (2H, d, J=8.4 Hz), 6.03 (1H, d, J=4.8 Hz), 4.61-4.75 (3H, m), 4.37-4.43 (1H, m), 4.33 (1H, t, J=4.4 Hz), 4.20-4.29 (2H, m), 3.08 (2 H, t, J=6.8 Hz), 1.38-1.51 (2H, m), 1.25-1.37 (2H, m), 0.90 (3H, t, J=7.3 Hz); $^{13}$C NMR (CD$_3$OD, 100 MHz) δ 158.7, 158.0, 156.2, 154.2, 140.5, 131.1, 130.1, 121.0, 116.5, 90.2, 84.4, 75.7, 72.2, 65.3, 41.8, 33.1, 21.0, 14.1; ESI-HRMS calcd. for C$_{22}$H$_{29}$N$_6$O$_6$: 473.2149, found: m/z 473.2145 [M+H]$^+$.

2',3'-O-Isopropylidene-5'-O-((3-methoxycarbonyl-propylamino)carbonyl)-N$^6$-(4-(4-methoxybenzy-loxy)benzyl)adenosine (9)

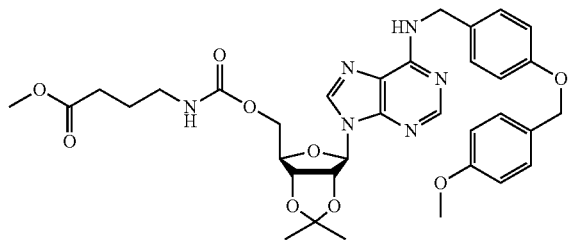

(9)

A mixture of compound 5a (90 mg, 0.14 mmol), DMAP (catalytic amount), DIEA (110 μL, 0.6 mmol) and γ-aminobutyric acid methyl ester (as the hydrochloride salt, 180 mg, 1.2 mmol) in DMF (3 mL) was stirred at room temperature under argon for 12 h. After the reaction was complete (monitored by TLC), the mixture was concentrated by rotary evaporation under reduced pressure. The residue was diluted with EtOAc, and washed with 1 M HCl, saturated NaHCO$_3$, water and brine successively. The organic phase was dried over MgSO$_4$, filtered, concentrated by rotary evaporation under reduced pressure, and purified by column chromatography (silica gel, EtOAc/hexane, gradients from 1:3 to 9:1) to give compound 9 (97 mg, 99%). C$_{34}$H$_{40}$N$_6$O$_9$; oil; [α]$_D^{25}$=−32.6 (CH$_2$Cl$_2$, c=2); IR $v_{max}$ (neat) 3359, 2989, 2938, 1727, 1614, 1584, 1514, 1479, 1467, 1377, 1330, 1297, 1243, 1174, 1089, 1033 cm$^{-1}$; $^1$H NMR (CDCl$_3$, 400 MHz) δ 8.37 (1 H, br s), 7.73 (1 H, s), 7.31 (2H, d, J=8.4 Hz), 7.25 (2H, d, J=8.4 Hz), 6.89 (2H, d, J=8.4 Hz), 6.88 (2H, d, J=8.4 Hz), 6.47 (1 H, br s), 6.05 (1 H, s), 5.42-5.47 (1H, m), 5.01 (1H, dd, J=5.6, 2.8 Hz), 4.94 (2 H, s), 4.74 (2 H, br s), 4.42 (1H, d, J=2.9 Hz), 4.25-4.32 (1H, m), 4.13-4.21 (1H, m), 3.77 (3H, s), 3.61 (3H, s), 3.12 (2 H, q, J=6.3 Hz), 2.28 (2H, t, J=7.2 Hz), 1.74 (2 H, quin, J=6.9 Hz), 1.58 (3 H, s), 1.36 (3 H, s); $^{13}$C NMR (CDCl$_3$, 100 MHz) δ 173.5, 159.3, 158.1, 155.7, 154.6, 153.3, 139.0, 130.6, 129.1, 129.0, 128.8, 120.2, 114.9, 114.4, 113.9, 91.0, 85.2, 84.0, 81.6, 69.7, 64.4, 55.2, 51.6, 43.8, 40.3, 31.0, 27.1, 25.3, 24.9; ESI-HRMS calcd. for C$_{34}$H$_{41}$N$_6$O$_9$: 677.2935, found: m/z 677.2933 [M+H]$^+$.

5'-O-((3-Carboxypropylamino)carbonyl)-N$^6$-(4-hydroxybenzyl)adenosine (I-b1)

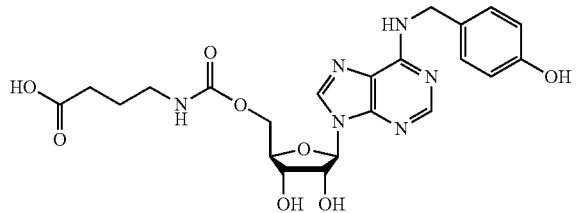

(I-b1)

A solution of compound 9 (92 mg, 0.14 mmol) in MeOH (0.8 mL) and water (0.2 mL) was stirred at 0° C. while TFA (2 mL) was added slowly. After the addition was complete, the mixture was warmed to room temperature and stirred for another 2 h. The mixture was concentrated by rotary evaporation under reduced pressure, diluted with MeOH/EtOAc (1:9), and washed with saturated NaHCO$_3$, water and brine successfully. The organic phase was dried over MgSO$_4$, filtered, concentrated by rotary evaporation under reduced pressure. The residue was diluted with MeOH (4 mL), added 1 M NaOH (4 mL), and stirred for 30 min. The mixture was concentrated by rotary evaporation under reduced pressure, diluted with H$_2$O, and washed with EtOAc. The aqueous phase was concentrated by rotary evaporation under reduced pressure, and purified by reversed phase column chromatography (RP-18 silica gel, water/MeOH, gradients from 1:0 to 1:1) to give compound I-b1 (32.1 mg, 47%). The purity of product I-b1 was 98.0% as shown by HPLC on Chromolith RP-18 high-resolution column (Merck, 100 mm×4.6 mm), $t_R$=10.2 min (CH$_3$CN/0.5% TFA aqueous solution, gradients of 0% to 30% in 15 min). C$_{22}$H$_{26}$N$_6$O$_8$; white solid; mp 226.1-229.0° C.; [α]$_D^{25}$=−29.7 (H$_2$O, c=1); IR $v_{max}$ (film) 3482, 3414, 2929, 1701, 1619, 1560, 1546, 1517, 1459, 1438, 1340, 1259, 1129, 1087, 1053 cm$^{-1}$; $^1$H NMR (CD$_3$OD, 400 MHz) δ 8.26 (1H, s), 8.23 (1H, s), 7.21 (2H, d, J=8.4 Hz), 6.74 (2H, d, J=8.4 Hz), 6.05 (1H, d, J=5.4 Hz), 4.82-4.84 (2H, m), 4.68 (1H, t, J=5.2 Hz), 4.33-4.41 (2H, m), 4.20-4.31 (2H, m), 3.05-3.17 (2H, m), 2.18 (2 H, t, J=7.2 Hz), 1.76 (2 H, quin, J=7.2 Hz); $^{13}$C NMR (CD$_3$OD, 100 MHz) δ 183.2, 158.7, 158.0, 156.1, 154.2, 150.1, 140.5, 131.0, 130.2, 120.9, 116.5, 89.7, 84.5, 75.6, 72.2, 65.2, 45.0, 52.0, 36.0, 27.6; ESI-HRMS calcd. for C$_{22}$H$_{27}$N$_6$O$_8$: 503.1890, found: m/z 503.1894 [M+H]$^+$.

N-[2′,3′-O-Isopropylidene-N$^6$-(4-(4-methoxybenzyloxy)benzyl)adenosine-5′-O-carbonyl]glycyl-L-leucyl-L-methioninamide (10)

saturated NaHCO$_3$, water and brine successively. The organic phase was dried over MgSO$_4$, filtered, concentrated by rotatory evaporation, and purified by column chromatography (silica gel, AcOH/MeOH/EtOAc, gradients from 0:0:1 to 1:1:8) to give a coupling compound 10 (115 mg, 77% yield). C$_{42}$H$_{55}$N$_9$O$_{10}$S; colorless oil; TLC (AcOH/EtOAc (1:9)) R$_f$=0.26; [α]$_D^{25}$=−38.1 (acetone, c=1); IR ν$_{max}$ (neat) 3309, 2954, 2925, 2872, 2361, 2337, 1716, 1663, 1618, 1585, 1516, 1467, 1381, 1242, 1172, 1086, 1033 cm$^{-1}$; $^1$H NMR (CDCl$_3$, 400 MHz) δ 8.35 (1 H, br s), 8.08 (1 H, br s), 7.93 (1 H, s), 7.71 (1 H, br s), 7.29 (2H, d, J=8.4 Hz), 7.23 (2H, d, J=8.0 Hz), 7.07 (1 H, br s), 6.98 (1 H, br s), 6.85 (2H, d, J=8.4 Hz), 6.84 (2H, d, J=8.0 Hz), 6.57 (1 H, br s), 6.47 (1 H, br s), 6.09 (1 H, br s), 5.33 (1H, d, J=4.4 Hz), 4.95 (1 H, br s), 4.89 (2 H, s), 4.74 (2 H, br s), 4.57 (1H, d, J=5.6 Hz), 4.50 (1 H, br s), 4.28 (1H, d, J=8.8 Hz), 4.06-4.16 (1H,

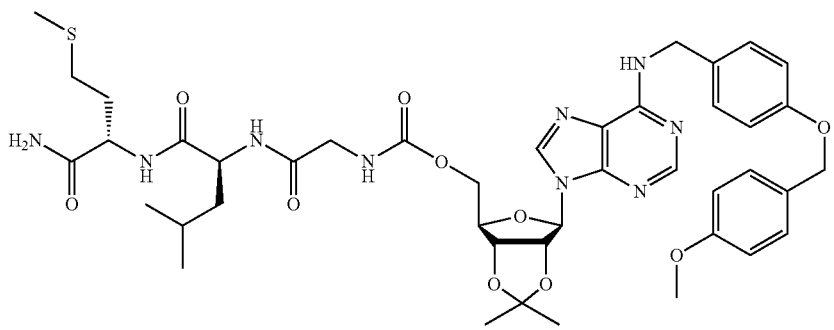

(10)

A solution of compound 6a-1 (130 mg, 0.17 mmol) in 1 M NaOH (2 mL) and MeOH (2 mL) was stirred at room temperature for 30 min. The mixture was concentrated by rotary evaporation under reduced pressure. The residue was diluted with EtOAc, washed with 1 M HCl, water and brine successively. The organic phase was dried over MgSO$_4$, filtered, concentrated by rotatory evaporation under reduced pressure. To the residue in DMF (3 mL) were added 1-ethyl-3-(3-dimethylaminopropyl)carbodiimide (EDCI, 57 mg, 0.29 mmol) and hydroxybenzotriazole (HOBt, 40 mg, 0.30 mmol). The mixture was stirred at 0° C. for 30 min. After the activation procedure was complete (monitored by TLC), a solution of L-leucyl-L-methionine amide hydrochloride (223 mg, 0.75 mmol) and DIEA (100 μL, 0.56 mmol) in DMF (3 mL) was added. The mixture was stirred at room temperature for 16 h, and then concentrated by rotary evaporation under reduced pressure. The residue was diluted with MeOH/EtOAc (1:9), washed with 1 M HCl (twice), m), 3.82 (1 H, br s), 3.75 (3 H, s), 2.43 (2 H, br s), 1.97-2.09 (1H, m), 1.95 (3 H, s), 1.91 (1 H, br s), 1.55 (5 H, s), 1.48 (1 H, br s), 1.32 (3 H, s), 0.74-0.86 (6H, m); $^{13}$C NMR (CDCl$_3$, 100 MHz) δ 174.0, 172.5, 169.8, 159.4, 158.1, 156.4, 154.6, 138.9, 134.2, 130.9, 129.4, 129.2, 129.0, 128.9, 119.9, 114.8, 114.5, 113.9, 90.5, 84.8, 84.3, 8.2, 697, 64.8, 55.2, 52.5, 52.1, 44.3, 41.0, 1.0, 30.5, 30.2, 28.9, 27.1, 25.3, 24.7, 22.7, 22.0, 15.2, 14.0, 11.0; ESI-HRMS calcd. for C$_{42}$H$_{56}$N$_9$O$_{10}$S: 878.3874, found: m/z 878.3866 [M+H]$^+$.

N-[(N$^6$-(4-Hydroxybenzyl)adenosine)-5′-O-carbonyl]glycyl-L-leucyl-L-methioninamide (I-c1)

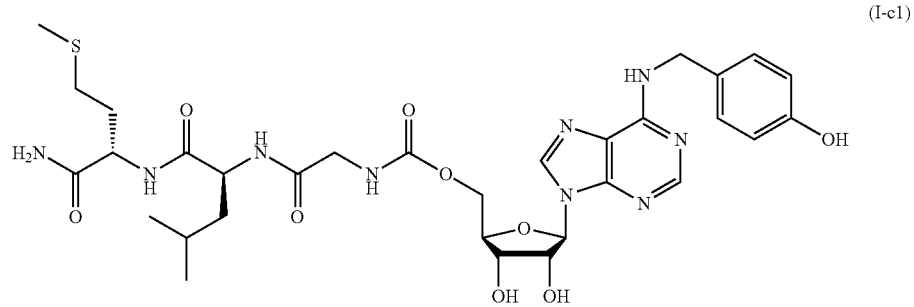

(I-c1)

A solution of compound 10 (115 mg, 0.13 mmol) in MeOH (2 mL) and water (0.5 mL) was stirred at 0° C. while TFA (5 mL) was added slowly. After the addition was complete, the mixture was warmed to room temperature and stirred for another 2 h. The mixture was concentrated by rotatory evaporation under reduced pressure, diluted with saturated NaHCO$_3$, and extracted successively with EtOAc and n-BuOH. The organic phase was collected, and concentrated by rotatory evaporation under reduced pressure. The residue was purified by reversed-phase column chromatography on RP-18 gel (water/MeOH, isocratic 1:3), and repeatedly on another RP-18 gel column (water/acetone, gradients from 1:0 to 1:1), to give the tripeptide conjugated compound I-c1 (46.7 mg, 50% yield). The purity of product I-c1 was 96.9% as shown by HPLC on Chromolith RP-18 high-resolution column (Merck, 100 mm×4.6 mm), $t_R$=6.3 min (CH$_3$CN/0.5% TFA aqueous solution, gradients of 15% to 40% in 15 min). C$_{31}$H$_{43}$N$_9$O$_9$S; white powder; mp 181.2-184.3° C.; $[\alpha]_D^{25}$=−34.0 (DMSO, c=2); IR $\nu_{max}$ (film) 3297, 2958, 2917, 1703, 1679, 1626, 1544, 1516, 1446, 1417, 1250, 1172, 1127, 1082, 1046 cm$^{-1}$; $^1$H NMR (DMSO-d$_6$, 400 MHz) δ 9.23 (1H, s), 8.36 (1H, s), 8.27 (1 H, br s), 8.22 (1 H, br s), 8.05 (1H, d, J=7.8 Hz), 7.92 (1H, d, J=8.0 Hz), 7.57 (1H, t, J=5.2 Hz), 7.17 (1 H, br s), 7.14 (2H, d, J=8.4 Hz), 7.07 (1 H, br s), 6.67 (2H, d, J=8.4 Hz), 5.92 (1H, d, J=6.0 Hz), 5.52 (1H, d, J=6.0 Hz), 5.39 (1H, d, J=4.8 Hz), 4.67 (1H, dd, J=6.0, 6.0 Hz), 4.59 (2 H, br s), 4.19-4.32 (3H, m), 4.10-4.19 (2H, m), 4.03-4.09 (1H, m), 3.63 (2H, d, J=3.2 Hz), 2.29-2.47 (2H, m), 2.02 (3 H, s), 1.87-1.98 (1H, m), 1.72-1.85 (1H, m), 1.59 (1 H, d septet, J=6.4, 6.4 Hz), 1.45 (2H, dd, J=6.4, 3.2 Hz), 0.87 (7H, d, J=6.4 Hz), 0.83 (7H, d, J=6.4 Hz); $^{13}$C NMR (DMSO-d$_6$, 100 MHz) δ 172.3, 171.9, 169.2, 156.4, 156.1, 154.3, 152.6, 137.3, 13.2, 129., 128.5, 114.9, 86.9, 82.3, 73.0, 70.6, 64.5, 51.7, 51.2, 43.4, 40.6, 31.5, 29.7, 24.1, 23.0, 21.5, 14.6; ESI-HRMS calcd. for C$_{31}$H$_{44}$N$_9$O$_9$S: 718.2983, found: m/z 718.2972 [M+H]$^+$.

Substance-P Conjugate Compound (I-c2)

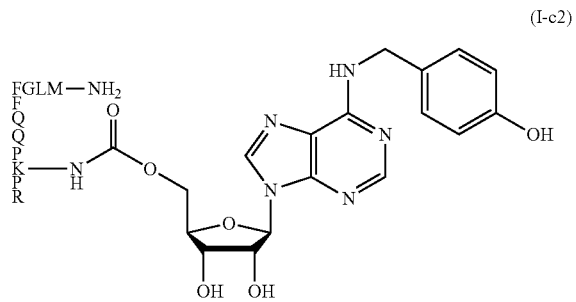

(I-c2)

A mixture of compound 5a (130 mg, 200 μmol) and an undecapeptide Arg-Pro-Lys-Pro-Gln-Gln-Phe-Phe-Gly-Leu-Met-CONH$_2$ (SEQ ID NO:1) (substance P, 10 mg, 7 μmol) in a two-phase system of CH$_2$Cl$_2$ (5 mL) and PBS solution (5 mL) was stirred vigorously at room temperature under argon for 4 h. The two phases were separated using a separation funnel. The aqueous layer was centrifuged (8000 rpm, 20 min, 4° C.), and the supernatant was decanted. The residue was washed with water, centrifuged (8000 rpm, 20 min, 4° C.) again to give a crude product after removal of supernatant.

A solution of the crude product (10 mg, 5.2 μmol) in MeOH (0.4 mL) and water (0.1 mL) was stirred at 0° C. while TFA (1 mL) was added slowly. After the addition was complete, the mixture was warmed to room temperature and stirred for another 2 h. The mixture was concentrated by rotatory evaporation under reduced pressure, and purified by reversed-phase column chromatography (RP-18 gel, water/MeOH, gradients from 1:0 to 1:1) to give compound I-c2 (1.6 mg, 12% yield). The purity of product I-c2 was 96.2% as shown by HPLC on Chromolith RP-18 high-resolution column (Merck, 100 mm×4.6 mm), $t_R$=1.8 min (CH$_3$CN/0.5% TFA aqueous solution, gradients of 10% to 20% in 15 min). C$_{81}$H$_{115}$N$_{23}$O$_{19}$S; white powder; RP-18 TLC (AcOH/MeOH/H$_2$O (2:9:9)) R$_f$=0.45; MALDI-TOF calcd. for C$_{81}$H$_{116}$N$_{23}$O$_{19}$S: 1746.8, found: m/z 1746.7 [M+H]$^+$.

N$^6$-(Indol-3-yl)ethyl-2',3'-O-isopropylidene-adenosine (12)

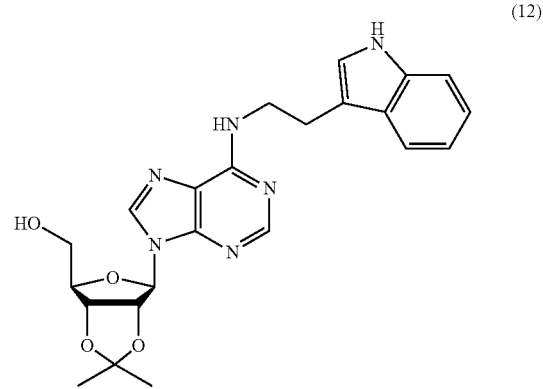

(12)

N$^6$-(Indol-3-yl)ethyladenosine (compound 11) was prepared from the substitution reaction of 6-chloropurine riboside with (indol-3-yl)ethylamine according to the previously reported procedure [Chen, J.-B.; Liu, E. M.; Chern, T.-R.; Yang, C.-W.; Lin, C.-I.; Huang, N.-K.; Lin, Y.-L.; Chern, Y.; Lin, J.-H. Fang, J.-M. Design and synthesis of novel dual-action compounds targeting the adenosine A$_{2A}$ receptor and adenosine transporter for neuroprotection. *ChemMedChem* 2011, 6, 1390-1400]. In brief, a mixture of tryptamine (2.5 equiv), 6-chloropurine riboside (1 equiv), and diisopropylethylamine (DIEA, 4.5 equiv) in ethanol was irradiated at 150 W for 10 min in a focused monomode microwave reactor. The mixture was concentrated under reduced pressure, and purified by flash chromatography (silica gel; MeOH/EtOAc (1:9)) to give compound 11 in 83% yield.

A mixture of compound 11 (147 mg, 0.36 mmol), p-toluenesulfonic acid monohydrate (75 mg, 0.48 mmol) and 2,2-dimethoxypropane (1 mL, 0.83 mmol) in acetone (2 mL) was stirred at room temperature for 4 h. The mixture was concentrated by rotary evaporation under reduced pressure. The residue was diluted with CH$_2$Cl$_2$, extracted successively with water and saturated NaHCO$_3$. The organic phase was dried over MgSO$_4$, filtered, concentrated by rotatory evaporation under reduced pressure, and purified by column chromatography (silica gel, hexane/EtOAc (1:1)) to give the acetonide compound 12 (131 mg, 81% yield). C$_{23}$H$_{26}$N$_6$O$_4$; $[\alpha]_D^{25}$=−103.4 (CHCl$_3$, c=1); IR $\nu_{max}$ (neat) 3421, 1624, 1458, 1340, 1215, 1155, 1080 cm$^{-1}$; $^1$H NMR (400 MHz, CDCl$_3$) δ 8.59 (1 H, br s), 8.33 (1 H, br s), 7.57 (1H, d, J=8.4 Hz), 7.50 (1H, d, J=2.0 Hz), 7.15-7.11 (1H, m), 7.09-7.05 (1H, m), 6.88 (1H, d, J=2.0 Hz), 6.82 (1 H, br s), 6.49 (1 H, br s), 5.74 (1 H, br s), 5.18 (1 H, t, J=5.2 Hz), 5.08 (1H, dd, J=6.0, 0.8 Hz), 4.51 (1 H, s), 3.95 (2H, m), 3.88-3.76 (2H, m), 3.06 (2H, t, J=6.8 Hz), 1.62 (3 H, s), 1.35 (3 H, s); $^{13}$C NMR (100 MHz, CDCl$_3$) δ 155.2, 139.4, 136.5, 127.3, 122.2, 119.5, 118.8, 113.9, 112.8, 111.2, 94.4, 86.1, 82.9, 81.8, 63.5, 50.4, 27.7, 25.2; ESI-HRMS calcd. for C$_{23}$H$_{27}$N$_6$O$_4$: 451.2094, found: m/z 451.2099 [M+H]$^+$.

N$^6$-(Indol-3-yl)ethyl-2',3'-O-isopropylidene-5'-O-((methyl glycinate)-N-carbonyl) adenosine (13)

(13)

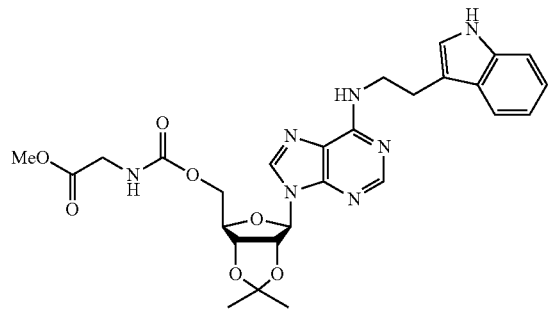

A mixture of compound 12 (78 mg, 0.17 mmol) and CDI (113 mg, 0.77 mmol) in anhydrous THF (4 mL) was stirred at room temperature under nitrogen for 2 h. Another batch of CDI (113 mg, 0.77 mmol) was added, and the mixture was stirred for 2 h. After the reaction was complete (monitored by TLC), a small amount of water was added to quench excess CDI, followed by adding glycine methyl ester hydrochloride (347 mg, 2.8 mmol) and DIEA (0.5 mL, 2.8 mmol). The mixture was stirred for another 24 h, and then concentrated by rotary evaporation under reduced pressure. The residue was diluted with CH$_2$Cl$_2$, washed with 1 M HCl, water and brine successively. The organic phase was dried over MgSO$_4$, filtered, concentrated by rotary evaporation, and purified by column chromatography (silica gel, hexane/EtOAc (2:3)) to give compound 13 (48 mg, 50% yield). C$_{27}$H$_{31}$N$_7$O$_7$; oil; [α]$_D^{25}$=−34.2 (CHCl$_3$, c=1); IR v$_{max}$ (neat) 3406, 1724, 1620, 1536, 1460, 1379, 1211, 1076 cm$^{-1}$; $^1$H NMR (CD$_3$OD) δ 8.28 (1 H, br s), 8.16 (1 H, br s), 7.59 (1H, d, J=8.0 Hz), 7.31 (1H, d, J=7.6 Hz), 7.10-7.04 (2H, m), 6.99-6.95 (1H, m), 6.18 (1H, d, J=2.8 Hz), 5.43-5.41 (1H, m), 5.08-5.06 (1H, m), 4.59 (2 H, br s), 4.55 (1H, dd, J=8.0, 4.8 Hz), 4.30 (1H, dd, J=11.6, 4.8 Hz), 4.19 (1H, dd, J=11.6, 4.8 Hz), 3.89 (1 H, br s), 3.86 (1H, s), 3.69 (3H, s), 3.12 (2H, t, J=7.2 Hz), 1.61 (3 H, s), 1.33 (3 H, s); $^{13}$C NMR (100 MHz, CD$_3$OD) δ 172.4, 158.7, 154.3, 140.8, 138.4, 129.0, 125.2, 123.8, 122.5, 119.7, 119.5, 115.7, 113.3, 112.3, 91.8, 86.0, 85.6, 83.2, 66.0, 52.8, 49.6, 49.4, 43.3, 42.6, 27.6, 26.6, 25.7; ESI-HRMS calcd. for C$_{27}$H$_{32}$N$_7$O$_7$: 566.2363, found: m/z 566.2336 [M+H]$^+$.

N$^6$-(Indol-3-yl)ethyl-5'-O-(glycine-N-carbonyl)adenosine (14, II-a1)

(14, II-a1)

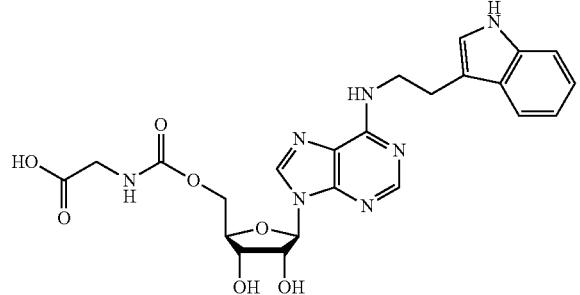

A solution of compound 13 (21 mg, 0.04 mmol) in MeOH (1 mL) and water (0.05 mL) was stirred at 0° C. while TFA (1.3 mL) was added slowly. After the addition was complete, the mixture was warmed to room temperature and stirred for another 2 h. The mixture was concentrated by rotatory evaporation under reduced pressure. The residue was diluted with MeOH (0.5 mL), added 1 M NaOH (2.5 mL), and stirred at room temperature for 15 min. The mixture was concentrated by rotary evaporation under reduced pressure, and purified by reversed-phase column chromatography (RP-18 silica gel, MeOH/H$_2$O, gradients from 1:9 to 1:1) to give compound 14 (II-a1) (14 mg, 74% yield). The purity of product II-a1 was 91.6% as shown by HPLC on Chromolith RP-18 high-resolution column (Merck, 100 mm×4.6 mm), t$_R$=15.4 min ((CH$_3$CN/0.1% TFA aqueous solution, gradients from 5% to 20% in 22 min). C$_{23}$H$_{25}$N$_7$O$_7$; [α]$_D^{25}$=−44.0 (DMSO, c=1); IR v$_{max}$ (neat) 3447, 1793, 1624, 1559, 1456, 1299, 1245, 1096 cm$^{-1}$; $^1$H NMR (400 MHz,CD$_3$OD) δ 8.27 (2 H, br s), 7.59 (1H, d, J=7.6 Hz), 7.32 (1H, d, J=8.0 Hz), 7.10-7.04 (2H, m), 6.99-6.95 (2H, m), 6.04 (1H, d, J=5.2 Hz), 4.68 (2H, t, J=5.2 Hz), 4.38-4.34 (2H, m), 4.31 (1H, d, J=3.6 Hz), 4.25 (1 H, t, J=4.0 Hz), 3.90 (2 H, br s), 3.15-3.11 (2H, m); $^{13}$C NMR (100 MHz,CD$_3$OD) δ 177.3, 158.6, 156.3, 154.2, 140.5, 138.3, 128.9, 123.8, 122.4, 120.9, 120.3, 119.7, 119.5, 113.2, 112.4, 89.6, 84.6, 75.6, 72.1, 65.3, 45.9, 42.7, 26.5; ESI-HRMS calcd for C$_{23}$H$_{24}$N$_7$O$_7$: 510.1737, found: m/z 510.1753 [M−H]$^-$.

N$^6$-((5-Bromothien-2-yl)methyl)adenosine (15)

(15)

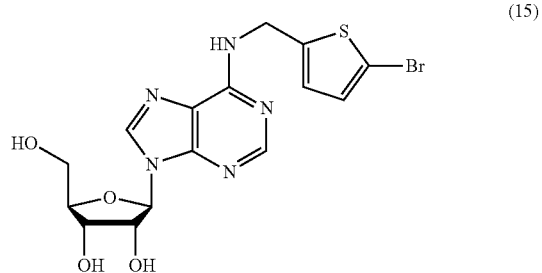

A mixture of 6-chloropurine riboside (287 mg, 1 mmol), 2-aminomethyl-5-bromothiophene (as the hydrochloric salt, 384 mg, 2 mmol) and DIEA (3 mL, 17 mmol) in i-PrOH (8 mL) was heated at 50° C. for 48 h. The mixture was concentrated by rotary evaporation under reduced pressure, added an appropriate amount of MeOH, and centrifugated (8000 rpm, 4° C., 20 min). The precipitate was collected and recrystallized from MeOH to give compound 15 (375 mg, 85% yield). $C_{15}H_{16}N_5O_4SBr$; white solid; mp 153.1-154.7° C.; TLC (i-propanol/hexane (2:3)) $R_f$=0.36; $[\alpha]_D^{25}$=−152.8 (acetone, c=1); IR $v_{max}$ (neat) 3309, 2929, 2869, 1709, 1626, 1584, 1483, 1441, 1347, 1298, 1230, 1125, 1084, 1053 cm$^{-1}$; $^1$H NMR (DMSO-d$_6$, 400 MHz) δ 8.54 (1 H, br s), 8.40 (1 H, s), 8.29 (1 H, br s), 7.02 (1 H, d, J=3.6 Hz), 6.87 (1H, d, J=3.6 Hz), 5.90 (1H, d, J=6.0 Hz), 5.46 (1H, d, J=6.0 Hz), 5.36 (1H, dd, J=6.8, 4.8 Hz), 5.20 (1H, d, J=4.8 Hz), 4.77 (2 H, br s), 4.61 (1H, ddd, J=6.8, 6.0, 6.0 Hz), 4.15 (1H, d, J=2.8 Hz), 3.97 (1H, d, J=2.8 Hz), 3.62-3.73 (1H, m), 3.52-3.60 (1H, m); $^{13}$C NMR (DMSO-d$_6$, 100 MHz) δ 154.0, 152.3, 145.0, 140.2, 129.6, 126.4, 122.9, 109.8, 88.0, 85.9, 73.6, 70.6, 61.6; ESI-HRMS calcd for $C_{15}H_{17}N_5O_4S^{79}Br$ and $C_{15}H_{17}N_5O_4S^{81}Br$: 442.0185 and 444.0164, found: m/z 442.0190 and 444.0167 [M+H]$^+$.

N$^6$-(5-Bromothien-2-yl)methyl-2',3'-O-(isopropylidene)adenosine (16)

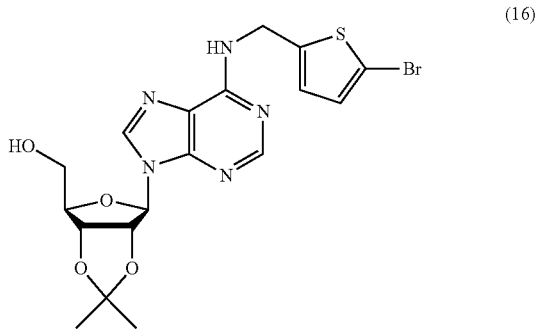

A mixture of compound 15 (150 mg, 0.34 mmol), p-toluenesulfonic acid monohydrate (70 mg, 0.48 mmol) and 2,2-dimethoxypropane (1 mL, 0.83 mmol) in acetone (2 mL) was stirred at room temperature for 4 h. The mixture was concentrated by rotary evaporation under reduced pressure. The residue was diluted with CH$_2$Cl$_2$, extracted successively with water and saturated NaHCO$_3$. The organic phase was dried over MgSO$_4$, filtered, concentrated by rotary evaporation under reduced pressure, and purified by column chromatography (silica gel, hexane/EtOAc (2:3)) to give the acetonide compound 16 (131 mg, 80% yield). $C_{18}H_{20}BrN_5O_4S$; colorless oil; $[\alpha]_D^{25}$=−126.3 (CHCl$_3$, c=1); IR $v_{max}$ (neat) 3422, 1618, 1478, 1382, 1341, 1297, 1264, 1215, 1110, 1081 cm$^{-1}$; $^1$H NMR (400 MHz, CDCl$_3$) δ 8.33 (1 H, br s), 7.67 (1 H, br s), 6.82 (1H, d, J=3.6 Hz), 6.71 (1 H, d, J=4.0 Hz), 5.80 (1H, d, J=4.8 Hz), 5.16 (1 H, t, J=5.2 Hz), 5.07 (1H, dd, J=6.0, 0.8 Hz), 4.85 (2 H, s), 4.49 (1 H, s), 3.92 (1H, d, J=12.0 Hz), 3.76 (1H, d, J=12.0 Hz), 1.60 (3 H, s), 1.33 (3 H,s); $^{13}$C NMR (100 MHz, CDCl$_3$) δ 171.1, 154.4, 152.6, 142.9, 139.7, 129.3, 126.2, 121.1, 113.9, 111.6, 109.2, 94.2, 86.0, 82.9, 81.6, 63.3, 27.6, 25.2; ESI-HRMS calcd for $C_{18}H_{21}^{79}BrN_5O_4S$: 482.0485, found: m/z 482.0498 [M+H]$^+$ N$^6$-(5-Bromothien-2-yl)methyl-2',3'-O-isopropylidene-5'-O-((methyl glycinate)-N-carbonyl)adenosine (17)

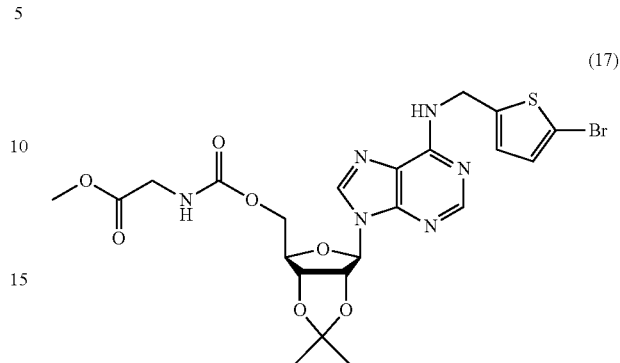

A mixture of compound 16 (208 mg, 0.44 mmol) and CDI (81 mg, 0.55 mmol) in anhydrous THF (17 mL) was stirred at room temperature under nitrogen for 2 h. Another batch of CDI (81 mg, 0.55 mmol) was added, and the mixture was stirred for 2 h. After the reaction was complete (monitored by TLC), a small amount of water was added to quench excess CDI, followed by adding glycine methyl ester hydrochloride (864 mg, 7 mmol 347 mg, 2.8 mmol) and DIEA (1.25 mL, 7 mmol). The mixture was stirred for another 24 h, and then concentrated by rotary evaporation under reduced pressure. The residue was diluted with CH$_2$Cl$_2$, washed successively with 1 M HCl, water and brine. The organic phase was dried over MgSO$_4$, filtered, concentrated by rotatory evaporation, and purified by column chromatography (silica gel, hexane/EtOAc (1:1)) to give compound 17 (118 mg, 45% yield). $C_{22}H_{25}BrN_6O_7S$; colorless oil; $[\alpha]_D^{25}$=−29.7 (MeOH, c=1); IR $v_{max}$ (neat) 3422, 1735, 1719, 1618, 1214, 1076 cm$^{-1}$; $^1$H NMR (400 MHz, CDCl$_3$) δ 8.38 (1 H, br s), 7.84 (1 H, br s), 6.82 (1H, d, J=3.6 Hz), 6.74 (1H, d, J=4.0 Hz), 6.06 (1H, d, J=2.0 Hz), 5.94 (1 H, s), 5.07 (1H, dd, J=6.0, 2.0 Hz), 4.94 (1H, dd, J=6.4, 3.2 Hz), 4.88 (2 H, s), 4.43-4.39 (1H, m), 4.33 (1 H, dd, J=11.6, 4.0 Hz), 4.19-4.15 (1H, m), 3.97-3.83 (2H, m), 3.69 (3 H,s), 1.57 (3 H,s), 1.33 (3 H,s); $^{13}$C NMR (100 MHz, CDCl$_3$) δ 170.4, 155.7, 154.1, 153.2, 148.4, 143.2, 139.4, 129.4, 126.2, 120.2, 114.5, 111.5, 109.4, 90.9, 85.1, 84.1, 81.5, 64.8, 52.4, 42.6, 27.1, 25.3; ESI-HRMS calcd for $C_{22}H_{26}^{79}BrN_6O_7S$: 597.0767, found: m/z 597.0739 [M+H]$^+$.

N$^6$-(5-Bromothien-2-yl)methyl-5'-O-(glycine-N-carbonyl)adenosine (II-b1)

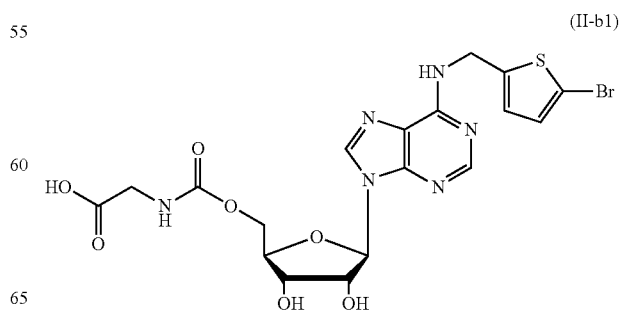

A solution of compound 17 (19 mg, 31 µmol) in MeOH (0.5 mL) and water (0.05 mL) was stirred at 0° C. while TFA (1 mL) was added slowly. After the addition was complete, the mixture was warmed to room temperature and stirred for another 1 h. The mixture was concentrated by rotary evaporation under reduced pressure. The residue was diluted with MeOH (1 mL), added 1 M NaOH (5 mL), and stirred at room temperature for 10 min. The mixture was concentrated by rotary evaporation under reduced pressure, and purified by reversed-phase column chromatography (RP-18 silica gel, MeOH/H$_2$O, gradients from 1:9 to 6:4) to give compound II-b1 (16 mg, 95% yield). The purity of product II-b1 was 95.5% as shown by HPLC on Chromolith RP-18 high-resolution column (Merck, 100 mm×4.6 mm), $t_R$=4.1 min ((CH$_3$CN/0.1% TFA aqueous solution, gradients from 5% to 20% in 22 min). C$_{15}$H$_{19}$BrN$_6$O$_7$S; white solid, mp=171.6-174.0° C.; $[\alpha]_D^{25}$=−16.1 (DMSO, c=1); IR $v_{max}$ (neat) 3448, 1623, 1278, 1119, 1084, 1060 cm$^{-1}$; $^1$H NMR (400 MHz, CDCl$_3$) δ 8.31 (2H, d, J=4.0 Hz), 6.90 (1H, d, J=4.0 Hz), 6.85 (1H, d, J=3.6 Hz), 6.06 (1H, d, J=5.2 Hz), 4.90 (2 H, s), 4.69 (1H, t, J=5.2 Hz), 4.36-4.40 (2H, m), 4.24-4.30 (2H, m), 3.66 (2 H, s); $^{13}$C NMR (100 MHz, CDCl$_3$) δ 177.6, 158.7, 155.7, 154.1, 145.7, 141.0, 130.8, 127.6, 121.0, 112.1, 107.6, 89.6, 84.6, 75.7, 72.2, 65.4, 45.8, 30.9. ESI-HRMS calcd for C$_{18}$H$_{18}$$^{79}$BrN$_6$O$_7$S: 541.0141, found: m/z 541.0140 [M−H]$^-$.

5'-Azido-5'-deoxy-2',3'-O-isopropylidene-N$^6$-(4-(4-methoxybenzyloxy)benzyl)adenosine (18)

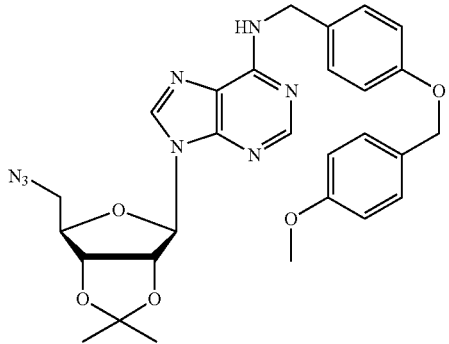

(18)

A mixture of compound 4a (500 mg, 0.94 mmol) and 1,8-diazabicyclo[5.4.0]undec-7-ene (DBU, 420 µL, 2.81 mmol) in 1,4-dioxane (3 mL) was stirred at 0° C. while diphenyl phosphoryl azide (DPPA, 404 µL, 1.88 mmol) was added in one portion. After 10 min, the mixture was allowed to warm to room temperature, and stirred for another 2.5 h. Sodium azide (304 mg, 4.67 mmol) and 15-crown-5 ether (18.5 µL, 0.09 mmol) were added. The mixture was then stirred at 80° C. for 16 h. The mixture was cooled, and concentrated by rotary evaporation under reduced pressure. The residue was diluted with EtOAc, and washed successively with 1 M HCl, NaHCO$_{3(sat.)}$, water and brine. The organic phase was dried over MgSO$_4$, filtered, concentrated under reduced pressure, and purified by column chromatography (silica gel, EtOAc/CH$_2$Cl$_2$ gradients from 1:19 to 2:3) to give compound 18 (368 mg, 70% yield). C$_{28}$H$_{30}$N$_8$O$_5$; white foamy solid; mp 49.2-50.8° C.; TLC (EtOAc/CH$_2$Cl$_2$ (1:3)) R$_f$=0.42; $[\alpha]_D^{25}$=+7.21 (CHCl$_3$, c=2); IR $v_{max}$ (neat) 2929, 2101, 1615, 1583, 1513, 1479, 1464, 1375, 1330, 1295, 1240, 1215, 1173, 1155, 1093, 1034 cm$^{-1}$; $^1$H NMR (CDCl$_3$, 600 MHz) δ 8.42 (1 H, br s) 7.72 (1 H, br s) 7.36 (2H, d, J=8.2 Hz) 7.29 (2H, d, J=8.2 Hz) 6.93 (4H, t, J=7.4 Hz) 6.54 (1H, t, J=5.6 Hz) 6.09 (1 H, s) 5.47 (1H, d, J=6.7 Hz) 5.08 (1H, dd, J=5.9, 3.3 Hz) 4.99 (2 H, s) 4.79 (2 H, br. s.) 4.43-4.35 (1H, m) 3.82 (3 H, s) 3.64-3.51 (2H, m) 1.63 (3 H, s) 1.41 (3 H, s); $^{13}$C NMR (CDCl$_3$, 150 MHz) δ 159.4, 158.2, 154.7, 153.3, 139.2, 130.5, 129.1, 129.0, 128.9, 120.3, 115.0, 114.6, 113.9, 90.6, 85.7, 84.0, 82.1, 69.8, 55.2, 52.3, 43.9, 27.0, 25.3; ESI-HRMS calcd. for C$_{28}$H$_{31}$N$_8$O$_5$: 559.2417, found: m/z 559.2443 [M+H]$^+$.

5'-Deoxy-2',3'-O-isopropylidene-5'-((methyl glycinate)-N-amido)-N$^6$-(4-(4-methoxybenzyloxy)benzyl) adenosine (19)

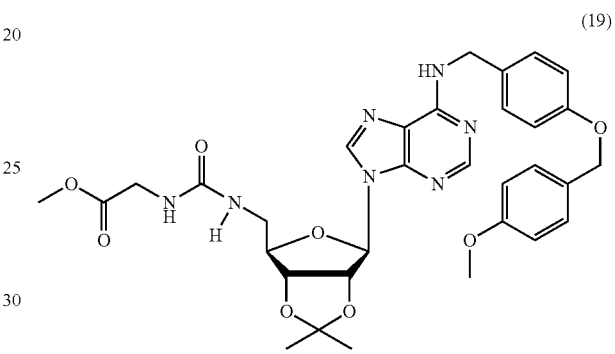

(19)

A mixture of compound 18 (368 mg, 0.66 mmol) and Lindlar catalyst (280 mg, 0.13 mmol) in MeOH (3 mL) and EtOAc (3 mL) was stirred at room temperature under an atmosphere of hydrogen (in balloon) for 24 h to complete hydrogenolysis of azide as shown by TLC. The mixture was diluted with MeOH, filtered through a pad of Celite, and rinsed with MeOH and CH$_2$Cl$_2$. The filtrate was concentrated under reduced pressure to give a crude amine product. Under an atmosphere of nitrogen, the crude amine product was dissolved in anhydrous THF (10 mL), cooled to 0° C., and a solution of 1,1'-carbonyldiimidazole (330 mg, 2.04 mmol) in anhydrous THF (10 mL) was added dropwise with stirring. The mixture was stirred for 1 h, warmed to room temperature, and stirred for another 2 h. Glycine methyl ester hydrochloride (512 mg, 4.08 mmol), Et$_3$N (568 µL, 4.08 mmol) and DMAP (25 mg, 0.20 mmol) were added. The mixture was stirred at room temperature for 16 h, and then concentrated by rotary evaporation under reduced pressure. The residue was diluted with EtOAc, washed successively with 1 M HCl water and brine. The organic phase was dried over MgSO$_4$, filtered, concentrated by rotatory evaporation under reduced pressure, and purified by column chromatography (silica gel, MeOH/EtOAc, gradients from 0:1 to 3:97) to give the urea derivative 19 (379 mg, 86% yield). C$_{32}$H$_{37}$N$_7$O$_8$; white foamy solid; mp 84.6-85.8° C.; TLC (MeOH/DCM (1:9)) R$_f$=0.68; $[\alpha]_D^{25}$=−118.2 (CHCl$_3$, c=2); IR $v_{max}$ (neat) 1750, 1616, 1578, 1559, 1513, 1375, 1297, 1240, 1214, 1175, 1097, 1082, 1034 cm$^{-1}$; $^1$H NMR (CDCl$_3$, 600 MHz) δ 8.49 (1 H, br s), 7.67 (1 H, br s), 7.45 (1H, d, J=8.2 Hz), 7.34 (2H, d, J=8.7 Hz), 7.27 (2H, d, J=8.7 Hz), 6.91 (10H, dd, J=8.7, 3.6 Hz), 6.70 (1H, t, J=5.6 Hz), 5.77 (1H, d, J=5.1 Hz), 5.42-5.34 (2H, m), 4.96 (2 H, s), 4.88 (1H, dd, J=6.0, 1.8 Hz), 4.76 (2 H, br s), 4.46 (1H, dd, J=4.6, 2.0 Hz), 4.13 (1H, dd, J=18.2, 6.4 Hz), 3.98 (1H, ddd, J=14.1, 9.5, 2.0 Hz), 3.90 (1H, dd, J=18.2, 4.9 Hz), 3.80 (3H, s), 3.72 (3H, s), 3.30-3.24 (1H, m), 1.62 (3 H, s), 1.37 (3 H, s); $^{13}$C NMR (CDCl$_3$, 150 MHz) δ 171.7, 159.4, 158.7, 158.2, 155.0, 152.9, 140.1, 130.4, 129.1, 129.0, 128.8, 121.2, 115.0, 114.4, 113.9, 92.9, 84.0, 81.9, 81.7, 69.7, 55.2, 52.1, 42.1, 42.0, 27.5, 25.1; ESI-HRMS calcd for C$_{32}$H$_{38}$N$_7$O$_8$: 648.2782, found: m/z 648.2780 [M+H]$^+$.

5'-Deoxy-2',3'-O-isopropylidene-5'-((methyl glycinate)-N-amido)-N$^6$-(4-hydroxybenzyl)adenosine (20)

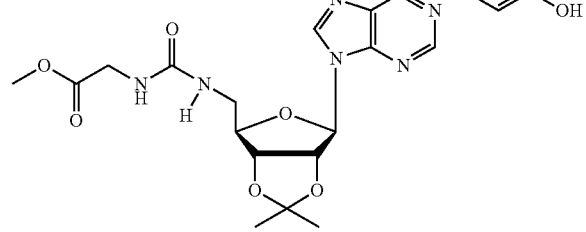

A mixture of compound 19 (100 mg, 0.15 mmol) and 10% Pd/C (82 mg, 0.07 mmol) in MeOH (2.7 mL) and acetic acid (0.3 mL) was stirred at room temperature under an atmosphere of H$_2$ for 3 days. The mixture was diluted with EtOAc, and filtered through a pad of Celite. The filtrate was concentrated by rotatory evaporation under reduced pressure, diluted with EtOAc, and washed successively with saturated NaHCO$_3$, water and brine. The organic phase was dried over MgSO$_4$, filtered, concentrated by rotatory evaporation under reduced pressure, and purified by column chromatography (silica gel, MeOH/CH$_2$Cl$_2$, gradients from 1:99 to 7:93) to give the product 20 (72 mg, 89% yield). C$_{24}$H$_{29}$N$_7$O$_7$; TLC (MeOH/DCM (1:19)) R$_f$=0.35; $^1$H NMR (CDCl$_3$, 600 MHz) δ 8.91 (1 H, br s), 8.42 (1 H, br s), 7.72 (1 H, br s), 7.27 (1 H, br s), 6.98 (2H, d, J=8.2 Hz), 6.74 (1 H, br s), 6.61 (2H, d, J=8.2 Hz), 5.77 (1H, d, J=4.6 Hz), 5.44 (1H, t, J=5.4 Hz), 5.32-5.26 (1H, m), 4.82 (1H, dd, J=6.1, 1.5 Hz), 4.52-4.71 (2H, m), 4.38 (1H, d, J=2.0 Hz), 4.05 (1H, dd, J=18.0, 6.4 Hz), 3.85 (2H, dd, J=18.0, 5.1 Hz), 3.64 (3 H, s), 3.24 (1H, d, J=14.3 Hz), 1.56 (3 H, s), 1.30 (3 H, s); $^{13}$C NMR (CDCl$_3$, 150 MHz) δ 171.7, 158.9, 156.0, 154.6, 153.1, 147.7, 139.8, 129.0, 120.5, 115.5, 114.5, 92.5, 84.1, 82.1, 81.6, 52.2, 43.9, 42.1, 41.9, 27.4, 25.1; ESI-HRMS calcd for C$_{24}$H$_{30}$N$_7$O$_7$: 528.2207, found: m/z 528.2207 [M+H]$^+$.

5'-Deoxy-5'-(glycine-N-amido)-N$^6$-(4-hydroxybenzyl)adenosine (1-d1)

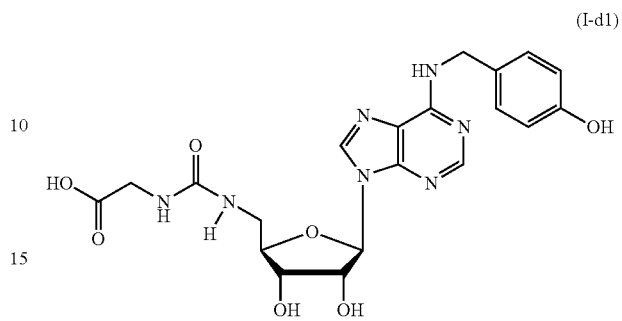

A solution of compound 20 (70 mg, 0.13 mmol) in MeOH (0.8 mL) and water (0.2 mL) was stirred at 0° C. while TFA (2 mL) was added slowly. The mixture was warmed to room temperature and stirred for 2 h. The mixture was concentrated by rotatory evaporation under reduced pressure. The residue was diluted with MeOH (5 mL), 1 M NaOH (5 mL) was added, and stirred at room temperature for 30 min. The mixture was concentrated by rotary evaporation under reduced pressure, purified by reversed-phase column chromatography (RP-18 silica gel, MeOH/water gradients from 0:1 to 3:7) to give compound 1-d1 (61.8 mg, 98% yield). The purity of product 1-d1 was 99.2% as shown by HPLC on Chromolith RP-18 column (Merck, 100 mm×4.6 mm), t$_R$=6.82 min (CH$_3$CN/0.1% TFA aqueous solution, gradients of 0% to 30% in 10 min). C$_{20}$H$_{23}$N$_7$O$_7$; white solid, mp>200° C. (decomposed); [α]$_D^{25}$=−19.5 (H$_2$O, c=1); IR v$_{max}$ (film) 2924, 1623, 1598, 1577, 1398, 1337, 1250, 1171, 1133, 1080 cm$^{-1}$; $^1$H NMR (D$_2$O, 600 MHz) δ 8.05 (1H, s), 8.00 (1H, s), 7.00 (2 H, d, J=8.2 Hz), 6.54 (2H, d, J=8.7 Hz), 5.87 (1H, d, J=5.1 Hz), 4.62 (1H, t, J=5.1 Hz), 4.39 (2 H, br. s.), 4.25 (1H, t, J=5.1 Hz), 4.12 (1 H, q, J=4.6 Hz), 3.58-3.50 (2H, m), 3.45-3.37 (2H, m); $^{13}$C NMR (D$_2$O, 150 MHz) δ 178.1, 165.4, 160.3, 160.1, 153.9, 152.6, 139.2, 128.8, 126.2, 118.9, 117.0, 112.5, 87.6, 83.6, 73.3, 70.9, 43.8, 41.1; ESI-HRMS (negative mode) calcd for C$_{20}$H$_{24}$N$_7$O$_7$: 474.1731, found: m/z 474.1737 [M+H]$^+$.

5'-Acetylthio-5'-deoxy-N$^6$-(4-(4-methoxybenzyloxy)benzyl)-2',3'-(O-isopropylidene)adenosine (21)

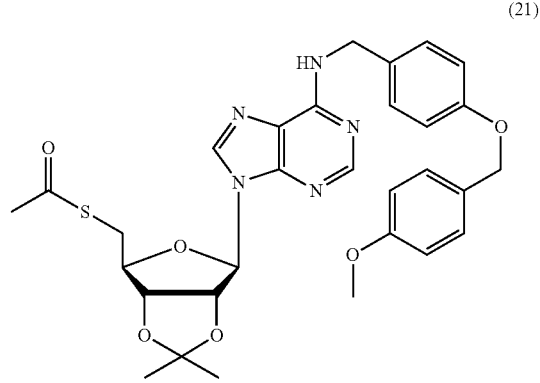

A mixture of $N^6$-(4-hydroxybenzyl)-2',3'-O-isopropylidene-adenosine (3) (291 mg, 0.55 mmol), Et$_3$N (442 μL, 3.2 mmol) and DMAP (2.75 mg, 0.03 mmol) in CH$_2$Cl$_2$ (4 mL) was stirred at 0° C. while a solution of methanesulfonyl chloride (MsCl, 125 μL, 1.62 mmol) in CH$_2$Cl$_2$ (1.5 mL) was added dropwise. The mixture was stirred at 0° C. for 10 min, warmed to room temperature, and stirred for another 2 h. The mixture was concentrated by rotatory evaporation under reduced pressure, diluted with EtOAc, and washed successively with saturated NH$_4$Cl, saturated NaHCO$_3$, water and brine. The organic phase was dried over MgSO$_4$, filtered, concentrated by rotatory evaporation under reduced pressure to give a crude mesylation product. To a solution of the mesylation product in DMF (5 mL) were added KSAc (358 mg, 3.19 mmol) and KI (4.4 mg, 0.03 mmol). The mixture was stirred at room temperature for 20 h, and then concentrated by rotary evaporation under reduced pressure. The residue was diluted with EtOAc, and washed successively with saturated NaHCO$_3$, water and brine. The organic phase was dried over MgSO$_4$, filtered, concentrated by rotatory evaporation under reduced pressure, and purified by column chromatography (silica gel, EtOAc/CH$_2$Cl$_2$ gradients from 0:1 to 3:7) to give compound 21 (242 mg, 74% yield). C$_{30}$H$_{33}$N$_5$O$_6$S; white foamy solid; mp 85.2-86.7° C.; TLC (EtOAc/DCM (1:3)) R$_f$=0.53; [α]$_D^{25}$=-20.39 (CHCl$_3$, c=2); IR v$_{max}$ (neat) 1695, 1616, 1583, 1513, 1465, 1422, 1375, 1330, 1297, 1241, 1216, 1174, 1155, 1091, 1035 cm$^{-1}$; $^1$H NMR (400 MHz, CDCl$_3$) δ 8.38 (1H, s), 7.75 (1H, s), 7.32 (2H, d, J=8.6 Hz), 7.27 (2H, d, J=8.6 Hz), 6.90 (4H, dd, J=8.6, 7.2 Hz), 6.16 (1 H, br. s.), 6.02 (1H, d, J=2.0 Hz), 5.49 (1H, dd, J=6.4, 2.0 Hz), 4.97 (1H, d, J=3.2 Hz), 4.95 (2 H, s), 4.31 (1 H, td, J=6.4, 3.2 Hz), 3.79 (3 H, s), 3.31-3.22 (1H, m), 3.21-3.11 (1H, m), 2.32 (3H, s), 1.57 (3H, s), 1.36 (3 H, s); $^{13}$C NMR (CDCl$_3$, 100 MHz) δ 194.5, 159.4, 158.3, 154.7, 153.3, 139.3, 130.5, 129.2, 128.9, 115.1, 114.4, 114.0, 90.9, 86.1, 84.2, 83.7, 69.8, 55.3, 31.3, 30.5, 27.1, 25.3; ESI-HRMS calcd for C$_{30}$H$_{34}$N$_5$O$_6$S: 592.2230, found: m/z 592.2243 [M+H]$^+$.

5'-Deoxy-5'-((2,2,2-trichloroethyl glycinate)-N-(carbonyl)thio)-N$^6$-(4-(4-methoxybenzyloxy)benzyl)-2', 3'-O-(isopropylidene)adenosine (22)

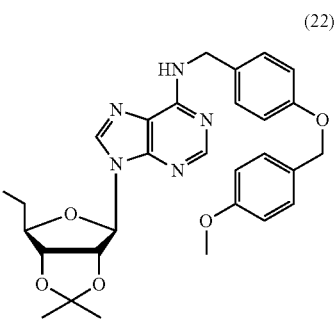

Under an atmosphere of argon, compound 21 (120 mg, 0.20 mmol) was treated in an deoxygenated solution of 1 M KOH$_{(aq)}$ (5 mL), THF (5 mL) and MeOH (5 mL). The mixture was stirred at room temperature for 2 h. A deoxygenated solution of citric acid (1.05 g) in water (10 mL) was added to neutralize the excess base. The mixture was concentrated under reduced pressure to less than 10 mL, diluted with EtOAc, and washed successively with saturated NH$_4$Cl, water and brine. The organic phase was dried over MgSO$_4$, filtered, concentrated by rotatory evaporation under reduced pressure, and purified by column chromatography (silica gel, EtOAc/CH$_2$Cl$_2$ gradients from 0:1 to 1:4) to give a deacetylation product (66 mg, 60% yield).

Under an atmosphere of nitrogen, a solution of 2,2,2-trichloroethyl glycinate (as the hydrochloride salt, 140 mg, 0.58 mmol) and 1,1'-carbonyldiimidazole (140 mg, 0.86 mmol) in CH$_2$Cl$_2$ (0.8 mL) and THF (0.2 mL) was stirred at room temperature for 4 h. The mixture was concentrated under reduced pressure, diluted with CH$_2$Cl$_2$, and washed with brine. The organic phase was dried over MgSO$_4$, filtered, and concentrated by rotatory evaporation under reduced pressure to give a crude imidazolide product.

Under an atmosphere of argon, a THF solution (4 mL) containing the above-prepared deacetylated thiol product (66 mg, 0.12 mmol) and imidazolide was stirred at room temperature for 20 h. The mixture was concentrated by rotary evaporation under reduced pressure, diluted with EtOAc, and washed successively with saturated NH$_4$Cl, water and brine. The organic phase was dried over MgSO$_4$, filtered, concentrated by rotatory evaporation under reduced pressure, and purified by column chromatography (silica gel, EtOAc/CH$_2$Cl$_2$ gradients from 1:9 to 1:4) to give compound 22 (57 mg, 60% yield). C$_{33}$H$_{35}$Cl$_3$N$_6$O$_8$S; TLC (EtOAc/DCM (1:3)) R$_f$=0.35; [α]$_D^{25}$=-51.1 (CHCl$_3$, c=2); IR v$_{max}$ (neat) 1768, 1723, 1669, 1612, 1514, 1457, 1382, 1302, 1241, 1216, 1174, 1157, 1082, 1034, 1008 cm$^{-1}$; $^1$H NMR (CDCl$_3$, 600 MHz) δ 8.38 (1 H, br. s.), 7.80 (1 H, s), 7.34-7.31 (2H, m), 7.29-7.26 (2H, m), 6.94-6.86 (4H, m), 6.20 (1 H, br s), 6.09 (1H, t, J=5.4 Hz), 6.04 (1H, d, J=2.6 Hz), 5.46 (1H, dd, J=6.4, 3.0 Hz), 5.00 (1H, dd, J=6.1, 3.0 Hz), 4.95 (2 H, s), 4.82-4.71 (4H, m), 4.43-4.36 (1H, m), 4.18 (2H, d, J=5.1 Hz), 3.79 (3 H, s), 3.34-3.20 (2H, m), 1.58 (3 H, s), 1.36 (3 H, s); $^{13}$C NMR (CDCl$_3$, 150 MHz) δ 168.0, 159.4, 158.3, 154.7, 153.4, 139.2, 129.2, 128.9, 115.1, 114.5, 114.0, 94.2, 90.8, 86.4, 84.2, 83.5, 74.7, 74.4, 69.8, 55.3, 46.5, 42.5, 39.1, 32.2, 27.1, 25.4; ESI-HRMS calcd for C$_{33}$H$_{36}^{35}$Cl$_3$N$_6$O$_8$S: 783.1353, found: m/z 783.1363 [M+H]$^+$.

5'-Deoxy-5'-(glycine-N-(carbonyl)thio)-N$^6$-(4-hydroxybenzyl)adenosine (I-e1)

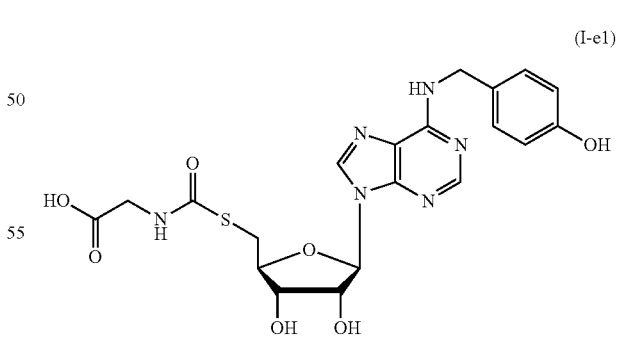

A solution of compound 22 (55 mg, 0.07 mmol) in MeOH (0.8 mL) and water (0.2 mL) was stirred at 0° C. while TFA (2 mL) was added slowly. The mixture was warmed to room temperature, stirred for another 2 h, and then concentrated by rotatory evaporation under reduced pressure. The residue was diluted with MeOH (3 mL) and stirred at room temperature while NaOAc·3H$_2$O (816 mg, 6 mmol), acetic acid (343 μL, 6 mmol) and zinc dust (46 mg, 0.7 mmol) were added. The mixture was stirred at room temperature for 2 h, concentrated by rotary evaporation under reduced pressure, and purified by reversed-phase column chromatography (RP-18 silica gel, MeOH/water gradients from 0:1 to 1:1) to give compound I-e1 (6.0 mg, 17% yield). $C_{20}H_{22}N_6O_7S$; $^1$H NMR (DMSO-d$_6$, 600 MHz) δ 9.22 (1 H, br s), 8.38 (1 H, br s), 8.35 (1 H, s), 8.25 (1 H, br s), 8.22 (1 H, br s), 7.14 (2H, d, J=8.2 Hz), 6.67 (2H, d, J=8.2 Hz), 5.88 (1H, d, J=6.1 Hz), 5.47 (1H, d, J=5.1 Hz), 5.38-5.30 (1H, m), 4.78 (1H, d, J=4.6 Hz), 4.58 (2 H, br s), 4.09 (1 H, br s), 3.94 (1H, d, J=2.0 Hz), 3.72 (2H, d, J=4.6 Hz), 3.10 (1H, dd, J=13.8, 7.2 Hz); ESI-HRMS calcd for $C_{20}H_{23}N_6O_7S$: 491.1343, found: m/z 491.1350 [M+H]$^+$.

6-Chloropurine-2',3'-O-(isopropylidene)riboside (23)

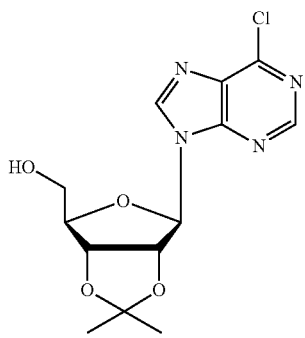

(23)

A mixture of 6-chloropurine riboside (1) (1.0 g, 3.5 mmol), p-toluenesulfonic acid monohydrate (1.0 g, 5.3 mmol) and 2,2-dimethoxypropane (10 mL) in acetone (20 mL) was stirred at room temperature under N$_2$ for 3 h. Another portion of 2,2-dimethoxypropane (10 mL) was added, and the mixture was stirred for another 1 h. The mixture was concentrated by rotary evaporation under reduced pressure. The residue was diluted with CH$_2$Cl$_2$, and extracted with water. The aqueous phase was washed with CH$_2$Cl$_2$, and the combined organic layers were washed with saturated NaHCO$_3$ and brine. The organic phase was dried over MgSO$_4$, filtered, concentrated by rotary evaporation under reduced pressure, and purified by column chromatography (silica gel, EtOAc/hexane gradients from 3:7 to 1:0) to give compound 23 (870 mg, 76% yield). $C_{13}H_{15}ClN_4O_4$; $[α]_D^{25}$=−112.6 (CHCl$_3$, c=2); IR $v_{max}$ (neat) 1592, 1563, 1490, 1438, 1419, 1400, 1384, 1337, 1259, 1202, 1154, 1136, 1108, 1080 cm$^{-1}$; $^1$H NMR (CDCl$_3$, 600 MHz) δ 8.79 (1H, s), 8.25 (1H, s), 6.00 (1H, d, J=4.6 Hz), 5.24-5.21 (1H, m), 5.14 (1H, dd, J=5.6, 1.5 Hz), 4.93 (1H, dd, J=10.6, 2.0 Hz), 4.57 (1H, d, J=1.5 Hz), 4.00 (1 H, dt, J=12.7, 2.0 Hz), 3.84 (1H, ddd, J=12.7, 10.6, 2.3 Hz), 1.68 (3 H, s), 1.41 (3 H, s); $^{13}$C NMR (CDCl$_3$, 150 MHz) δ 152.4, 151.7, 150.4, 144.7, 133.4, 114.5, 94.1, 86.3, 83.2, 81.5, 63.2, 27.6, 25.2; ESI-HRMS calcd. for $C_{13}H_{16}^{35}ClN_4O_4$: 327.0855, found: m/z 327.0868 [M+H]$^+$.

2',3'-O-Isopropylidene-6-[(4-methoxybenzylthio)purine]riboside (24a)

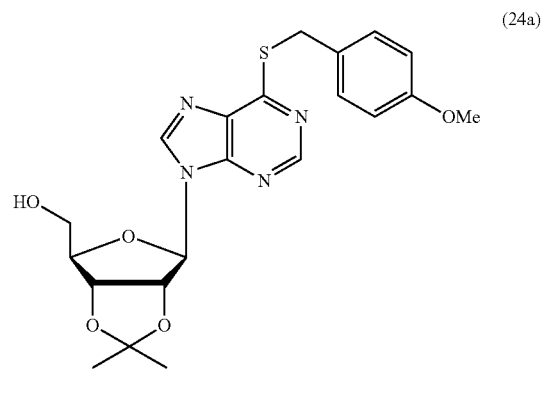

(24a)

A solution of compound 23 (163 mg, 0.5 mmol) and S-(4-methoxybenzyl) thioacetate (106 mg, 0.55 mmol) in MeOH (8 mL) and THF (2 mL) was stirred at 0° C. while K$_2$CO$_3$ (76 mg, 0.55 mmol) was added in one portion. The mixture was stirred at 0° C. for 2 h, diluted with EtOAc, and washed with water and brine. The organic phase was dried over MgSO$_4$, filtered, concentrated by rotary evaporation under reduced pressure, and purified by column chromatography (silica gel, EtOAc/CH$_2$Cl$_2$ gradients from 0:1 to 1:2) to give compound 24a (168 mg, 76% yield). $C_{21}H_{24}N_4O_5S$; white foam; TLC (EtOAc/DCM (1:3)) R$_f$=0.33; $^1$H NMR (600 MHz, CDCl$_3$) Q 8.71 (1H, s), 8.13 (1H, s), 7.36 (2H, d, J=8.4 Hz), 6.82 (2H, d, J=8.4 Hz), 5.96 (1H, d, J=5.4 Hz), 5.19 (1 H, t, J=5.4 Hz), 5.10 (1H, d, J=5.4 Hz), 4.56-4.64 (2H, m), 4.53 (1 H, s), 3.97 (1H, d, J=12.0 Hz), 3.81 (1H, dd, J=12.0, 2.0 Hz), 3.77 (3H, s), 1.64 (3H, s), 1.37 (3 H, s); $^{13}$C NMR (CDCl$_3$, 100 MHz) δ 162.2, 158.8, 151.3, 146.9, 142.2, 132.0, 130.2, 128.8, 114.1, 113.9, 93.9, 86.3, 83.3, 81.5, 63.1, 55.2, 32.5, 27.5, 25.1; ESI-HRMS calcd. For $C_{21}H_{25}N_4O_5S$: 445.1540, found: m/z 445.1543 [M+H]$^+$.

2',3'-O-Isopropylidene-6-[(4-(4-methoxybenzyloxy)benzylthio)purine]riboside (24b)

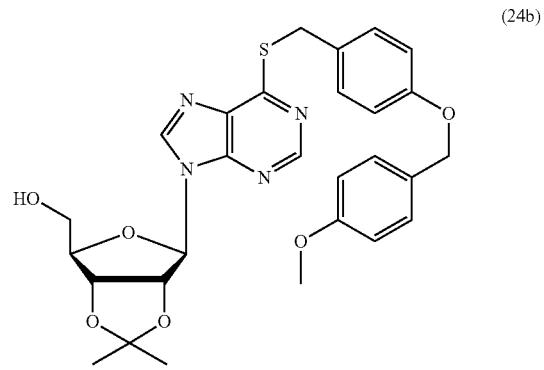

(24b)

A solution of compound 23 (61.8 mg, 0.19 mmol) and S-[4-(4-methoxybenzyloxy)benzyl]thioacetate (63 mg, 0.21 mmol) in MeOH (4 mL) and THF (1 mL) was stirred at 0° C. while K$_2$CO$_3$ (34.6 mg, 0.25 mmol) was added in one portion. The mixture was stirred at 0° C. for 2 h, diluted with EtOAc, and washed with water and brine. The organic phase was dried over MgSO$_4$, filtered, concentrated by rotatory evaporation under reduced pressure, and purified by column chromatography (silica gel, EtOAc/CH$_2$Cl$_2$ gradients from 0:1 to 2:3) to give compound 24a (85 mg, 81% yield). C$_{28}$H$_{30}$N$_4$O$_6$S; white foam; TLC (EtOAc/hexane (1:1)) R$_f$=0.24; $^1$H NMR (600 MHz, CDCl$_3$) δ 8.72 (1H, s), 8.06 (1H, s), 7.38 (2H, d, J=8.7 Hz), 7.34 (2H, d, J=8.7 Hz), 6.91 (4H, d, J=8.7, 2.0 Hz), 5.94 (1H, d, J=4.6 Hz), 5.23-5.19 (1H, m), 5.13 (1H, dd, J=5.9, 1.4 Hz), 4.97 (2 H, s), 4.65-4.58 (2H, m), 4.55 (1H, d, J=1.4 Hz), 3.98 (1H, dd, J=12.5, 1.8 Hz), 3.83 (1H, d, J=1.8 Hz), 3.81 (3H, s), 1.66 (3H, s), 1.39 (3 H, s); $^{13}$C NMR (CDCl$_3$, 100 MHz) δ 162.4, 159.3, 158.1, 146.9, 142.2, 132.4, 130.2, 129.09, 129.06, 128.8, 114.8, 113.9, 93.9, 86.1, 83.1, 81.5, 69.7, 63.2, 55.2, 32.4, 27.5, 25.1; ESI-HRMS calcd for C$_{28}$H$_{31}$N$_4$O$_6$S: 551.1959, found: m/z 551.2983 [M+H]$^+$.

2',3'-O-Isopropylidene-6-(4-methoxybenzylthio) purine-5'-O-((methyl glycinate)-N-carbonyl)riboside (25a)

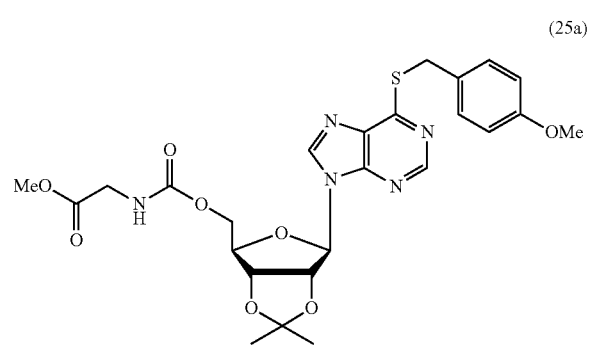

(25a)

A mixture of compound 24a (88 mg, 0.2 mmol) and CDI (97 mg, 0.6 mmol) in anhydrous THF (3 mL) was stirred at room temperature under argon for 3 h. Another batch of CDI (50 mg, 0.3 mmol) was added, and the mixture was stirred for 1 h. After the reaction was complete (monitored by TLC), glycine methyl ester hydrochloride (175 mg, 1.4 mmol), DMAP (1.2 mg, 0.01 mmol) and TEA (194 μL, 1.4 mmol) were added. The mixture was stirred for another 20 h, and then concentrated by rotatory evaporation under reduced pressure. The residue was diluted with EtOAc, washed with saturated NH$_4$Cl$_{(aq)}$, water and brine successively. The organic phase was dried over MgSO$_4$, filtered, concentrated by rotatory evaporation, and purified by column chromatography (silica gel, EtOAc/CH$_2$Cl$_2$ gradients from 0:1 to 1:1) to give compound 25a (96 mg, 85% yield). C$_{25}$H$_{29}$N$_5$O$_8$S; white foam; TLC (EtOAc/DCM (1:9)) R$_f$=0.07; $^1$H NMR (CDCl$_3$, 400 MHz) δ 8.75 (1H, s), 8.23 (1H, s), 7.36 (2H, d, J=8.7 Hz), 6.82 (2H, d, J=8.7 Hz), 6.18 (1H, d, J=2.4 Hz), 5.81 (1H, t, J=5.1 Hz), 5.43 (1H, dd, J=6.0, 2.4 Hz), 5.05 (1H, dd, J=6.0, 4.2 Hz), 4.59 (2 H, s), 4.49 (1H, m), 4.35 (1H, dd, J=11.8, 4.2 Hz), 4.26 (1H, dd, J=11.8, 5.4 Hz), 3.89 (2H, m), 3.76 (3H, s), 3.69 (3H, s), 1.61 (3 H, s), 1.38 (3 H, s); $^{13}$C NMR (CDCl$_3$, 100 MHz) δ170.2, 161.0, 158.8, 155.7, 151.9, 147.6, 141.9, 131.0, 130.2, 128.9, 114.5, 113.8, 90.9, 85.1, 84.1, 81.4, 64.6, 55.1, 52.2, 42.5, 32.4, 27.0, 25.2; ESI-HRMS calcd. for C$_{25}$H$_{29}$N$_5$O$_8$S: 560.1810, found: m/z 560.1817 [M+H]$^+$.

5'-O-(Glycine-N-carbonyl)-6-[(4-methoxybenzyl-thio)purine]riboside (25a)

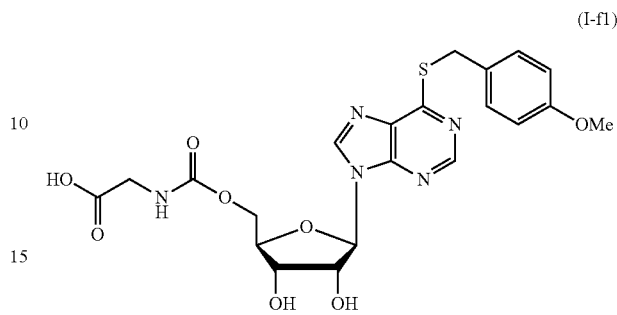

(I-f1)

A solution of compound 25a (10 mg, 0.01 mmol) in MeOH (0.8 mL), THF (0.1 mL) and water (0.1 mL) was stirred at room temperature while formic acid (2 mL) was added slowly. After the addition was complete, the reaction was heated to 40° C. and stirred for another 24 h. The mixture was concentrated by rotatory evaporation under reduced pressure. The residue was diluted with MeOH (2 mL) and H$_2$O (1 mL), stirred at room temperature while K$_2$CO$_3$ (28 mg, 0.2 mmol)) was added. The mixture was stirred for 2 h, and then quenched with saturated NH$_4$Cl (1 mL). The mixture was concentrated by rotatory evaporation under reduced pressure, and purified by reversed-phase column chromatography (RP-18 silica gel, MeOH/water gradients from 0:1 to 9:1) to give compound I-f1 (3.5 mg, 39%). C$_{21}$H$_{23}$N$_5$O$_8$S; TLC (MeOH/AcOH/EtOAc (1:1:8)) R$_f$=0.50; $^1$H NMR (DMSO-d$_6$, 600 MHz) δ 8.80 (1H, s), 8.67 (1H, s), 7.44 (1 H, br s), 7.38 (2H, d, J=8.7 Hz), 6.87 (2H, d, J=8.7 Hz), 6.02 (1H, d, J=5.6 Hz), 4.69 (1H, t, J=5.6 Hz), 4.57-4.65 (2H, m), 4.25 (1H, dd, J=11.8, 2.6 Hz), 4.19 (1H, d, J=4.1 Hz), 4.09-4.17 (2H, m), 3.72 (3 H, s), 3.59 (2 H, d, J=5.1 Hz); $^{13}$C NMR (DMSO-d$_6$, 150 MHz) δ 159.4, 158.5, 156.2, 151.7, 149.5, 148.5, 143.2, 130.8, 130.2, 129.4, 113.9, 87.3, 82.7, 73.1, 70.5, 64.2, 55.1, 42.7, 31.3; ESI-HRMS calcd for C$_{21}$H$_{24}$N$_5$O$_8$S: 506.1340, found: m/z 506.1345 [M+H]$^+$.

Intermittent Cold Stress Model

Female C57BL/6JNarl mice aged 8-12 weeks were purchased from the National Laboratory Animal Center (Taipei, Taiwan). The fibromyalgia model was developed by Ueda's group, in which mice were treated with intermittent cold stress for 2 days (Nishiyori, M.; Ueda, H. Prolonged gabapentin analgesia in an experimental mouse model of fibromyalgia. *Mol. Pain* 2008, 4, 52). Mice treated with intermittent cold stress developed long-lasting (>2 weeks) mechanical and thermal hyperalgesia. Analgesic effects of compound I-a1 (JMF3737) via i.p. (in 0.5% HPβCD) or p.o. (in 1% HPβCD) routes and compound I-d1 (JMF4413) via i.p. (in 0.5% HPβCD) were tested in these mice 5 days after intermittent cold stress. Mechanical hyperalgesia was assayed by testing the withdrawal response of mouse hindpaws to 0.2-mN von Frey filament stimulation. The experiment results are shown in FIGS. 9-12.

Figure 9:
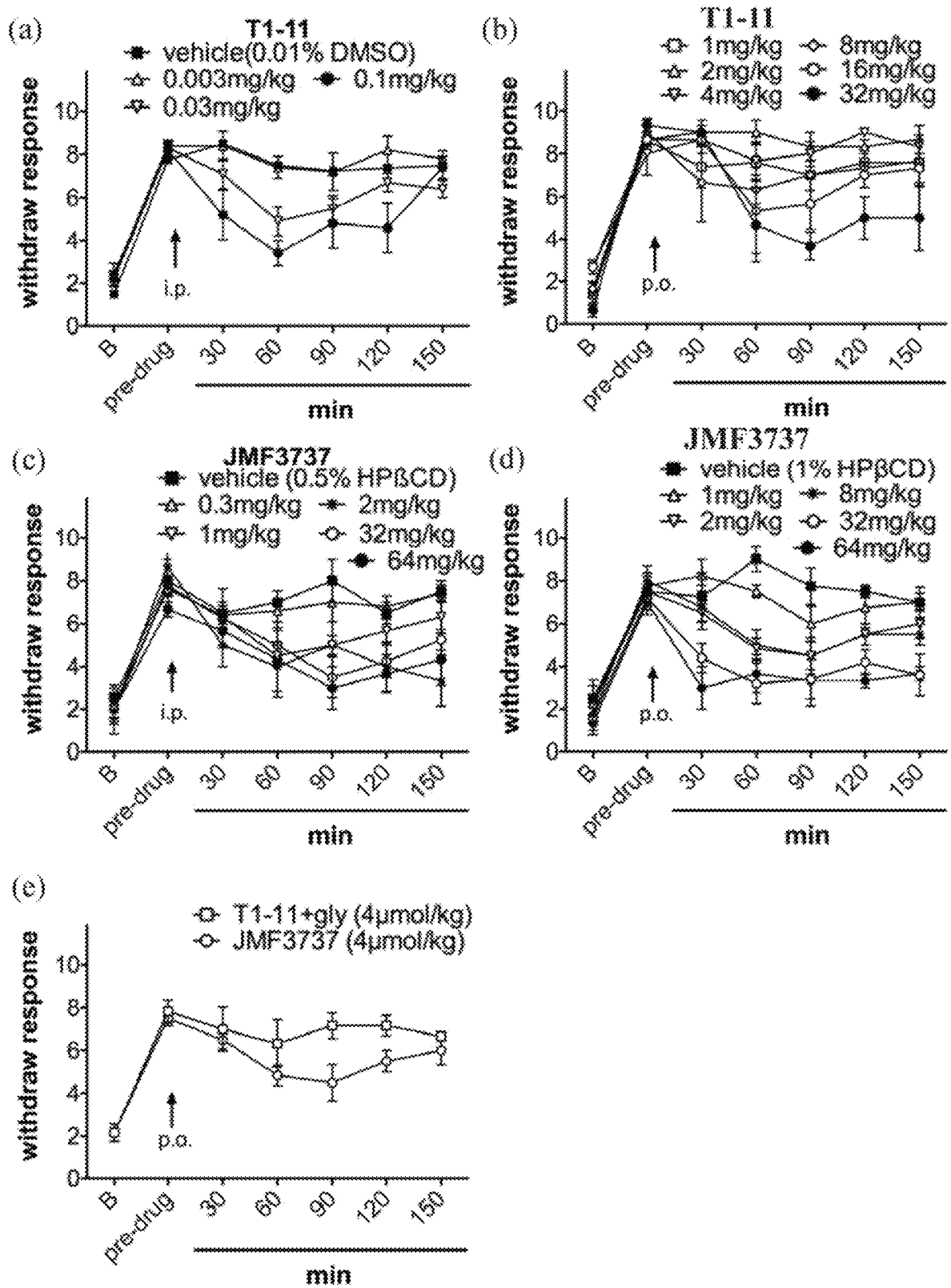
FIG. 9 illustrates the analgesic effects in a mouse model of fibromyalgia, in which chronic widespread pain is induced by intermittent cold stress (ICS). T1-11 shows dose-dependent analgesic effect with effective dose starting from 0.03 mg/kg via intraperitoneal injection (i.p.) and 8 mg/kg via oral gavage (p.o.). In comparison, the conjugate compound I-a1 (JMF3737) derived from T1-11 and glycine shows superior dose-dependent analgesic effect with effective dose starting from 1 mg/kg (i.p.) and 1 mg/kg (p.o.). A combination treatment by oral administration of T1-11 and glycine does not exhibit synergistic effect.

FIG. 9 reveals that T1-11 shows dose-dependent analgesic effect with effective dose starting from 0.03 mg/kg via intraperitoneal injection (i.p.) and 8 mg/kg via oral gavage (p.o.). In comparison, the conjugate compound I-a1 (JMF3737) derived from T1-11 and glycine shows superior dose-dependent analgesic effect with effective dose starting from 1 mg/kg (i.p.) and 1 mg/kg (p.o.). A combination treatment by oral administration of T1-11 and glycine does not exhibit synergistic effect.

FIG. 10 shows a representative whole-cell patch clamp recording, which reveals the analgesic mechanism of action of compound I-a1 (JMF3737); the mechanism is the same as the T1-11 by acting on the NK1R signaling. In muscle nociceptors, JMF3737 induces an outward current ($I_{JMF3737}$) that can be reversibly inhibited (from 40 pA down to 15 pA) by NK1R antagonist (RP67580) in whole-cell patch clamp recording on muscle nociceptors. The JMF3737-induced outward current ($I_{JMF3737}$) can cause nociceptor hyperpolarization and thus counteract the acid-induced depolarization in muscle nociceptors and thus inhibit pain associated with tissue acidosis.

FIGS. 11(a) and 11(b) reveal that no tolerance but therapeutic effect can be obtained by repeated treatments of compound I-a1 (JMF3737). In the fibromyalgia model, mice received oral treatment of 1 mg/kg JMF3737 once a day for 4 consecutive days from day 5 after pain is induced by intermittent cold stress. (a) Repeated treatment of JMF3737 resulted in decreased pain sensitivity to von Frey filament stimulation since day 8 (vehicle, n=2; JMF3737, n=4). (b) Repeated treatment of JMF3737 does not cause tolerance. JMF3737 shows acute analgesic effect from day 5 to day 8 (n=4).

FIG. 12(a) reveals that Conjugate compound of 1-d1 (JMF4413) shows good analgesic effect with dose of 64 mg/kg via i.p. route (n=2). FIG. 12(b) reveals that Conjugate compound of Ic-2 (JMF3795) shows good analgesic effect starting from 14 μg/kg (160 pmol) via i.p. route (n=3).

As a result, the conjugate compounds show (1) a better analgesic effect over T1-11 via oral route (e.g., JMF3737); (2) better solubility (up to 64 mg/kg) than T1-11 (e.g., JMF3737, JMF3795, JMF4413); (3) wider safety ranges (up to 64 mg/kg) than T1-11 (e.g., JMF3737, JMF4413).

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope.

We claim:

1. A compound of formula (I):

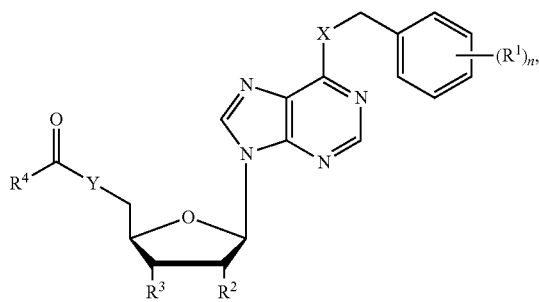

(I)

wherein;

n is 0, 1, 2 or 3;

X is NH, O or S;

Y is O, NH or S;

wherein when n is 1, $R^1$ is OH, $NH_2$, $NO_2$, halogen, alkyl, haloalkyl, hydroxyalkyl, unsubstituted or substituted alkoxy, alkoxyalkyl, alkenyl or alkynyl;

when n is 2 or 3, $R^1$ is independently selected from: OH, $NH_2$, $NO_2$, halogen, alkyl, haloalkyl, hydroxyalkyl, unsubstituted or substituted alkoxy, alkoxyalkyl, alkenyl or alkynyl;

$R^2$ and $R^3$ are each independently OH, $NH_2$, $NO_2$, haloalkyl, hydroxyalkyl or alkylamino; and $R^4$ is selected from an amino acid or a peptide, wherein when $R^4$ is an amino acid, $R^4$ is linked to the C(=O) in the structure via the backbone amino group or side chain amino group, and the carboxy group of the amino acid is optionally a methyl or ethyl ester, and wherein when $R^4$ is a peptide, $R^4$ is linked to the C(=O) in the structure via the N-terminal amino group of said peptide, or a side chain amino group of an amino acid in the peptide, wherein the C-terminal of the peptide is optionally modified;

a tautomer or stereoisomer thereof; and a pharmaceutically acceptable salt of the foregoing.

2. The compound of claim 1, wherein $R^1$, $R^2$, and $R^3$ are each independently OH.

3. The compound of claim 1, wherein n is 1.

4. The compound of claim 1, wherein X is NH and Y is O, NH, or S.

5. The compound of claim 1, wherein X is S and Y is NH.

6. The compound of claim 1, wherein $R^4$ is an amino acid.

7. The compound of claim 1, wherein $R^4$ is an optionally substituted peptide that is less than 20 amino acids in length.

8. The compound of claim 1, wherein $R^4$ is a peptide and the peptide is RPKPQQFFGLM-$CONH_2$ (SEQ ID NO:1), and wherein the peptide is linked with C(=O) in the structure via the side chain amino group of K.

9. The compound of claim 1, wherein the compound is of formula (IA):

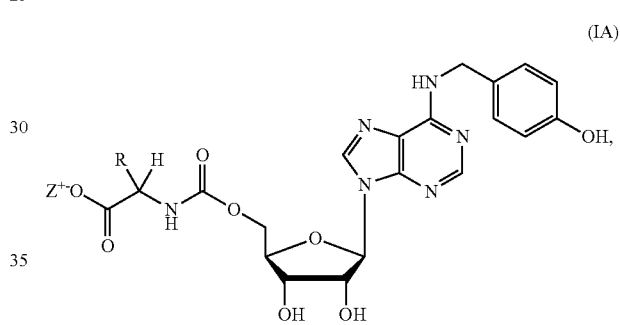

(IA)

wherein;

R is a side chain of glycine, alanine, cysteine, valine, leucine, isoleucine, methionine, phenylalanine, tryptophan, glutamine, asparagine, threonine, arginine, lysine, or proline;

$Z^+$ is $H^+$, $Li^+$, $Na^+$, $K^+$, $Rb^+$, $Cs^+$, $NH_4^+$ or aminium ion; and wherein the aminium ion is $R^A R_B R^C NH^+$; and $R^A$, $R^B$ and $R^C$ are independently H, $C_1$-$C_4$ alkyl, or benzyl; or a tautomer or stereoisomer thereof; and a pharmaceutically acceptable salt of the foregoing.

10. The compound of claim 1, which is selected from the group consisting of:

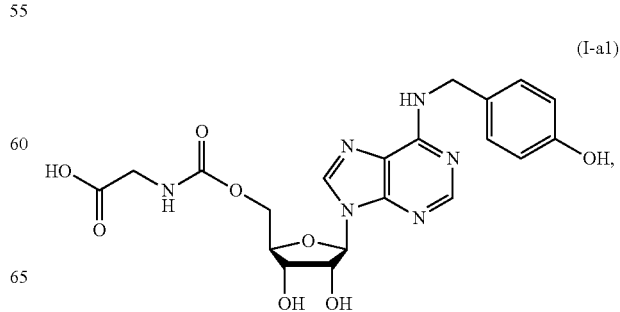

(I-a1)

(I-a2)
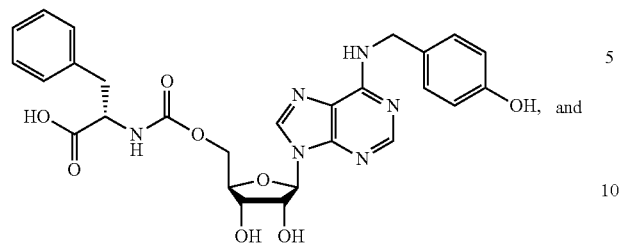
and
(I-a3)
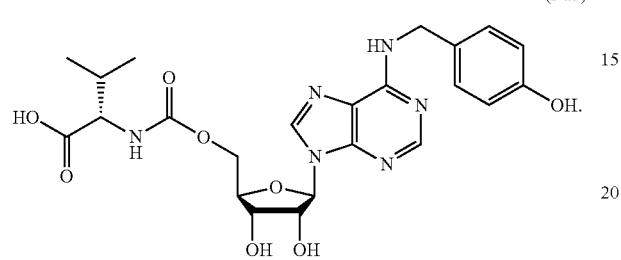
(I-b1)
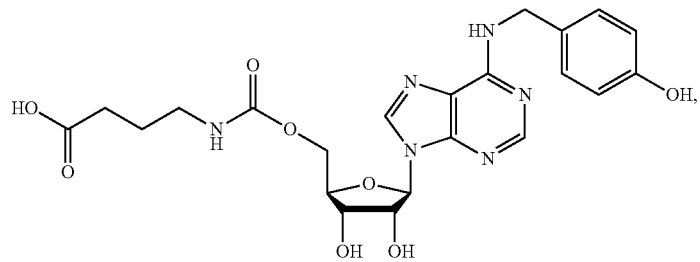
(I-c1)
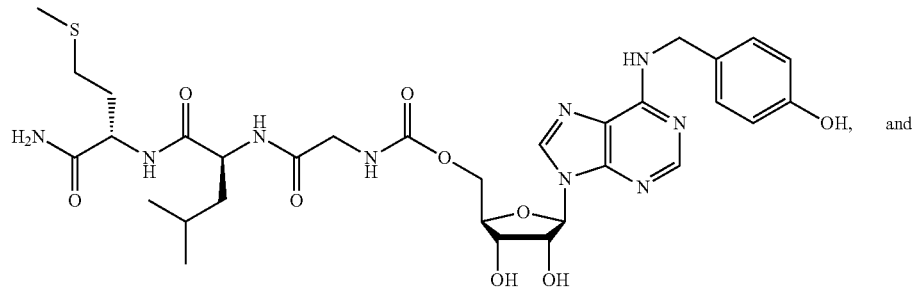
and
(I-c2)
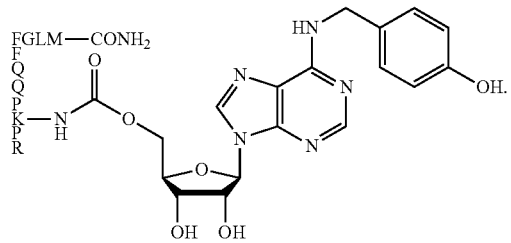

(I-d1)

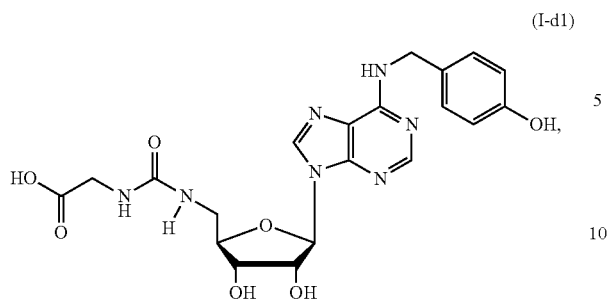

(I-e1)

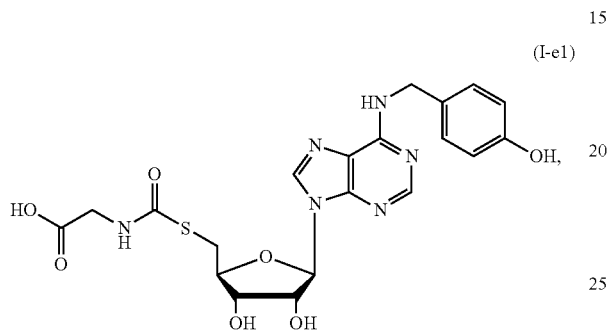

(I-f1)

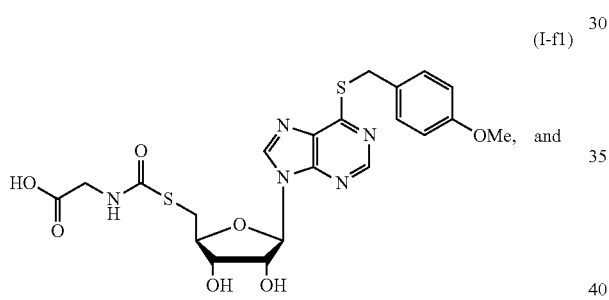

(I-f2)

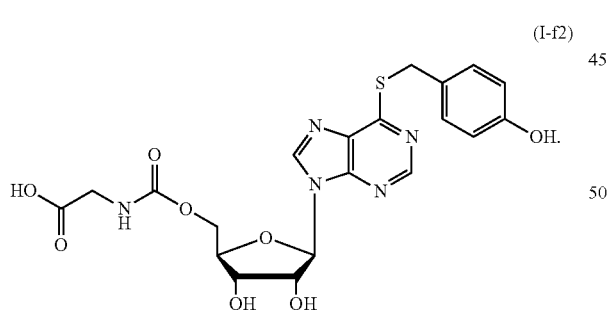

a tautomer or stereoisomer thereof, and a pharmaceutically acceptable salt of the foregoing.

11. A pharmaceutical composition comprising:
(a) a therapeutically effective amount of a compound as claimed in claim 1, a tautomer or stereoisomer thereof, or a pharmaceutically acceptable salt of the foregoing; and
(b) a pharmaceutically acceptable carrier, excipient or vehicle.

12. A method for preparing a compound of formula (I) according to claim 1, (I)

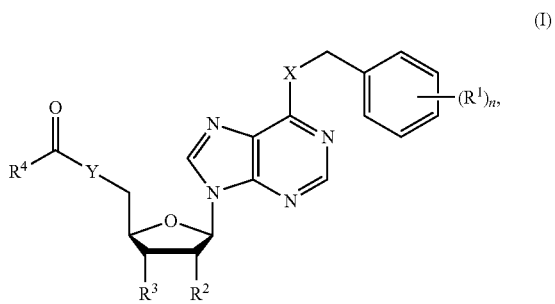

wherein X is NH and Y is O, n is 1, $R^1$, $R^2$ and $R^3$ are each OH, and $R^4$ is as defined in claim 1, the method comprising:

(a) reacting $N^6$-(4-hydroxybenzyl)adenosine with 2,2-dimethoxypropane in acetone in the presence of p-toluenesulfonic acid or camphorsulfonic acid to form a compound of formula (3):

(3)

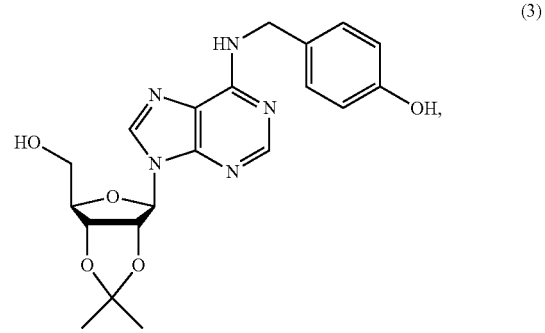

(b) reacting the compound of formula (3) in the presence of a base selected from potassium carbonate or triethylamine with 4-methoxybenzyl chloride or benzoyl chloride to form a compound of formula (4):

(4)

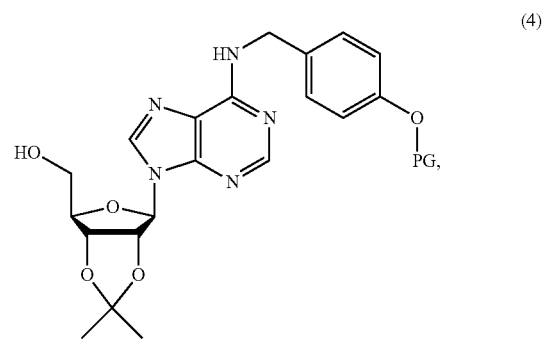

wherein PG is 4-methoxybenzyl or benzoyl;

(c) reacting the compound of formula (4) with 1,1'-carbonyldiimidazole (CDI) in the presence of 4-dimethylaminopyridine (DMAP) to form a compound of formula (5):

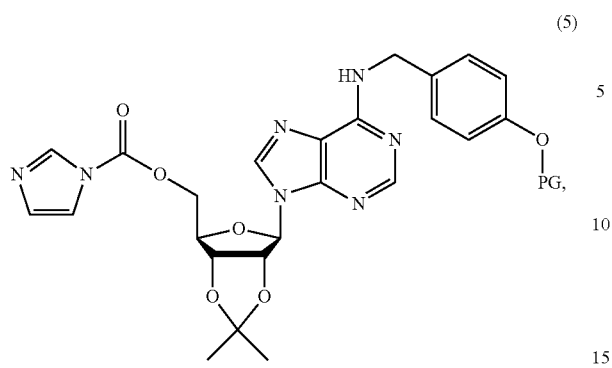

(d) reacting the compound of formula (5) with an amino acid or peptide or salt or ester thereof to form a compound of formula (6):

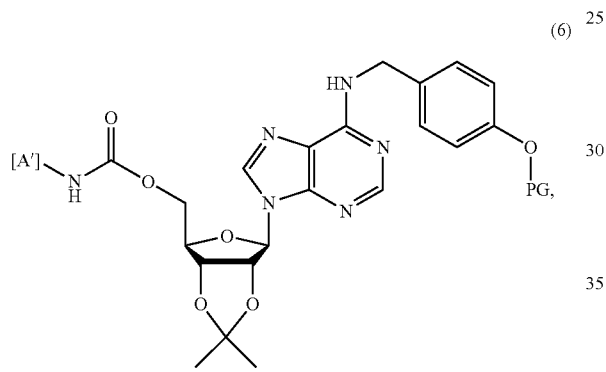

wherein [A']-NH— is an amino acid moiety or peptide moiety or salt thereof; and (e) removing the 4-methoxybenzyl or benzoyl moiety and the 2,2'-dioxypropane moiety to form a compound of formula (IB):

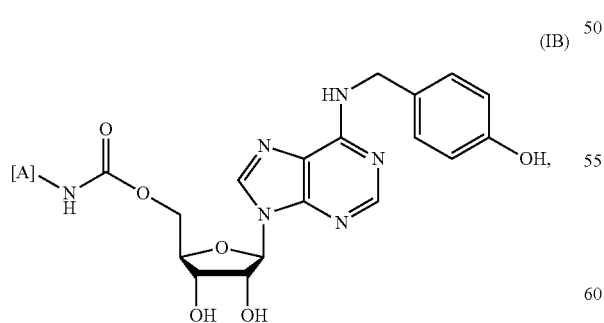

wherein [A]-NH— is the amino acid moiety or the peptide moiety.

13. A method for preparing a compound of formula (I) according to claim 1,

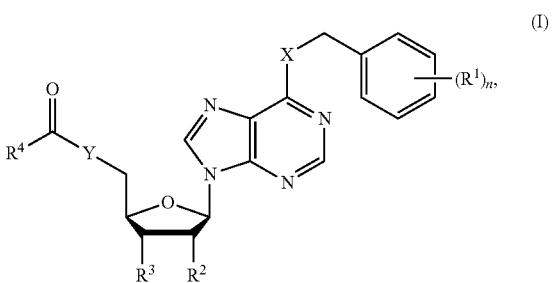

wherein X and Y are NH, n is 1, $R^1$, $R^2$ and $R^3$ are each OH, and $R^4$ is as defined in claim 1, the method comprising:

(a) reacting a compound of formula (4a)

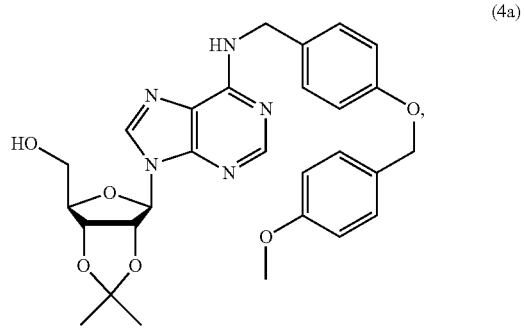

with diphenyl phosphoryl azide (DPPA) and sodium azide in the presence of 1,8-diazabicyclo[5.4.0]undec-7-ene (DBU) to form a compound of formula (18):

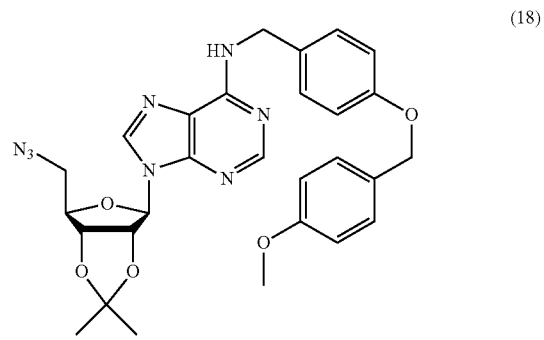

(b) reducing the compound of formula (18) by hydrogenolysis in the presence of a Lindlar catalyst, followed by coupling with glycine methyl ester hydrochloride in the presence of 1,1'-carbonyldiimidazole to form a compound of formula (19):

(a) reacting a compound of formula (4a)

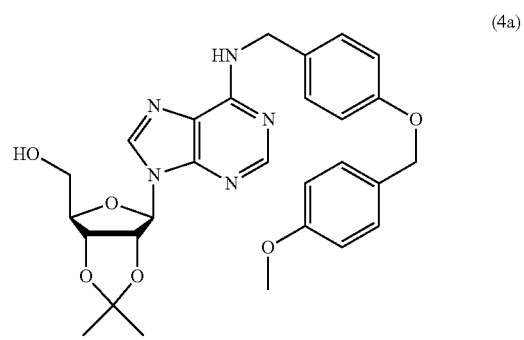

with methanesulfonyl chloride (MsCl) in the presence of triethylamine and 4-dimethylaminopyridine, followed by reacting with potassium thioacetate, to form a compound of formula (21):

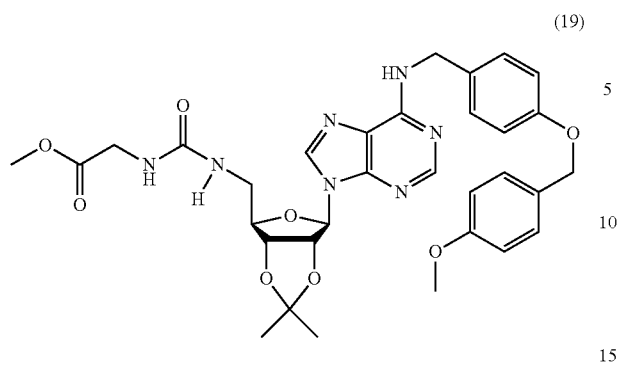

(c) removing the 4-methoxybenzyl moiety, the 2,2'-dioxypropane moiety and the ester from the compound of formula (19) to form a compound of formula (I-d1):

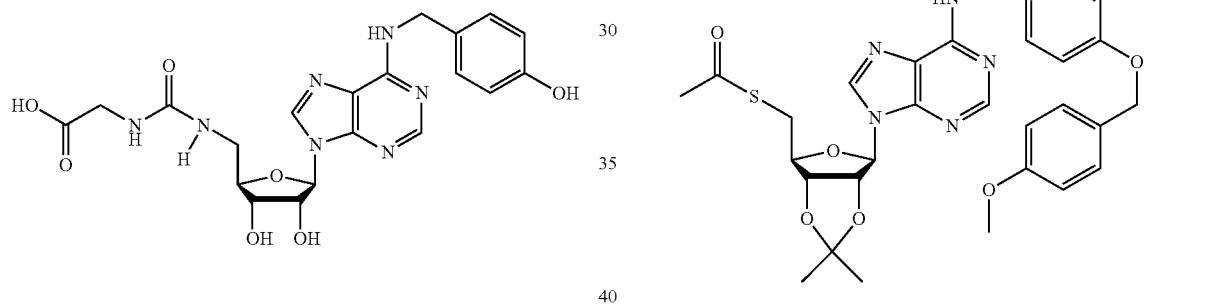

(b) removing the acetyl group from the compound of formula (21) with potassium hydroxide, followed by coupling with 2,2,2-trichloroethylglycine in the presence of 1,1'-carbonyldiimidazole, to form a compound of formula (22):

14. A method for preparing a compound of formula (I) according to claim 1,

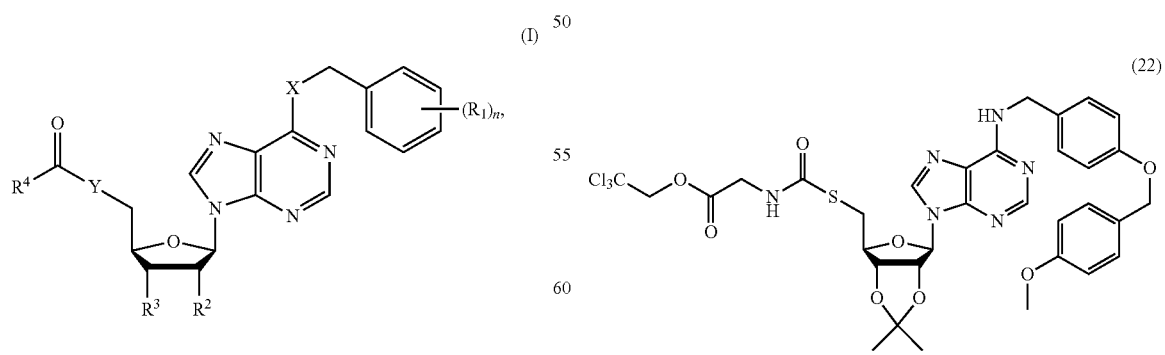

wherein X is NH and Y is S, n is 1, $R^1$, $R^2$ and $R^3$ are each OH, and $R^4$ is as defined in claim 1, the method comprising:

(c) removing the 4-methoxybenzyl moiety, the 2,2'-dioxypropane moiety and the ester from the compound of formula (22) to form a compound of formula (I-e1):

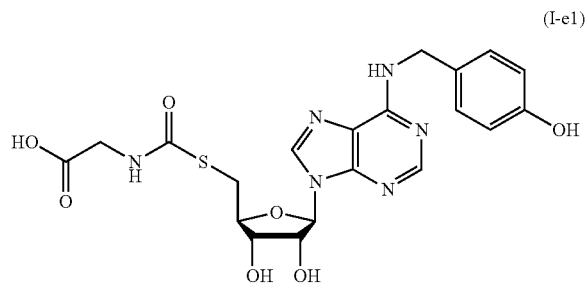

(I-e1)

15. A method of treating acid-induced muscle pain, pain associated with tissue acidosis, or fibromyalgia in a subject in need thereof, the method comprising administering to said subject a compound of formula (I):

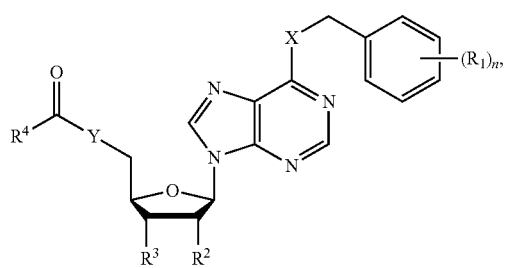

(I)

wherein X is NH and Y is O, n is 1, $R^1$, $R^2$ and $R^3$ are each OH, $R^4$ is selected from an amino acid or a peptide, wherein when $R^4$ is an amino acid, $R^4$ is linked to the C(=O) in the structure via the backbone amino group or side chain amino group, and the carboxy group of the amino acid is optionally a methyl or ethyl ester, and wherein when $R^4$ is a peptide, $R^4$ is linked to the C(=O) in the structure via the N-terminal amino group of said peptide, or a side chain amino group of an amino acid in the peptide, wherein the C-terminal of the peptide is optionally modified, a tautomer or stereoisomer thereof, or a pharmaceutically acceptable salt of the foregoing.

16. A method of reducing neurokinin 1 receptor (NK1R) signaling in a cell, the method comprising contacting said cell with a compound of formula (I):

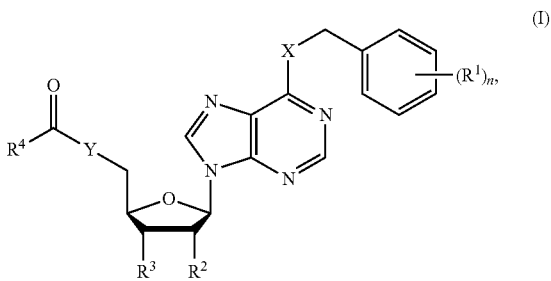

(I)

wherein X is NH and Y is O, n is 1, $R^1$, $R^2$ and $R^3$ are each OH, $R^4$ is selected from an amino acid or a peptide, wherein when $R^4$ is an amino acid, $R^4$ is linked to the C(=O) in the structure via the backbone amino group or side chain amino group, and the carboxy group of the amino acid is optionally a methyl or ethyl ester, and wherein when $R^4$ is a peptide, $R^4$ is linked to the C(=O) in the structure via the N-terminal amino group of said peptide, or a side chain amino group of an amino acid in the peptide, wherein the C-terminal of the peptide is optionally modified.

* * * * *